United States Patent
Torigoshi et al.

(10) Patent No.: US 8,382,735 B2
(45) Date of Patent: Feb. 26, 2013

(54) DISPOSABLE DIAPER WITH SPACED ELASTIC LEG OPENINGS FOR IMPROVED APPEARANCE

(75) Inventors: Keiji Torigoshi, Iyomishima (JP); Yosuke Mori, Iyomishima (JP)

(73) Assignee: Daio Paper Corporation, Iyomishima-shi (JP)

( * ) Notice: Subject to any disclaimer, the term of this patent is extended or adjusted under 35 U.S.C. 154(b) by 248 days.

(21) Appl. No.: 12/759,281

(22) Filed: Apr. 13, 2010

(65) Prior Publication Data

US 2010/0191212 A1 Jul. 29, 2010

Related U.S. Application Data

(62) Division of application No. 10/432,846, filed as application No. PCT/JP01/10380 on Nov. 28, 2001, now Pat. No. 7,727,214.

(30) Foreign Application Priority Data

| Nov. 29, 2000 | (JP) | 2000-362489 |
| Nov. 29, 2000 | (JP) | 2000-362503 |
| Dec. 6, 2000 | (JP) | 2000-371680 |
| Dec. 8, 2000 | (JP) | 2000-374192 |

(51) Int. Cl.
*A61F 13/15* (2006.01)
(52) U.S. Cl. ............ 604/385.28; 604/385.24; 604/396
(58) Field of Classification Search .. 604/385.24–385.3, 604/396
See application file for complete search history.

(56) References Cited

U.S. PATENT DOCUMENTS

| 4,050,462 A | 9/1977 | Woon et al. |
| 4,101,367 A | 7/1978 | Maier |
| 4,486,192 A | 12/1984 | Sigl |
| 4,747,846 A | 5/1988 | Boland et al. |
| 4,795,454 A | 1/1989 | Dragoo |

(Continued)

FOREIGN PATENT DOCUMENTS

| EP | 0 761 194 A2 | 3/1997 |
| EP | 1 027 874 A2 | 8/2000 |

(Continued)

OTHER PUBLICATIONS

Japanese Office Action dated Jun. 6, 2003 and English translation thereof issued in counterpart Japanese Appln. No. 2000-374192.

(Continued)

*Primary Examiner* — Lynne Anderson
(74) *Attorney, Agent, or Firm* — Holtz, Holtz, Goodman & Chick, PC

(57) ABSTRACT

A disposable diaper having a neat appearance. The diaper 101 includes: a liquid-permeable top sheet 111 which covers a use surface side; a leakage preventing sheet 112 which covers a non-use surface side; an absorbent body 113 interposed between the top sheet and the leakage preventing sheet; and an external sheet 120 disposed on an outer surface side of the leakage preventing sheet, wherein three-dimensional gathers BS are formed along leg surrounding portions, and leg cut-out portions of the external sheet which form leg openings are located in a portion of the minimum width of a crotch portion, at a position nearer to a central side than places outward by 5 mm from rising start points of the three-dimensional gathers BS.

9 Claims, 71 Drawing Sheets

U.S. PATENT DOCUMENTS

| | | | |
|---|---|---|---|
| 4,943,340 A | | 7/1990 | Ujimoto et al. |
| 5,449,353 A | * | 9/1995 | Watanabe et al. ......... 604/385.27 |
| 5,476,458 A | | 12/1995 | Glaug et al. |
| 5,599,417 A | | 2/1997 | Glaug et al. |
| 5,601,544 A | | 2/1997 | Glaug et al. |
| 5,649,918 A | | 7/1997 | Schleinz |
| 5,735,839 A | * | 4/1998 | Kawaguchi et al. ...... 604/385.29 |
| 5,807,371 A | * | 9/1998 | Toyoda et al. ............ 604/385.29 |
| 5,817,087 A | * | 10/1998 | Takabayashi et al. ... 604/385.29 |
| 5,833,678 A | | 11/1998 | Ashton et al. |
| 5,851,935 A | | 12/1998 | Srinivasan |
| 5,938,652 A | | 8/1999 | Sauer |
| 5,941,865 A | * | 8/1999 | Otsubo et al. ............. 604/385.29 |
| 5,993,433 A | | 11/1999 | St. Louis et al. |
| 6,049,916 A | | 4/2000 | Rajala et al. |
| 6,159,190 A | | 12/2000 | Tanaka et al. |
| 6,364,863 B1 | * | 4/2002 | Yamamoto et al. ....... 604/385.27 |
| 6,554,815 B1 | | 4/2003 | Umebayashi |
| 2003/0135189 A1 | | 7/2003 | Umebayashi |
| 2004/0015146 A1 | | 1/2004 | Torigoshi et al. |
| 2004/0133180 A1 | | 7/2004 | Mori et al. |
| 2004/0166756 A1 | | 8/2004 | Kurihara et al. |

FOREIGN PATENT DOCUMENTS

| | | |
|---|---|---|
| EP | 1 184 012 A1 | 3/2002 |
| EP | 1 197 196 A1 | 4/2002 |
| EP | 1 205 169 A1 | 5/2002 |
| EP | 1 226 802 A2 | 7/2002 |
| EP | 1 384 459 A2 | 1/2004 |
| GB | 2 253 131 A | 9/1992 |
| JP | 01-183503 A | 7/1989 |
| JP | 04-259459 A | 9/1992 |
| JP | 4-364845 A | 12/1992 |
| JP | 5-076565 A | 3/1993 |
| JP | 6-421 U | 1/1994 |
| JP | 06-197920 A | 7/1994 |
| JP | 06-254117 A | 9/1994 |
| JP | 06-327716 A | 11/1994 |
| JP | 07-117125 A | 5/1995 |
| JP | 07-236650 A | 9/1995 |
| JP | 08-019570 A | 1/1996 |
| JP | 08-191858 A | 7/1996 |
| JP | 08-280736 A | 10/1996 |
| JP | 9-056746 A | 3/1997 |
| JP | 09-056747 A | 3/1997 |
| JP | 09-084824 A | 3/1997 |
| JP | 09-154881 A | 6/1997 |
| JP | 09-271488 A | 10/1997 |
| JP | 9-295366 A | 11/1997 |
| JP | 09-299398 A | 11/1997 |
| JP | 09-299401 A | 11/1997 |
| JP | 10-029259 A | 2/1998 |
| JP | 10-504266 A | 4/1998 |
| JP | 10-201790 A | 8/1998 |
| JP | 11-058638 A | 3/1999 |
| JP | 11-076297 A | 3/1999 |
| JP | 11-107007 A | 4/1999 |
| JP | 11-188060 A | 7/1999 |
| JP | 11-253489 A | 9/1999 |
| JP | 11-299828 A | 11/1999 |
| JP | 11-318978 A | 11/1999 |
| JP | 2000-026015 A | 1/2000 |
| JP | 2000-126231 A | 5/2000 |
| JP | 2000-140014 A | 5/2000 |
| JP | 2000-140021 A | 5/2000 |
| JP | 2000-140022 A | 5/2000 |
| JP | 2000-279444 A | 10/2000 |
| JP | 2000-288017 A | 10/2000 |
| JP | 2000-296150 A | 10/2000 |
| JP | 2000-300603 A | 10/2000 |
| JP | 2001-000478 A | 1/2001 |
| JP | 2001-037808 A | 2/2001 |
| JP | 2001-157690 A | 6/2001 |
| JP | 2001-157690 A | 12/2001 |
| JP | 2002-095692 A | 4/2002 |
| JP | 2002-102282 A | 4/2002 |
| JP | 2002-248127 A | 9/2002 |
| JP | 2002-272784 A | 9/2002 |
| JP | 2002-273808 A | 9/2002 |
| TW | 245955 | 4/1995 |
| WO | WO 88/07337 A1 | 10/1988 |
| WO | WO 96/04874 A1 | 2/1996 |
| WO | WO 00/76444 A1 | 12/2000 |

OTHER PUBLICATIONS

Japanese Office Action dated Aug. 6, 2003 and English translation thereof issued in counterpart Japanese Appln. No. 2001-075266.

Japanese Office Action dated Sep. 11, 2003 and English translation thereof issued in counterpart Japanese Appln. No. 2000-362489.

Japanese Office Action dated Jun. 27, 2008 and English translation thereof issued in counterpart Japanese Appln. No. 2000-371680.

Japanese Office Action (and English translation thereof) dated Sep. 18, 2008, issued in Japanese Application No. JP 2001-076056, which is a Japanese counterpart of related U.S. Appl. No. 10/472,111.

Japanese Office Action (and English translation thereof) dated Jul. 1, 2003, issued in Japanese Application No. JP 2001-074606, which is a Japanese counterpart of related U.S. Appl. No. 10/472,111.

Japanese Office Action (and English translation thereof) dated Jun. 20, 2008, issued int Japanese Application No. JP 2001-074606, which is a Japanese counterpart of related U.S. Appl. No. 10/472,111.

European Notice of opposition to counterpart European Patent EP 1354576 (Application No. 01998294.1) dated Mar. 13, 2012 (in English).

* cited by examiner

CROTCH WIDTH OF EXTERNAL SHEET 120b

CROTCH PORTION OF ABSORBENT BODY 113

FIG. 29(A)  FIG. 29(B)  FIG. 29(C)
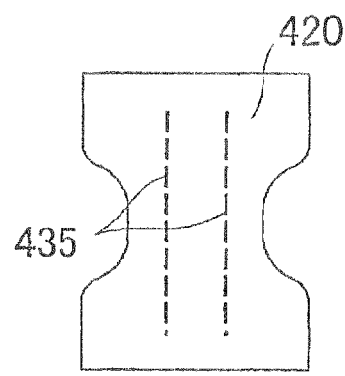
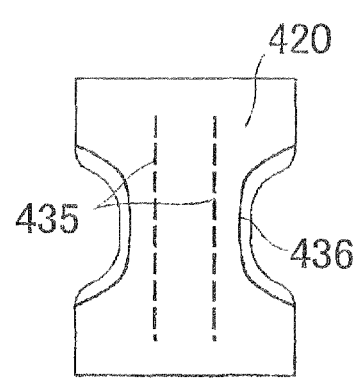
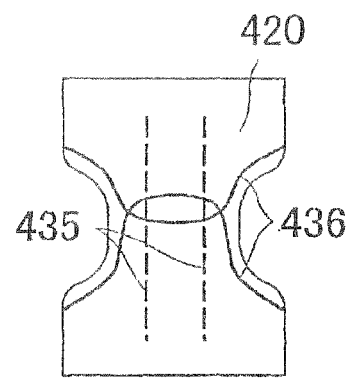
FIG. 29(D)  FIG. 29(E)
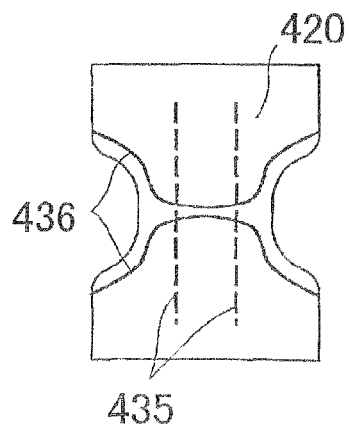
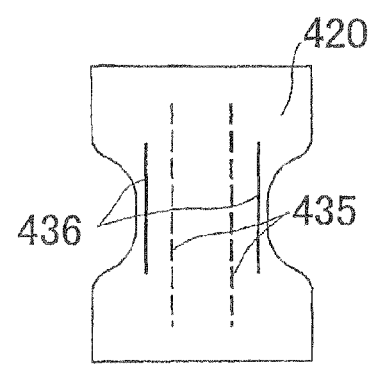

FRONT

BACK

DISPOSABLE DIAPER WITH SPACED ELASTIC LEG OPENINGS FOR IMPROVED APPEARANCE

CROSS-REFERENCE TO RELATED APPLICATIONS

The present application is a Divisional Application of U.S. application Ser. No. 10/432,846 filed May 28, 2003, now U.S. Pat. No. 7,727,214 which is incorporated herein by reference and which is a U.S. National Phase Application under 35 USC 371 of International Application PCT/JP01/10380 filed Nov. 28, 2001.

FIELD OF THE INVENTION

The present invention relates to a disposable diaper having superior visual and functional features and a manufacturing method therefor.

BACKGROUND ART

Conventionally, a disposable diaper as disclosed in Japanese Patent Publication (Laid-open) Toku-kai-hei 7-265357 is known. This disposable diaper is composed of a liquid-permeable top sheet 50, a leakage preventing back sheet 51, and an absorbent body 52 arranged between the both sheets 50 and 51, as shown in FIG. 80(A). The disposable diaper also serves as a pant-type of disposable diaper having a waist opening and a pair of leg openings formed by fastening both side portions of a front side and a back side together. In the both leg opening portions, elastic members 53, 53 ... are continuously arranged along the peripheral edge. In a product state, as shown in FIG. 80(B), it is made into a pleat form by contraction of the elastic members 53, 53 ... along the peripheral edges of the leg openings.

Also, a disposable diaper shown in FIG. 81(A) and FIG. 81(B) is disclosed in one of earlier development by the applicant (Japanese Patent Publication (Laid-open) Toku-kai 2001-178771). As shown in FIG. 81(A), the disposable diaper has: a paper diaper main body 63 including a structure which has a liquid-permeable top sheet 60 composed of mainly nonwoven fabric or the like, a waterproof film 61 composed of polyethylene or the like, and an absorbent body 62 such as a cottony pulp interposed between them; and an external sheet 64 integrally disposed on the outside of the diaper main body 63. The external sheet 64 comprises a back sheet nonwoven fabric 65 for an inner surface and a back sheet nonwoven fabric 66 for an external surface, which are laminated by a hot-melt adhesive. Elastic members 67 to 71 with various functions are interposed between the back sheet nonwoven fabric 65 and the back sheet nonwoven fabric 66, to be fastened by a hot-melt adhesive. Thereby the leakage of excretion is prevented and the property of fitting to the physique of a wearing person is improved.

Specifically, a plurality of elastic members 67 ..., 68 ..., e.g., a band rubber or the like, for around a waist are provided in the opening portions of front side section F and the opening of back side section B, respectively. A plurality of elastic members 69, 69 ... are provided along lateral direction in the positions corresponding to the belly on a front side section F. In addition, a plurality of front side lifting elastic members 70, and 70 ... composed of a thin rubber thread or the like are provided. Both ends of the elastic members 70 and 70 are located in the position corresponding to the belly on a front side section and the central portion of which is swelling downward to the under-the thigh portion. Also, a plurality of stretching elastic members for hip region 71 and 71 ... are provided along the transverse direction at the hip region corresponding to the abdominal region of rear body B.

In such a pant-type of disposable diaper, as shown in FIG. 81(B), the stretching elastic members are not arranged along leg surrounding portions, therefore, pleat-form is not obtained as described above, but frills are formed along the leg surrounding portions.

However, in a pant-type of disposable diaper, as described above, when the frills are formed along the leg surrounding portions, the impression of prettiness is reinforced, but neat design is not obtained. And also the frills contact skin to cause itchiness to a wearing person, and further when wearing trousers thereon, the wearing person feels stiffening. This tendency is pointed out also by a questionnaire performed by this applicant recently. Conversely, it becomes clear that a disposable diaper presenting a neat appearance along the leg surrounding portions is preferred.

Also, in case of the disposable diapers, the ratio of crotch width to product width, and the ratio of side edge length to product length are large, therefore the impression of the crotch section becomes bulky, hardly presenting a neat appearance.

Moreover, pant-types of disposable diapers are constituted in such a way that both side edges of the front side section and the back side section of the external sheet are fastened to form a waist opening and a pair of right and left leg opening portions. In the center of the product width direction, a main absorptive body composed of an absorbent core interposed between a liquid-permeable top sheet and a leakage preventing back sheet is provided in a longitudinal direction extending from the front side section to the back side section. The pant-type of disposable diaper thus constituted is widely used.

Especially, in a belly side and a back side respectively, the pant-type of paper diaper has a plurality of stretching elastic members fastened with spaces in parallel along the peripheral direction of the body peripheral region ranging from the margins of the waist opening to the leg openings. The body peripheral region can be conceptionally divided into a waist section and an under waist section, and a plurality of elastic members are attached, respectively. The elastic members for waist and under-waist section certainly prevent the disposable diaper from slipping down. And especially the elastic members for under-waist section provide a product that is good in compatibility with the skin.

Further, there is also the so-called tape type disposable diaper, i.e., the type that fastens both right-and-left side edges on the belly side and both right-and-left side edges on the back side at the time of diaper use (at the time of wearing). This type of disposable diaper that includes no elastic members formed therein is widely used.

By the way, in the conventional paper diaper, edges of the leg openings in the crotch region that forms the leg openings is the remaining portion of the cut margin or a main absorptive body attachment margin in manufacture process, (henceforth a margin), having no stretchable members attached thereto, and formed of the material of the external sheet only (usually nonwoven fabric).

However, the edge of the leg openings serving as a margin is constituted in wave-like form and flatters, involving a problem of presenting bad appearance due to an unnecessary sense of volume body peripheral region.

On the other hand, it is considered that the problem is overcome by cutting the leg openings so that the margin may be lost. However, the margin may be unnecessary in a product state in manufacturing process, but it is required as cut margin or main absorptive body attachment margin. Therefore, it is not preferable to lose such a margin in view of manufacture.

Further, in the pant-type of disposable diaper currently used widely, a thin rubber thread is usually used as stretchable members arranged body peripheral region in recent years. The stretchable members are occasionally used for both of the waist opening section and under waist section, extending to a crotch section. In case of the under waist section, the stretchable member is made unevenly distributed in the waist opening side, not in the whole region of the under waist section. The arrangement space between the stretchable members is 10 mm or more. In addition, usually the arrangement space between the stretchable members in the waist opening section is small, whereas, the arrangement space between the stretchable members of the under waist section is made large, in order to prevent too much abdominal pressure.

On one hand, in order to prevent slipping down when wearing a product, diameter of each thin rubber thread is made large to enlarge shrink force.

On the other hand, in recent years, in order to give a soft feel, a nonwoven fabric sheet is arranged on the outside of the back side sheet made from plastic. This tendency is especially true of pant-type of paper diapers.

However, if the sheet that constitutes the external surface of a product is formed by a nonwoven fabric and a thin rubber thread is arranged to the use side of the nonwoven fabric, existence of the thin rubber threads is visible through the nonwoven fabric, due to the rough in-between structure of the nonwoven fabric. For a wearing person, the wearer's skin is rebuked by the thin rubber thread, and especially traces of rubber are possibly formed on the skin, resulting in the decline in consumer confidence.

Further, the nonwoven fabric has flexibility as compared with plastic sheets, such as polyethylene. Therefore, generation of wrinkles is remarkable in product external surface, and, further, indecent wrinkles occur. That is, in the stage of not wearing, as shown in FIG. 36(A), the wrinkles generated accompanying the stretching of the thin rubber threads G are generated with the form ranging from one side to another side of the adjoining thin rubber threads G. The uneven wrinkles generate repeatedly in the body peripheral direction. Furthermore, the adjoining wrinkles between thin rubber threads G and the next adjoining wrinkles thereto between thin rubber threads G do not continue, but are apt to generate independently.

When the arrangement space between mutual thin rubber threads is large, these wrinkles have long ridge or valley according to the separating distance of the mutual thin rubber threads, and the pitch of the unevenness in the body peripheral direction is large. Accordingly, if viewed on the whole in the external surface of a product, large wrinkles generate at random. The external surface of the product becomes stuffy, and the image is far from the pant-type of clothing.

Furthermore, each thin rubber thread G in the conventional product is thick, and its shrink force is large. Therefore, if one ridge wrinkle is taken for an embodiment, the valley on the thin rubber threads G side becomes deep, making the existence of the thin rubber thread G conspicuous. Further, since the ridge or the valley is large and shrink force acts strongly, complicated fine wrinkles generate at random in the ridge portion or the valley portion.

On the other hand, the existence of the thick rubber threads G is visible through the non-woven fabric. Therefore, it is feared that thick rubber threads G possibly bind a wearing person's skin tight strongly. Actually, in the side portion in which an absorbent body does not exist, the shrink force of the thick rubber threads G acts strongly, thereby forming traces of rubber. Further, friction of the inner surface of the product and the skin mainly in the portion where each rubber thread contact with the skin prevents the product from slipping down. However, since there are few rubber thread numbers per unit area, if very large shrinkage force does not work, the product may possibly slip down.

An object of the present invention is to provide a disposable diaper having a neat appearance of around leg openings, to overcome the above-described problem, and to provide a method for manufacturing the same.

Another object of the invention is to provide a disposable diaper having a neat appearance of crotch portion and around leg openings, to overcome the above-described problem.

A further object of the invention is to provide a disposable diaper with elastic members, existence of which is invisible or hardly visible, so as to make a wearing person undaunted by anxiety about excessive tightening and formation of traces of rubber, and provide a disposable diaper capable of solving the problem that the elastic members are visible, and appealing to consumers by high-class feeling of a product and good finish thereof.

A further object of the invention is to provide a disposable diaper excellent in appearance with no conspicuous wrinkles, having a neat appearance, that is, having no stuffy external surface with fine wrinkles even if wrinkles are generated, and presenting a flat face on the whole. And another object of the invention is to provide a disposable diaper with no formations of traces of rubber by being pressed to the skin on the face, avoiding too much pressure to the skin locally, and capable of improving the property of fitting to the physique of a wearing person by friction of the inner surface of the product and the skin on the whole surface, to thereby prevent the product from slipping down.

Another object of the invention is to provide a disposable diaper having leg opening edges hardly flutterable, having sufficient fitting property of leg surrounding portions, and good in appearance.

SUMMARY OF THE INVENTION

The applicant has studied earnestly with the structure of a disposable diaper that has a neat appearance in leg surrounding portions, with a result that, as a concrete technique, leg cut-out portions position of an external sheet that forms leg-openings is specified with respect to an absorbent body in the crotch portion area of a disposable diaper, and leg cut-out portions position of the external sheet is specified with respect to rising start points of the three-dimensional gathers, to thereby achieve a neat appearance of a disposable diaper.

In order to overcome the above-described problems, in accordance with a first aspect of the present invention, the disposable diaper comprises: a liquid-permeable top sheet which covers a use surface side; a leakage preventing sheet which covers a non-use surface side; an absorbent body interposed between the liquid-permeable top sheet and the leakage preventing sheet; and an external sheet disposed on an outer surface side of the leakage preventing sheet. In the diaper, leg cut-out portions of the external sheet, which form leg openings may be located in a portion of the minimum width of a crotch portion, at a position nearer to a central side than places outward by 5 mm from side edges of the absorbent body.

In accordance with a second aspect of the invention, the disposable diaper has an absorbent body interposed between a liquid-permeable top sheet that covers a use surface and a leakage preventing sheet that covers a non-use surface, an external sheet arranged on the leakage preventing sheet, and three-dimensional gathers are formed along the leg surrounding portions, wherein leg cut-out portions of the external sheet forming leg openings are positioned nearer to the center than places outward by 5 mm from the rising start points of the three-dimensional gathers.

In this case, elastic members may be arranged along the longitudinal direction of the disposable diaper, on both sides of the absorbent body or near both sides of the absorbent body. The sides of the absorbent body may be raised along the longitudinal direction of the paper diaper by the elastic members to form the rising start point of the three-dimensional gathers. The leg cut-out portions of the external sheet that forms the leg opening may be positioned nearer to the center than places outward by 5 mm from rising start points of the three-dimensional gathers. Also, it is preferable that width of a non-bonded side edge along the leg cut-out line of the crotch portion of the external sheet that is integrally bonded by adhesion is 15 mm or less.

In accordance with a third aspect of the invention, the disposable diaper has an absorbent body interposed between a liquid-permeable top sheet which covers a use surface and a leakage preventing sheet that covers a non-use surface, and an external sheet arranged on the leakage preventing sheet, wherein leg cut-out portions of the external sheet forming leg openings are positioned nearer to the center than places outward by 5 mm from the side edges of the absorbent body. Here, a side edge width along the leg cut-out line of the crotch section of the external sheet that is integrally bonded by adhesion is 5 mm or less.

In accordance with a fourth aspect of the invention, the manufacture method for the disposable diaper is a method for manufacturing the disposable diaper according to the first to third aspects of the invention, wherein the method comprises the steps of: cutting leg surrounding portions from a continuous web of an external sheet, thereafter laminating a liquid-permeable top sheet for covering a use surface side, a leakage preventing sheet for covering a non-use surface side and an absorbent body interposed between the both sheets, to form a main body of a paper diaper, and thereafter cutting the external sheet for every disposable diaper.

Moreover, this applicant has studied earnestly with a structure that has a neat appearance in a crotch portion and leg surrounding portions, with a result that leg cut-out portions line is deepened in the longitudinal direction, and crotch width is narrowed, to thereby obtain a neat impression in the crotch portion.

Consequently, in order to overcome the above-described problem, according to a fifth aspect of the invention, the disposable diaper has an absorbent body interposed between a liquid-permeable top sheet that covers a use surface and a leakage preventing sheet that covers a non-use surface, and an external sheet arranged on the leakage preventing sheet, wherein in a product state, two-folded across the crotch portion, the ratio of a side joint length to a diaper product length is 50% or less, and the dimensional ratio of the larger one of width of an external sheet in crotch portion and width of an absorbent body to a waist opening product width is 40% or less.

In this disposable diaper, since the absorbent body width of the crotch portion becomes narrow compared with the conventional disposable diaper as a result, there is a case where it does not become possible to secure sufficient absorption ability. Then, it is preferable to form a thick bulky portion in the range of the absorbent body for retaining the humor discharge as a first technique, aiming at increase of absorption ability partially. As a formation range of the thick bulky portion, it is preferable for a width size to be set to 20 to 90% of absorbent body crotch width, and for a length size to be set to 20 to 90% of absorbent body length. Moreover, as a second technique, it is preferable to form three-dimensional gathers including an absorbent body by raising both sides of the absorbent body in the longitudinal direction toward a use surface side. The three-dimensional gathers raised by this absorbent body functions in such a way as to stop body fluid certainly, and the body fluid is absorbed and retained. Therefore, disadvantage that the size of the absorbent body of the crotch section becomes small in width to lose absorption ability, can be certainly covered.

In addition, width of the waist opening product means the inner width between heat-seal joints of both-sides when no expansion and contraction elasticity by the elastic members acts. Width of the absorbent body of the crotch section means the width of the absorbent body itself containing no crepe paper.

Moreover, in order to obtain a good impression of the leg surrounding portions, it is preferable to make as few frills as possible by the external sheet in the leg surrounding portions. For the purpose, leg cut-out portions position of an external sheet that forms leg-openings is specified with respect to an absorbent body in the crotch portion area of a disposable diaper, and leg cut-out portions position of the external sheet is specified with respect to rising start points of the three-dimensional gathers, to thereby achieve a neat appearance of a disposable diaper.

The concrete structure is formed in such a way that leg cut-out portions of the external sheet forming leg openings are positioned nearer to the center than places outward by 5 mm from the side edges of the absorbent body, and leg cut-out portions of the external sheet forming leg openings are positioned nearer to the center than places outward by 5 mm from the rising start points of the three-dimensional gathers.

In accordance with a sixth aspect of the invention, in a use state, this disposable diaper is composed of a crotch portion in which a waist opening and a right and left leg openings are formed, and a body peripheral region, wherein the elastic members that make the leg opening edges shrink toward the central portion of the width direction is provided.

According to such a structure, as shown in FIG. 35(B), FIG. 37 and FIG. 39, which will be referred to hereafter, the leg opening edges of the crotch area that forms the leg opening portions can shrink toward the central portion in diaper width direction, thereby reducing a margin and forming a plurality of fine wrinkles along the longitudinal direction (direction that intersects perpendicularly with shrinking direction). The rigidity of the leg opening edges increases by these vertical fine wrinkles. By the above actions, the leg opening edges stop flattering in wavelike form like conventional products, and a neat appearance of the leg surrounding portions is achieved and good appearance of the disposable diaper is obtained.

In addition, the elastic members may be provided in parallel with the body peripheral region.

In a sixth aspect of the invention, as long as the leg opening edges can shrink toward central portion of the width direction, direction of the elastic members is no object. However, the elastic members are preferably provided in parallel with the body peripheral region.

Moreover, in the crotch region, the diaper may further comprise an absorbing core which is disposed at a central region in a width direction along a longitudinal direction, and the elastic members may be continuously provided from the leg opening edges to a position near the absorbent body or to the position corresponding to the absorbent body, in parallel to a body peripheral region.

According to such a structure, as shown in FIG. 35 (B), because the elastic members are continuously provided from the leg opening edges to a position near the absorbent body or to the position corresponding to the absorbent body, in parallel to a body peripheral region, and rigidity of the absorbent core is high in comparison with that of the external sheet (It is hard to bend and hard to shrink.), the leg opening edges shrink along the direction parallel to the waist section toward the central portion of the absorbent core of width direction. Therefore, the leg opening edges cannot flutter further easily, presenting a neat appearance in the body peripheral region to produce a disposable diaper of good appearance.

Further, the elastic members may not be provided at a position corresponding to a portion or whole portion of the absorbent core. Accordingly, the portion of the absorbent core becomes very neat in appearance. Further, neat appearance as a whole body of a diaper is obtained, if combined with the leg opening edges that affect also on the neat appearance.

In addition, the elastic members may extend to an upper side portion of a leg opening initial end along the leg opening.

According to the above structure, the leg opening edges shrink by the elastic members, as shown by arrows in FIG. 40, the whole portion of the crotch region including the leg openings can be pulled upwards, to thereby improve the property of fitting to the physique of a wearing person.

The leg opening edges and ends of the elastic members which correspond to the leg opening edges may be fastened by heat seal.

In usual case, the elastic members are fastened by adhesives such as a hot-melt adhesive. In such a case, there is a possibility that the outside end of the elastic members may be drawn inside. However, according to the above-described manner, as shown in FIG. 37, when the outside end of the elastic members are fastened by heat-seal, such drawing in can be prevented.

Further, continuous leg section elastic members may be provided on the leg opening edges along the leg opening portions, and width of the leg opening edges projecting from the leg section elastic members may be within 5 mm.

According to the above-described structure, the ends of the leg opening edges shrink also in the leg surrounding direction, to thereby provide a paper diaper that makes leg opening edges hardly flutterable and makes portions around the legs neat and attractive by combined effect with the expand and contract elasticity of the leg opening edges toward the central portion of width direction.

In addition, in accordance with a seventh aspect of the invention, in the diaper, elastic members which shrink in the peripheral direction in a waist surrounding are arranged in a use surface side of a back side nonwoven fabric sheet which has an opacity of not less than 50% under JIS P 8138.

When the nonwoven fabric sheet has an of not less than 50% under JIS P 8138, existence of the elastic members is invisible or hardly visible. Consequently, a disposable diaper is provided so as to make a wearing person undaunted by anxiety about excessive tightening and formation of traces of rubber. Also, the invisible elastic members enable the high-class feeling of a product and good finish thereof which are appealing to a consumer.

In accordance with an eighth aspect of the invention, in the diaper, elastic members which shrink in the peripheral direction in a body peripheral region may be arranged in a use surface side of a back side nonwoven fabric sheet which has an opacity of not less than 40% under JIS P 8138, and a diameter of the elastic members is not more than 925 dtext.

According to such a structure, because the diameter of the elastic members is not more than 925 dtext, they are hardly visible from a long distance, and a wearing person is undaunted by anxiety about excessive tightening and formation of traces of rubber.

In addition, in accordance with a ninth aspect of the invention, in the diaper, a waist opening and a right and left leg openings may be formed in a use state, and a large number of elastic members which have a length extending at least from a waist opening edge to a leg opening initial end along the leg opening along a peripheral direction in a body peripheral region, and a large number of elastic members with spaces vertically may be arranged in a use surface side of a back side nonwoven fabric sheet which has an opacity of not less than 40% under JIS P 8138, and a diameter of the elastic members may be not more than 925 dtext and each of the spaces may be not more than 7.0 mm.

According to such a structure, because the diameter of the elastic members is not more than 925 dtext and each of the spaces is not more than 7.0 mm, not only above-described advantageous effects but also other advantageous effects which will be described hereafter are also obtained. That is, when the elastic members are small in diameter and arranged at small spaces, wrinkles generated become narrower in width in the peripheral direction as shown in FIG. 36(B), short in length in the longitudinal direction, and almost continuously generated in the longitudinal direction. Unevenness of each wrinkle is very small. There is almost no constriction in the thin rubber thread g portion, and when the color of the sheet and the color of the thin rubber thread g which constitutes external surface are the same (especially white), it is hard to distinguish existence of the thread rubber g.

Consequently, a disposable diaper having no wrinkles conspicuous, having fine wrinkles even if visible, and presenting a flat external surface, with sufficient fitting property and good in appearance without stuffy external surface can be produced. In addition, a disposable diaper with no formations of traces of rubber by being pressed to the skin on the face, avoiding too much pressure to the skin locally, and capable of improving the property of fitting to the physique of a wearing person with friction of the inner surface of the product and the skin extending the whole surface, to thereby prevent the product from Slipping down, can be produced.

In accordance with a tenth aspect of the invention, in the diaper, elastic members which shrink in the peripheral direction in a body peripheral region may be arranged in a use surface side of a back side nonwoven fabric sheet which has an opacity of not less than 40% under JIS P 8138, and a transparency of the elastic members may be not less than 50%.

When the transparency of the elastic members is not less than 50%, the existence of the elastic members are invisible or hardly visible Consequently, a wearing person is not undaunted by anxiety about excessive tightening and formation of traces of rubber. Also, the invisible elastic members enable the high-class feeling of a product and good finish thereof which are appealing to a consumer.

In accordance with an eleventh aspect of the invention, in the diaper, a waist opening and a right and left leg openings may be formed in a use state, and a large number of elastic members which have a length extending at least from a waist opening edge to a leg opening initial end along the leg opening along a peripheral direction in a body peripheral region, and a large number of elastic members with spaces vertically may be arranged in a use surface side of a back side nonwoven fabric sheet which has an opacity of not less than 40% under JIS P 8138, and a diameter of the elastic members may be not more than 925 dtext and each of the spaces may be not more than 7.0 mm, wherein at least in a front side, a region in which the elastic members having a diameter of not more than 620 dtext are attached to the back side nonwoven fabric sheet with a space of not more than 7.0 mm, may exist over a length range not less than 60% of a length of the body peripheral region.

In the above-described diaper, because in the length range extending from the waist opening edge to the leg opening initial end, the elastic members that exist over 60% or more of the length range of the body peripheral region, have a diameter of not more than 620 dtext, and the space between the elastic members is not more than 7.0 mm.

Thereby, a disposable diaper excellent in appearance with no conspicuous wrinkles, having a neat appearance, that is, having no stuffy external surface with fine wrinkles even if wrinkles are generated, and presenting a flat face on the whole is produced.

In the paper diaper according to the seventh to eleventh aspects of the invention, preferably, an extension magnification of the elastic members is in a range of 150-350%

According to a paper diaper with the numerical range limited as described above, the property of fitting is not spoiled and generation of wrinkles is not conspicuous.

Further, an elastic member may be interposed between a back side nonwoven fabric sheet and a use side nonwoven fabric of the same color facing thereto.

Accordingly, the elastic member can be hardly visible due to the existence of both nonwoven fabrics.

The back side nonwoven fabric sheet may be not more than 40 g/m$^2$, not less than 0.1 mm in thickness, and not less than 10 mm in rigidity defined by JIS P 8143.

By having the diameter of 0.1 mm or more, high screening property of the elastic members is obtained, and by having rigidity of 10 mm or more, excellent elasticity and texture are obtained.

BRIEF DESCRIPTION OF THE DRAWINGS

FIG. 10(A) is a horizontal flow type system view, and FIG. 10(B) is a vertical flow type system view.

FIG. 29(A) to FIG. 29(E) are views showing arrangement patterns of a leg section elastic members of the external sheet 420.

FIG. 80(A) and FIG. 80(B) are views showing an example of a conventional pant-type of disposable diaper, wherein

FIG. 81(A) and FIG. 81(B) are views of an example of a pant-type of disposable diaper according to an earlier development by the applicant, wherein

PREFERRED EMBODIMENT OF THE INVENTION

Preferred embodiment of the invention will be explained with reference to the drawings, as follows.

First Embodiment

Figure 1:
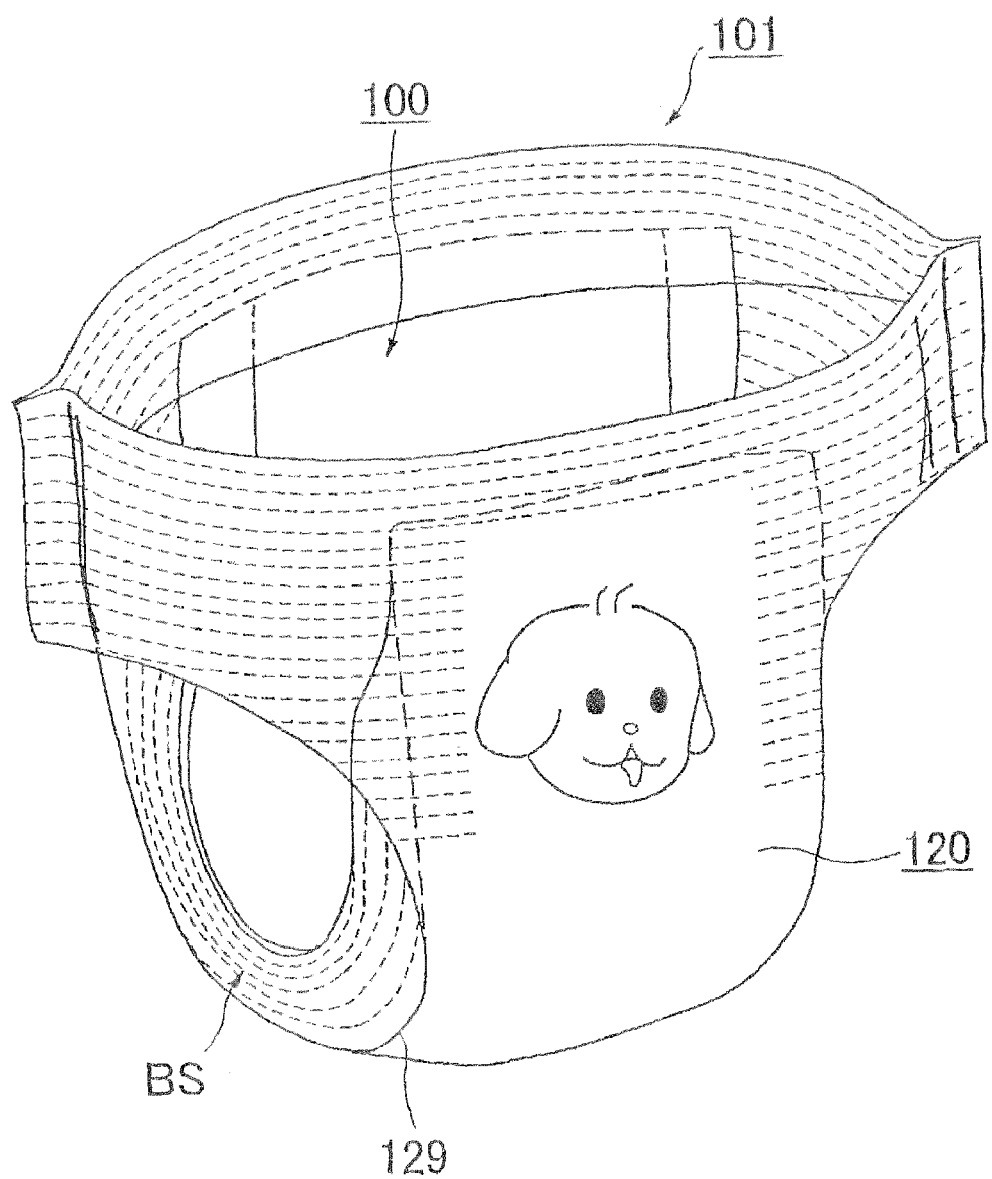
FIG. 1 is a perspective view of a product state of pant-type of disposable diaper 101 according to the first embodiment of the invention.
Figure 2:
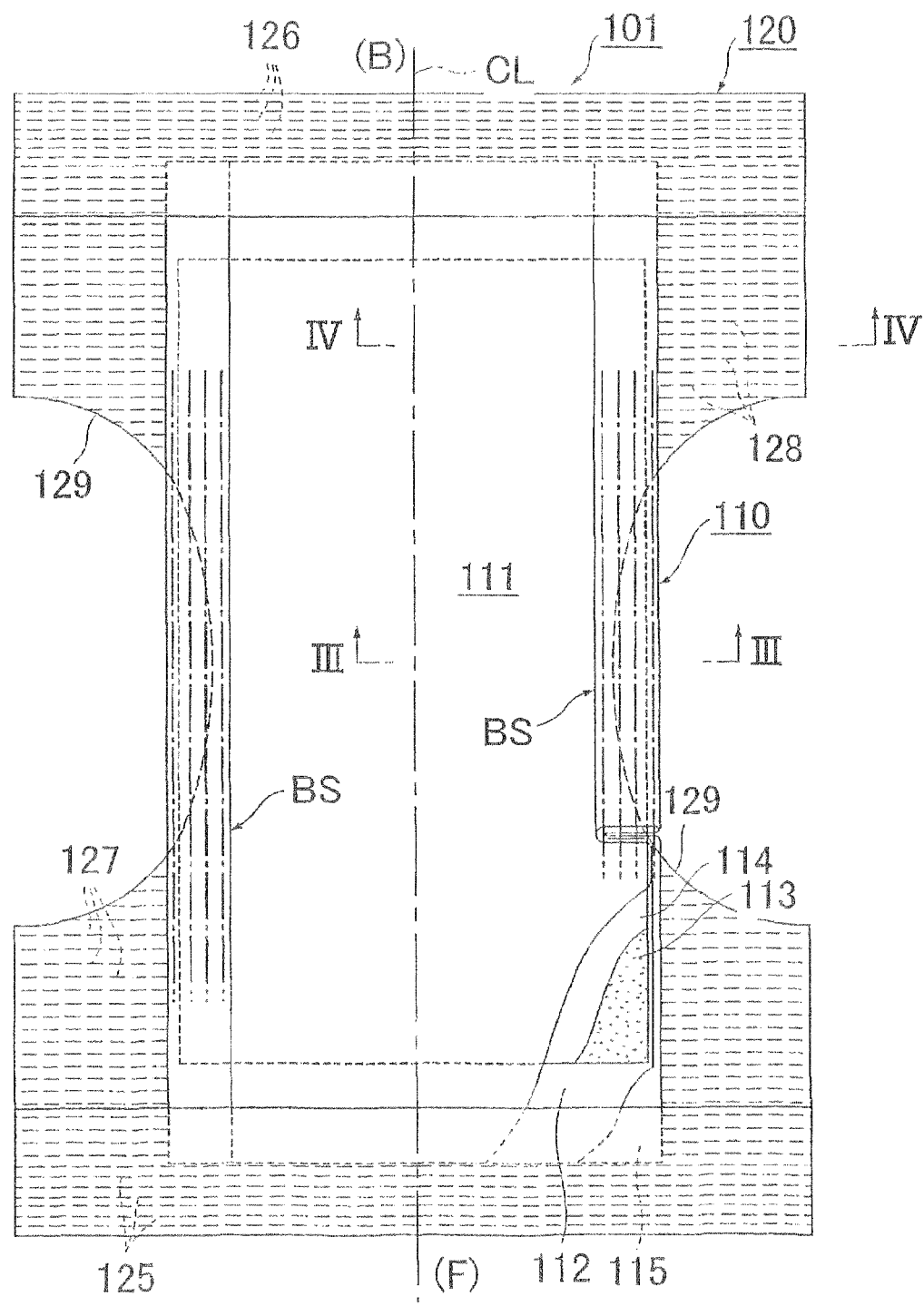
FIG. 2 is a development thereof.
Figure 3:
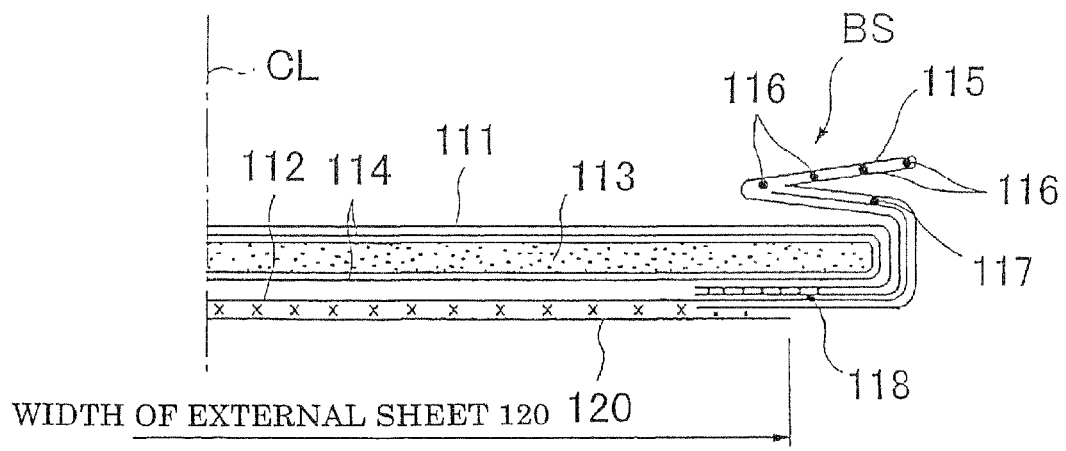
FIG. 3 is a sectional view taken along the line III-III of FIG. 2.
Figure 4:
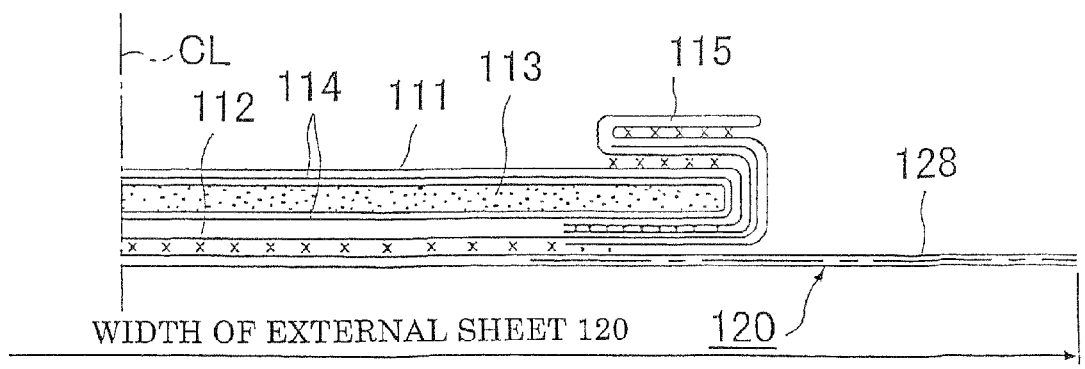
FIG. 4 is a sectional view taken along the line IV-IV of FIG. 2.

FIG. 1 is a perspective view of a product state of pant-type of disposable diaper 101 according to the first embodiment of the invention; FIG. 2 is a development thereof; FIG. 3 is a sectional view taken along the line of FIG. 2; and FIG. 4 is a sectional view taken along the line IV-IV of FIG. 2. In the drawings, the fastening portions are specified by marks "x".

As shown in the figures, the disposable diaper 101 of the invention (which may be referred to as a paper diaper simply, hereafter) has: a paper diaper main body 110 including a structure which has a liquid-permeable top sheet 111 composed of mainly nonwoven fabric or the like, a leakage preventing sheet 112 composed of polyethylene or the like, and an absorbent body 113 such as a cottony pulp interposed between them; and an external sheet 120 integrally disposed on the outside of the diaper main body 110.

Hereafter, the structure of the main body 110 of the disposable diaper and the external sheet 120, and the assembling structure thereof and a manufacturing method therefor will be explained in order.

(Structure of Main Body 110 of Paper Diaper)

In an embodiment shown in the figures, as the absorbent body 113, one formed to have an approximately rectangular plan shape is used, and its width size is set to be soft to a crotch portion so that a wearer may not feel stiffening. The absorbent body 113 is wrapped by a crepe paper 114 for the sake of retention of the body fluid and improving diffusion of body fluid that permeates liquid-permeable top sheet 111. It is preferable to use an air-laying absorbent body capable of reducing a bulk, as the absorbent body 113.

As liquid-permeable top sheet 111 which covers the surface side (skin contact side) of the absorbent body 113, porous or poreless nonwoven fabric, a porous plastic sheet or the like are preferably used.

As a material fiber that constitutes the nonwoven fabric, olefins series such as polyethylene or polypropylene, synthetic fibers such as polyester series and polyamide series, in addition, regenerated fibers such as rayon and cupra, natural fibers such as cotton, or the like can be used. A method for feeding the fiber includes a spun lace method, a spun bond method, a thermal bonding method, a melt blow method, and a needle punch method, or the like. These methods are suitably used to obtain a nonwoven fabric. In these processing methods, the spun lace method is excellent in flexibility and drape ability, and the thermal bonding method is excellent in bulkiness and soft feature. When a plurality of through holes are formed on the liquid-permeable top sheet 111, urine is absorbed promptly, presenting an excellent dry-to-the touch feature. The liquid-permeable top sheet 111 extends to the back side of the absorbent body 113, wrapping the side edges of the absorbent body 113.

As for leakage preventing sheet 112 that covers the back side (non-skin contact side) of the absorbent body 113, non-permeable plastic sheets, such as polyethylene, polypropylene or the like, are used. However, in recent years, permeability is preferred in order to prevent effectively the skin from steaming. The water-cut and liquid permeable top sheet serves as a fine porous sheet obtained in such a way that an inorganic filler is melt-kneaded to olefin resin such as polyethylene and polypropylene or the like, then extended in uniaxial direction or biaxial directions. If having the same sheet size, the rigidity falls rather than a poreless sheet, therefore the porous sheet is more excellent in respect of flexibility than a poreless sheet.

On the other hand, gather nonwoven fabrics 115 forming three-dimensional gathers BS, as shown in FIG. 3 and FIG. 4, use a nonwoven fabric that is two-folded to be a double sheet. Side edges of the absorbent body 113 that is wrapped by the liquid-permeable sheet 111 are wrapped thereon by the nonwoven fabric, which extends to the back side of the absorbent body 113 to be integrally bonded. More specifically, the gather nonwoven fabrics 115 are bonded by a hot-melt adhesive in a range from the center to the back side of the absorbent body 113, excepting the three-dimensional gathers BS formation portion in the center of the longitudinal direction of the paper diaper shown in FIG. 3. In addition, as shown in FIG. 4, between both side edges of the longitudinal direction, the gather nonwoven fabrics 115 are bonded by a hot-melt adhesive or the like in the center of the width direction of a paper diaper extending to one of the edges, which extends to the back side of the absorbent body 113, so as to fold up the portion that forms the three dimensional gathers BS on the upper surface portion of the absorbent body 113.

In the inside of the gather nonwoven fabric 115 formed of the double sheet nonwoven fabric, a plurality of thread-shaped elastic members 116, 116 . . . are arranged in raised ends. In addition, thread-shaped elastic members 117 are arranged in the vicinity of the side edge portion of the absorbent body 13, and further thread-shaped elastic members 118 are arranged in the side portion of the back side of the absorbent body 113, respectively. The elastic members of the raised ends 116, 116 . . . are for forming the three-dimensional gathers BS by raising the nonwoven fabric portion protruded from the absorbent body side edge portion, by its expansion and contraction force. The thread-shaped elastic members 117 and 118 cause the side edges of the absorbent body 113 to be banded by its expansion and contraction force, thereby constituting a base end portion of the three-dimensional gathers BS by the side edge portion of the absorbent body 113, as shown in a product state of FIG. 5. The raising height HL of the absorbent body 113 from the bent portion to the absorbent body side edges is 5 to 30 mm, preferably 20 to 30 mm. When the raised height HL is less than 5 mm, it becomes too short to obtain a bending state of the side edges of the absorbent body. Also sufficient fitting property to the skin is not obtained. Moreover, if the raised height HL exceeds 30 mm, raised length becomes too long to effectively obtain a bending state.

Figure 5:
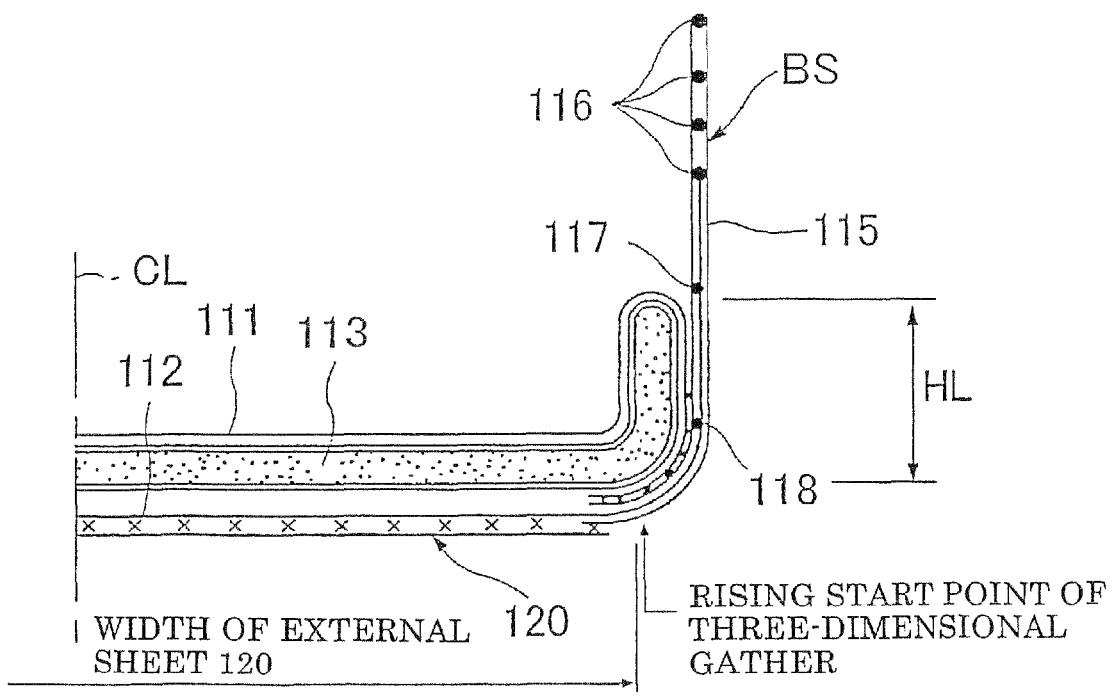
FIG. 5 is a sectional view in a product state shown taken along the line of FIG. 2.

The leakage preventing sheet 112 extends to the inside of gather nonwoven fabric 115, which is formed in double layer sheet structure, to constitute a leakage preventing wall on lower end side of the three-dimensional gathers BS, as shown in FIG. 5. It is preferable to use an opaque sheet as the leakage preventing sheet 112, so that brown, which is the color of excretion, may not be visible from the outside. Pigments such as calcium carbonate, titanium oxide, zinc oxide, white carbon, clay, talc, sulfuric acid barium or the like, or fillers added to the plastic to make opaque film, are preferably used.

The thread-shaped elastic members 116 to 118 are composed of materials such as styrene series rubber usually used, olefin series rubber, urethane series rubber, ester series rubber, polyurethane, polyethylene, polystyrene, styrene butadiene, silicon, polyester or the like. Moreover, in order to make it hard to be visible from an outer side, it is preferable to set to 925 dtex or less in diameter, 150 to 350% in tension, and 7.0 mm or less in spaces therebetween. In addition, the thread-shaped elastic members can be replaced with tape-like stretchable members having a certain amount of width.

As a material fiber that constitutes the gather nonwoven fabrics 115, olefins series such as polyethylene or polypropylene, synthetic fibers such as polyester series, polyamide series or the like, in addition, regenerated fibers such as rayon, cupra or the like, and natural fibers such as cotton can be used, similarly to the liquid-permeable top sheet 111. A method for feeding the fiber includes a spun lace method, a spun bond method, a thermal bonding method, a melt blow method, and a needle punch method, or the like. These methods are suitably used to obtain the nonwoven fabric. In order to prevent effectively the skin from steaming especially, the nonwoven fabric that reduces a basis weight and excellent in air permeability is preferably used. Furthermore, as for the gather nonwoven fabrics 115, water repellent treated nonwoven fabric coated with a paraffin metal series and alkyl chromic chloride series or the like is preferably used, in order to prevent sweating and rash while preventing the oozing out of body fluid and the like from the absorbent body, thereby improving a dry-to-the-touch feature to the skin.

(Structure of External Sheet 120)

External sheet 120 is made of a nonwoven fabric sheet. In the nonwoven fabric, at least arrangement region of the elastic members is formed in a double layer sheet structure. In the embodiment shown in the figures, the external sheet only the front side section F and the back side section B are formed in a double layer sheet structure. On the other hand, a crotch region is formed in a single layer sheet structure. Of course, the nonwoven fabric for internal surface and the nonwoven fabric for external surface may be a two-layers sheet structure by laminating using a hot-melt adhesive. Leg cut-out portions 129 that form leg openings are provided in the center, therefore a nearly hourglass form is accomplished as a whole.

Figure 6:
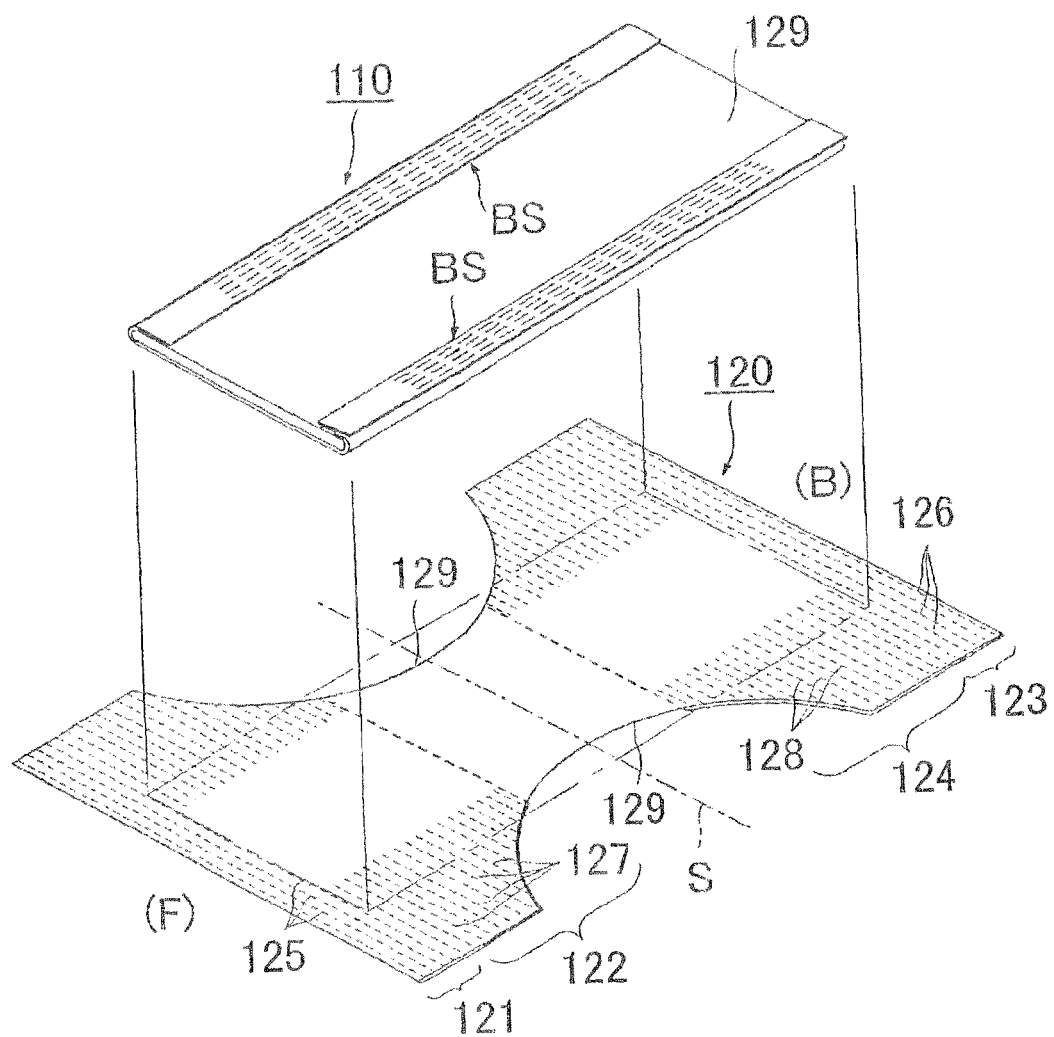
FIG. 6 is an assembly view of main body portion 110 of a paper diaper, and external sheet 120.

Specifically, in an development form as shown in FIG. 6, in the region of the waist portions 121, 123 of front side section F and back side section B, a plurality of waist-section elastic members 125 . . . , and 126 . . . , composed of thin rubber threads, for example, are respectively, provided over the full width.

Also, in the region of the under waist portions 122, 124 of front side section F and back side section B, waist section elastic members 127 . . . , and 128 . . . are arranged along the width direction in both sides region only, except the center. And no elastic members exist along the leg-surrounding portions.

In a paper disposable diaper of the invention, the leg cut-out portions 129, and 129 in the crotch region is very important, in order to obtain a neat appearance in the leg-surrounding portions. As shown by wave line in FIG. 6, and as clarified by the relative arrangement region of paper diaper main body 110, the leg cut-out portion of the external sheet 120 forming the leg openings is positioned nearer to the central portion than the side edges of the paper diaper main body 110. Also, as shown in FIG. 5 and FIG. 1, in a minimum width region of crotch portion of the paper diaper in a product state, the leg cut-out portions 129 and 129 are positioned in the vicinity of rising start points of the three-dimensional gathers BS.

Figure 7:
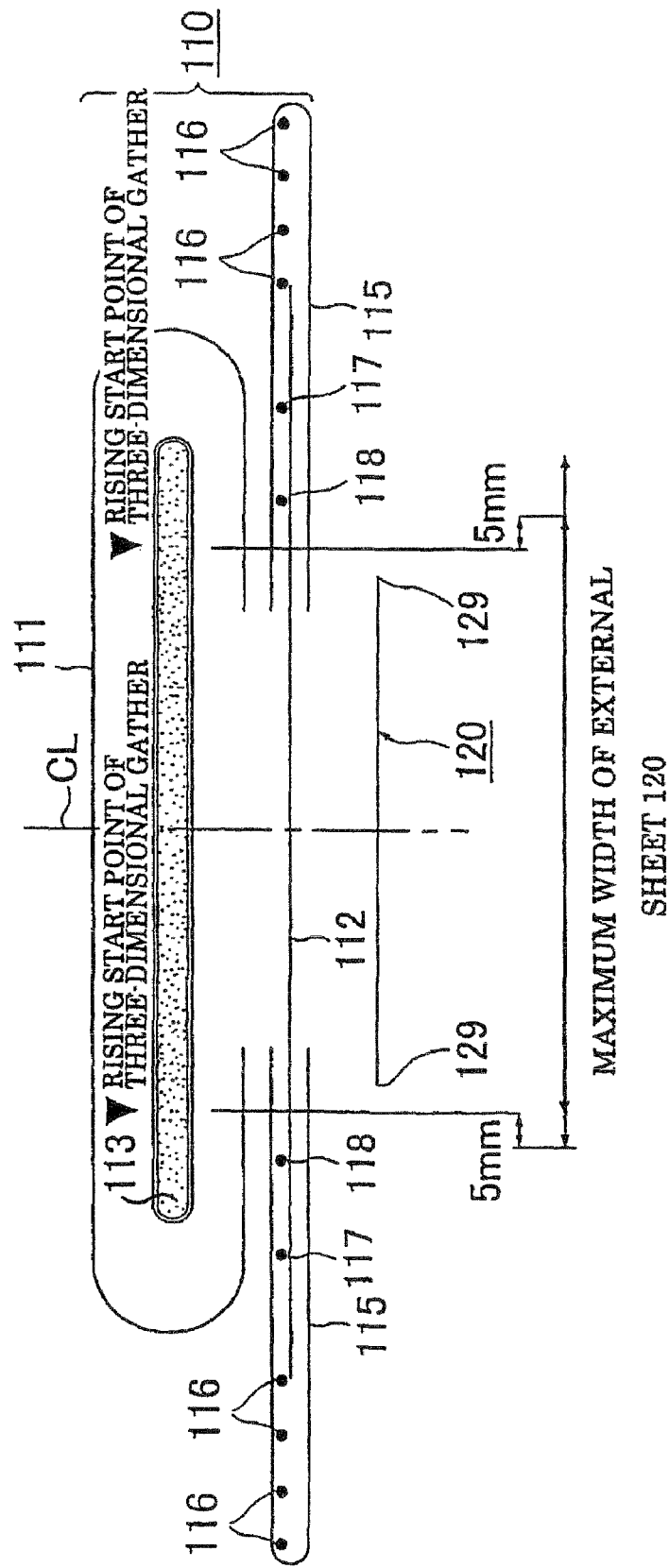
FIG. 7 is an exploded sectional view of a paper diaper in a crotch portion.

The leg cut-out line of such an external sheet 120 shows one aspect of the invention, and in the invention, in the minimum width region of crotch portion of a paper diaper, the leg cut-out portion 129 may be positioned nearer to the center than places outward by 5 mm from the rising start point of the three-dimensional gathers. FIG. 7 is an exploded sectional view of the crotch portion of the paper diaper. If put in another way, the width of the external sheet 120 may be within a range outward by 5 mm from the rising start points of the absorbent body 113 respectively shown by ▼ mark.

(Assembly of a Paper Diaper)

As shown in FIG. 6, the paper diaper main body 110 and the external sheet 120 are integrated by bonding the paper diaper main body 110 onto the upper surface of the external sheet 120 through hot-melt adhesive or the like. A pant-type of disposable diaper is assembled by folding up a paper diaper main body 110 and the external sheet 120 so as to overlap the front side and the back side with a lengthwise directional center as a fold line S, and by thermally welding or by using hot-melt adhesive, to join both side edges thereof.

Figure 8:
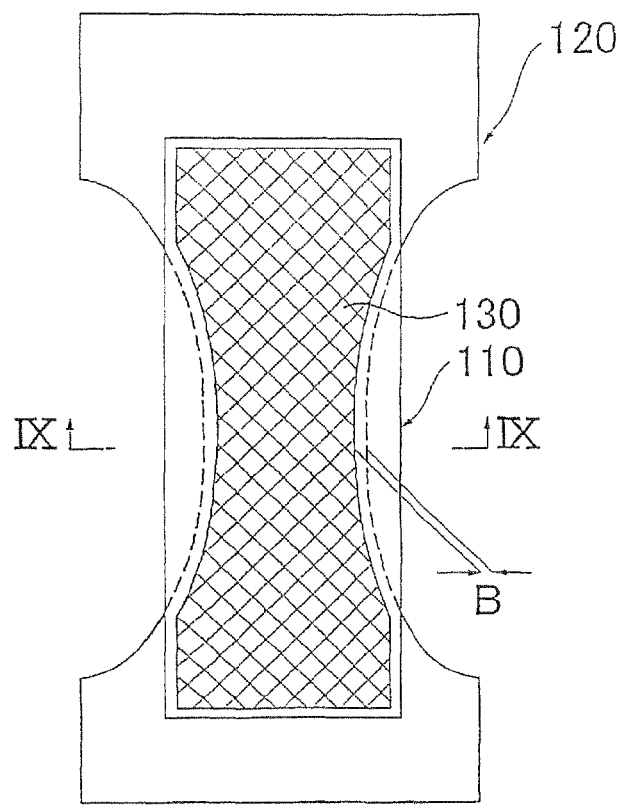
FIG. 8 is a view showing a bonding region of the main body portion 110 and external sheet 120, of a disposable diaper.
Figure 9:
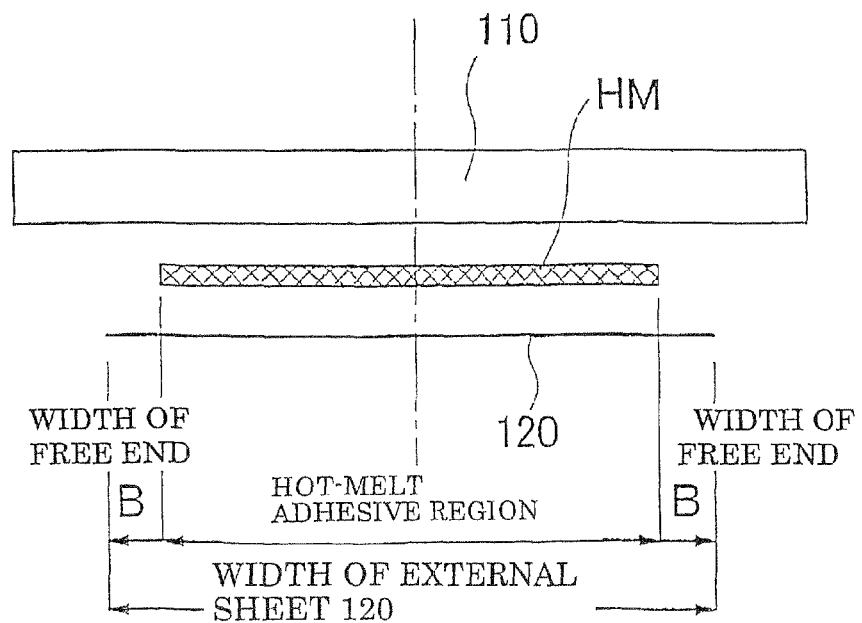
FIG. 9 is an exploded sectional view taken along the line IX-IX of FIG. 8.

The paper diaper main body 110 and the external sheet 120 are bonded by a hot-melt adhesive HM in a mode of complete bonded state mostly. Hot-melt bonding region 130 is shown by intersecting slash in FIGS. 8 and 9. However, width B of the non-bonded portions (free ends) of the side edges along the leg cut-out line of the external sheet 120 is preferably 15 mm or less, more preferably 10 mm or less. To provide a paper diaper that has a neat appearance of leg surrounding portions, it is preferable to remove a non-bonded portion and set free ends width B to 0. However, even when a certain amount of non-bonded portion needs to be formed in the outer edges of the external sheet 120 according to the restrictions of a hot-melt application device, the maximum width is preferably not more than 15 mm. Moreover, the ratio of the free width B [(free width B×2)/width of external sheet 120] in the width direction is preferably 20% or less. According to the above-described structure, the side edges of the external sheet 120 are not flutterable and makes portions around the legs neat and attractive.

Figure 10A:
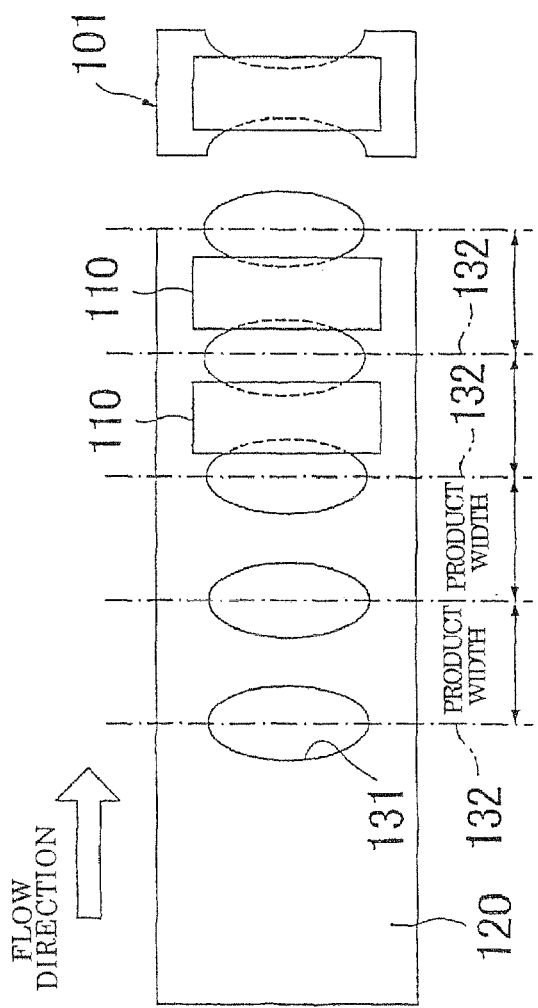
FIGS. 10(A) and 10(B) are views showing an assembling process of the paper diaper.
Figure 10B:
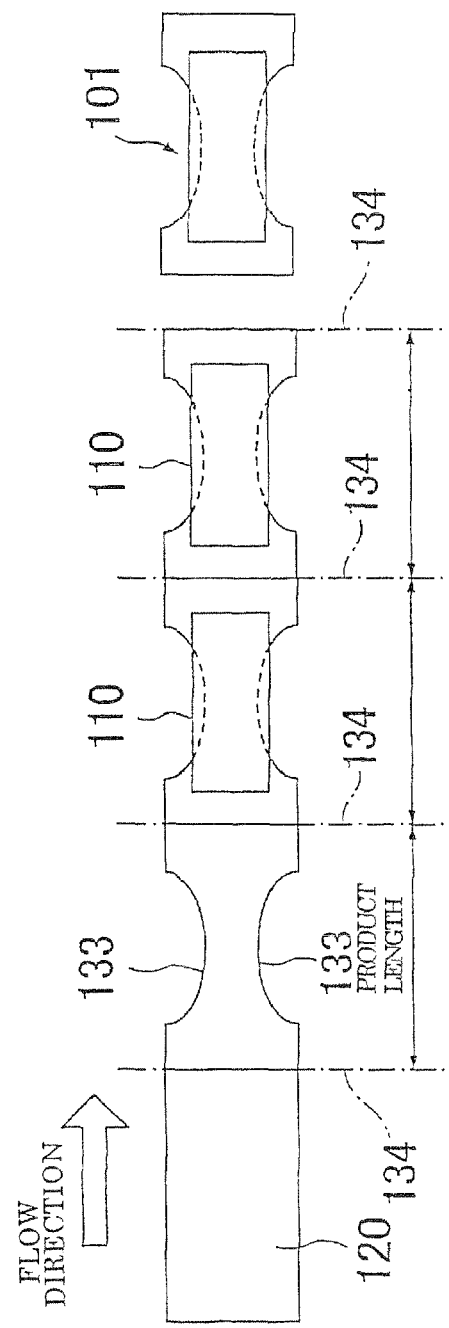

By the way, in the paper diaper of the invention, the crotch width of the paper diaper main body 110 is larger than the crotch width of the external sheet 120. Therefore, it is not possible to cut the leg cut-out portions from each external sheet 120 after laminating the paper diaper main body 110 on the continuous web of the external sheet 120 at predetermined intervals in a flow direction. Then, as shown in FIG. 10(A) and FIG. 10(B), the paper diaper is manufactured in such a way that after cutting the leg portion over the continuous web of the external sheet 120, the paper diaper 110 is laminated thereon. FIG. 10(A) is an assembling process of this paper diaper by a horizontal flow system view, wherein direction of a line corresponds to the paper diaper width direction. During the step of supplying the continuous web of the external sheet 120, the crotch portions are cut along the ellipse-like leg cut-out lines 131 by a roll cutter or the like. Thereafter, paper diaper main bodies 110 are laminated on the crotch sections through a hot-melt adhesive so as to straddle the ellipse-like cut-out portions a little, and then the external sheet 120 is cut at the edge positions 132 of product width between the paper diaper main body 110 and 110. FIG. 10(B) is an assembling process of this paper diaper by a vertical flow system view, wherein direction of a line corresponds to the paper diaper longitudinal direction. During the step supplying the continuous web of the external sheet 120, the crotch portions are out in a half of ellipse-shape along the leg cut-out lines 133. Thereafter, paper diaper main bodies 110 are laminated on the crotch sections through a hot-melt adhesive and then the external sheet 120 is cut at the edge positions 134 of product length between the paper diaper main body 110 and 110.

Figure 11:
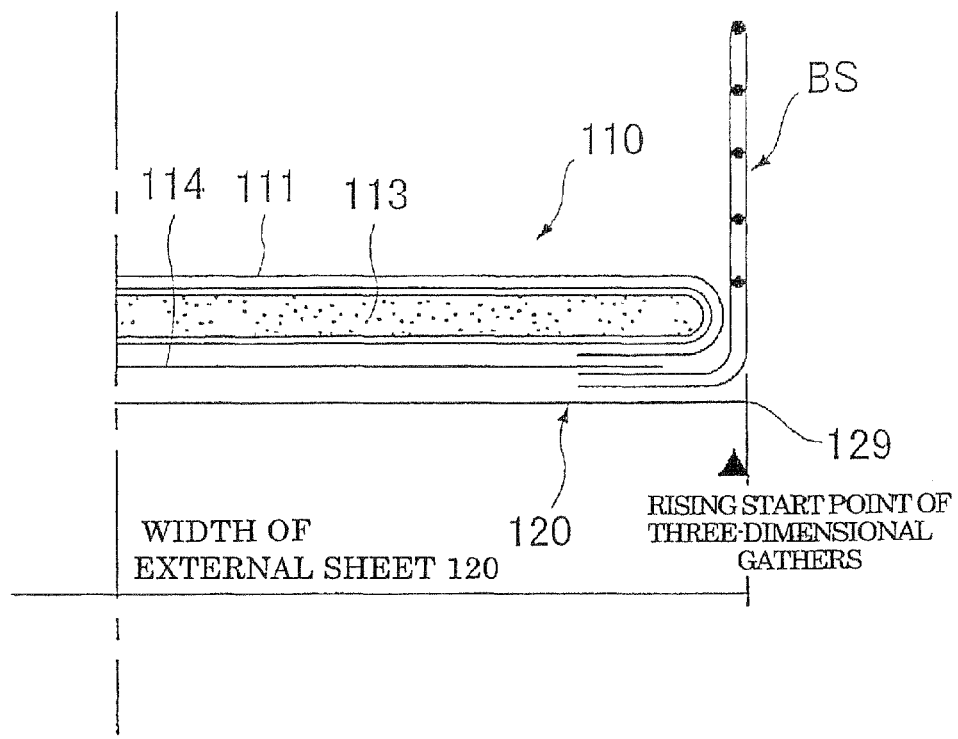
FIG. 11 is a view showing another embodiment of a leg cut-out portion of the external sheet 120 of the invention.

The above-described paper diaper presents an example in which both ends of the absorbent body 113 are raised in the longitudinal direction to form the three-dimensional gathers BS. However, in case of the paper diaper structure shown in FIG. 11 which constitutes the three dimensional gathers BS only from a gather nonwoven fabric 115 like many paper diapers marketed, the leg cut-out portions 129 of the external sheet 120 forming leg openings are positioned nearer to the center than places outward by 5 mm from rising start points of the three-dimensional gathers BS.

Second Embodiment

In the first embodiment, the leg cut-out portion of the external sheet 120 is determined with respect to the rising start points of the three-dimensional gathers BS. However, neat appearance in the leg-surrounding portions can be achieved by determining the leg cut-out portion with respect to the absorbent body 113. That is, in a minimum width area of the crotch portion of the disposable diaper, leg cut-out portions of the external sheet 120 forming leg openings are positioned nearer to the center than places outward by 5 mm from side edges of the absorbent body 113, to thereby achieve neat appearance in the leg-surrounding portions.

Figure 12:
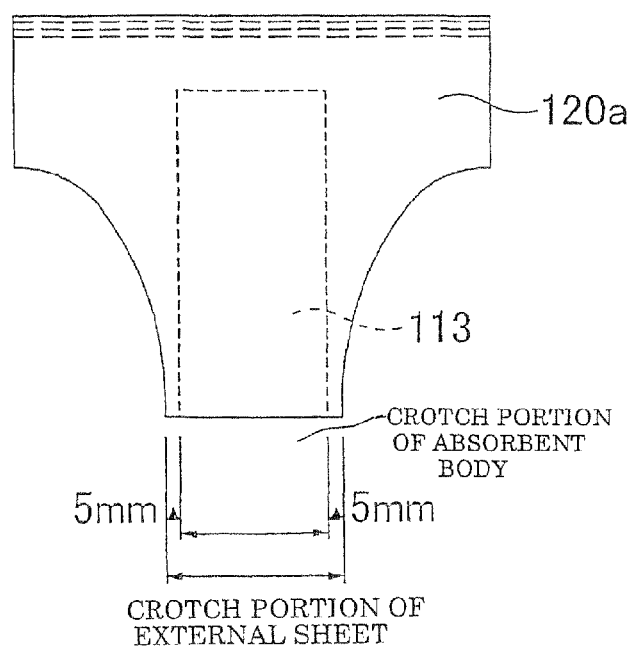
FIG. 12 shows a disposable diaper according to the second embodiment of the invention, and is a front view showing the leg cut-out portion of the external sheet 120a defined by a relative position with absorbent body 113.

Detailed structure of the paper diaper is already explained, omitting further explanation. FIG. 12 is a view showing the case where the crotch width of the external sheet 120*a* is made the maximum with respect to the absorbent body 113. That is, in the embodiment, the leg cut-out portion 129 of the external sheet 120*a* is positioned at places outward by 5 mm form both sides end of the crotch width of the absorbent body 113.

Figure 13:
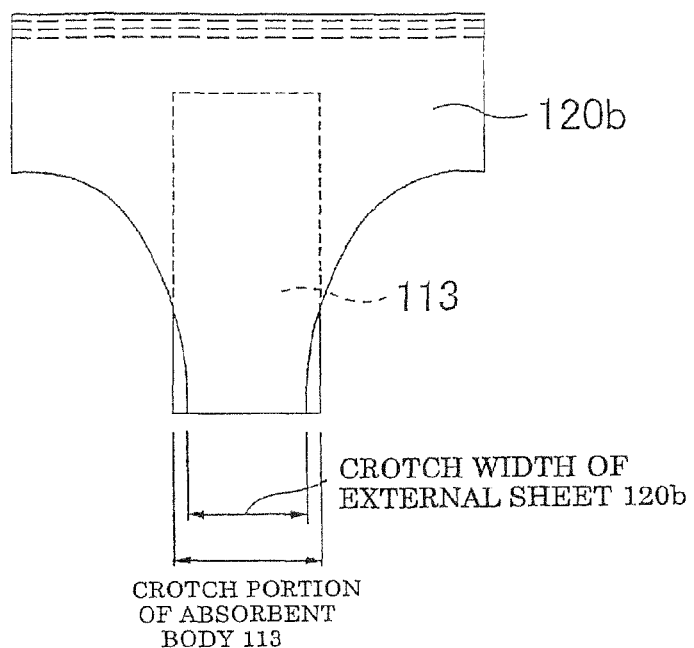
FIG. 13 is a front view showing another embodiment of the leg cut-out portion of the external-sheet 120b defined by a relative position with absorbent body 113.

Moreover, FIG. 13 is a view showing the case where the crotch width of the external sheet 120*b* is made narrower than the crotch width of the absorbent body 113. The absorbent body 113 becomes more protruded than the external sheet 120*b*. However, frills are removed, thereby to present a neat appearance of leg surrounding portions.

In addition, the absorbent body side edge that defines the leg cut-out portion of the external sheet means the side edge of the absorbent body itself including no crepe papers 114.

Other Embodiment

Figure 14:
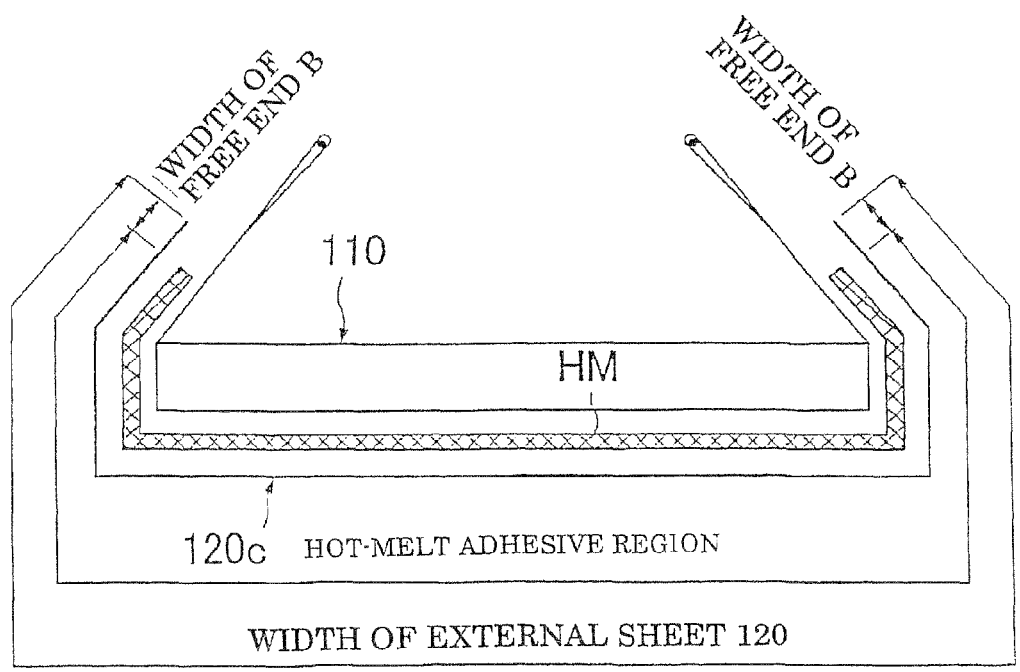
FIG. 14 is a vertically sectional view showing a bonded state of the external sheet 120 of the disposable diaper according to the third embodiment of the invention.

When the paper diaper main body 10 is bonded to the external sheet 20, width of a non-bonded side edges along the leg cut-out line of the crotch portion of the external sheet that is integrally bonded by adhesion is 15 mm or less. This structure is preferably combined with the first embodiment or the second embodiment. However, in order to obtain a neat appearance of leg surrounding portions, it may be adopted as independent structure. FIG. 14 is a schematic view of the disposable diaper according to the third embodiment of the invention shown in vertical section, wherein the leg cut-out portion 129 of the external sheet 120*c* is extended to the side edges of three-dimensional gathers BS. The size of the free edge B is set to 15 mm or less, to thereby remove flutter and provide a neat appearance.

Modifications

Figure 15A:
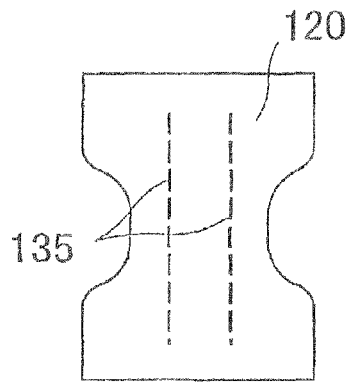
FIG. 15(A) to FIG. 15(E) are views showing embodiments of an arrangement pattern of leg surrounding section elastic members of the external sheet.
Figure 15B:
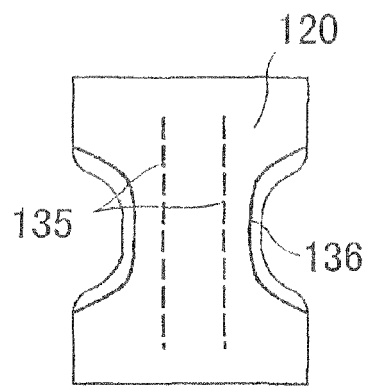
Figure 15C:
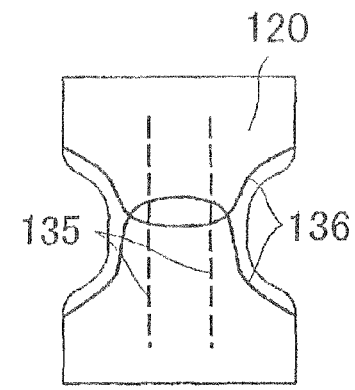
Figure 15D:
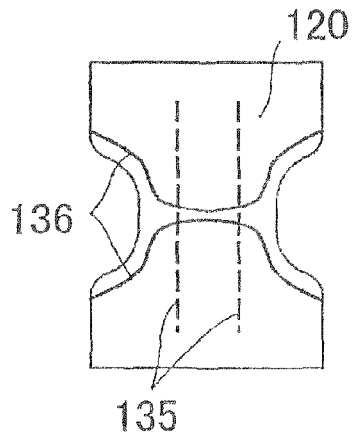
Figure 15E:
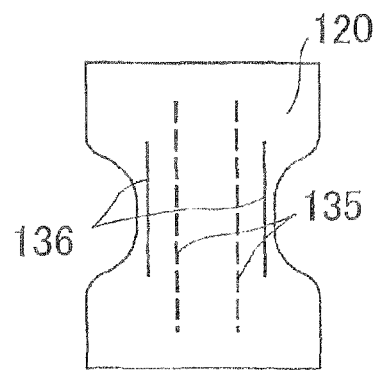

By the way, arrangement mode of the elastic members arranged over the external sheet 120 is arbitrary. FIG. 15(A) to FIG. 15(E) are views showing the arrangement pattern. FIG. 15(A) shows an example in which two lines of elastic members 135, 135 for raising the absorbent body, are arranged in the longitudinal direction of the paper diaper. FIG. 15(B) shows an example in which two lines of elastic members 135, 135 for raising the absorbent body are arranged and leg section elastic members 136, 136 are also arranged on whole peripheries of the leg surrounding portions. FIG. 15(C) shows an arrangement of leg section elastic members 136 arranged in a crossing manner at the crotch portion. FIG. 15(D) shows an arrangement of leg section elastic members 136 arranged in parallel in the crotch portion. FIG. 15(E) shows an arrangement of leg section elastic members 136 arranged along the longitudinal direction of the paper diaper.

Figure 16A:
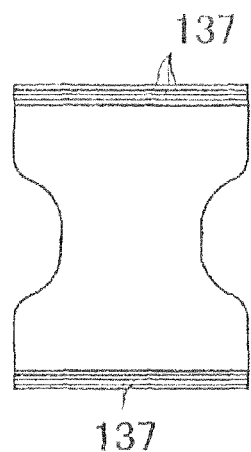
FIG. 16(A) to FIG. 16(E) are views showing embodiments of arrangement patterns of waist openings and waist surrounding elastic members of the external sheet.
Figure 16B:
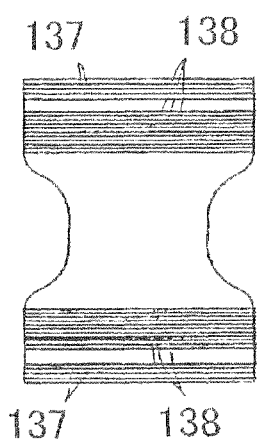
Figure 16C:
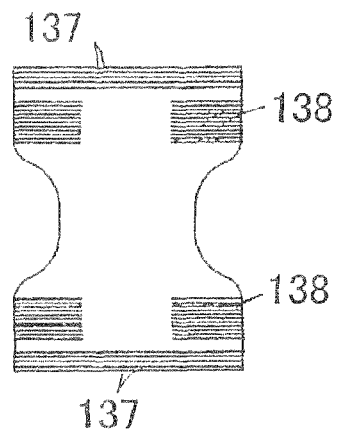
Figure 16D:
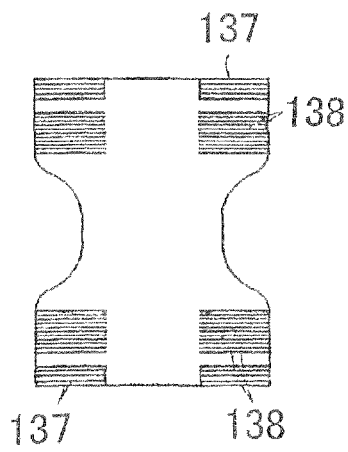
Figure 16E:
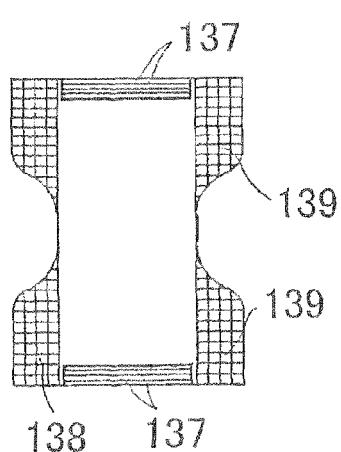

Also, the arrangement mode of the waist section elastic members and the under waist section elastic members are similarly arbitrary. FIG. 16(A) to FIG. 16(E) are views showing the arrangement pattern, wherein FIG. 16(A) shows an arrangement of the waist-section elastic members 137 only, and FIG. 16(B) shows an arrangement of the waist section elastic members 137 and the under waist section elastic members 138, extending on the whole width. FIG. 16(C) shows an arrangement of the waist-section elastic members 137 extending on the whole width and of the under waist section elastic members 138 at both sides only, excepting a central section. FIG. 16(D) shows an arrangement of the waist-section elastic members 137 and the under waist section elastic members 138 at both sides only, excepting a central section. FIG. 16(E) shows an arrangement of side sheets 139 composed of another elastic material which are attached to the body side portion.

As described above, the pant-type of paper diaper was taken for the example for explaining the invention. However, the invention is completely applicable similarly to a tape fastening type of paper diaper.

As explained in detail above, these embodiments provide a paper diaper which makes leg opening edges with no frills and hardly flutterable and makes portions around the legs neat and attractive. In addition, problems, such as itchy rash or stiffening feeling when wearing trousers thereon, due to contact of the frill to the skin can be solved.

Fourth Embodiment

Figure 17:
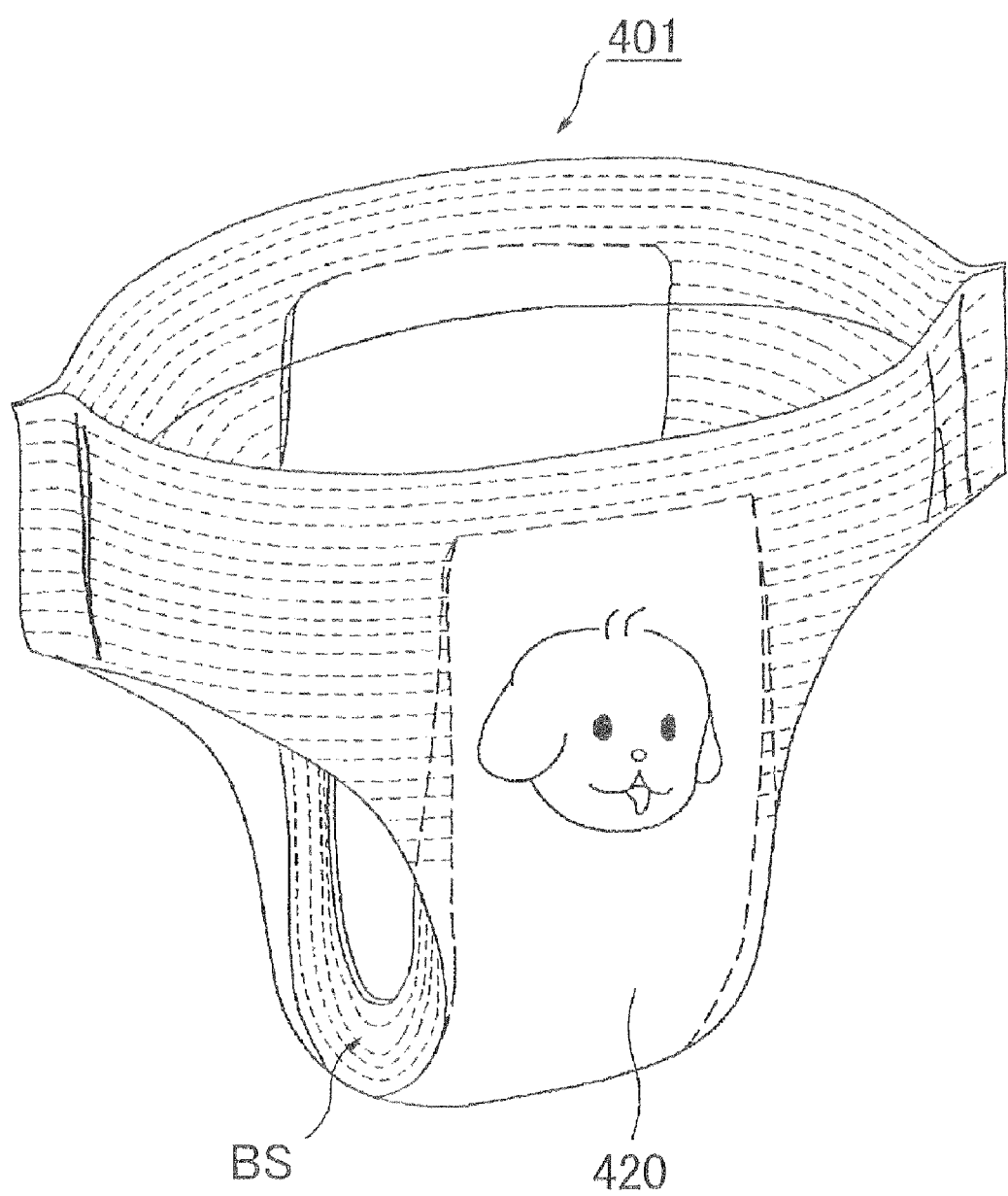
FIG. 17 is a perspective view of a product state of a pant-type of disposable diaper according to the fourth embodiment of the invention.
Figure 18:
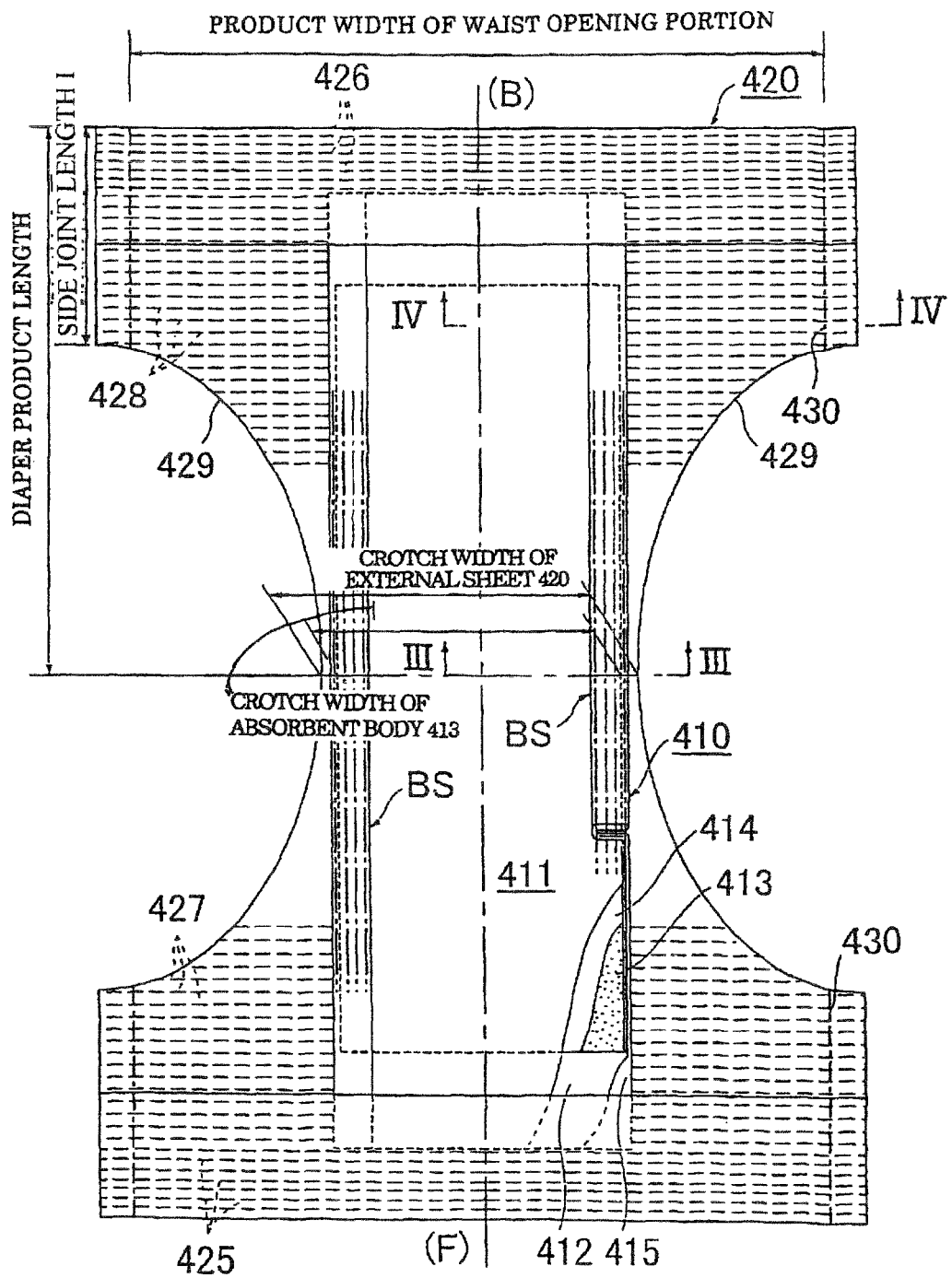
FIG. 18 is the development view thereof.
Figure 19:
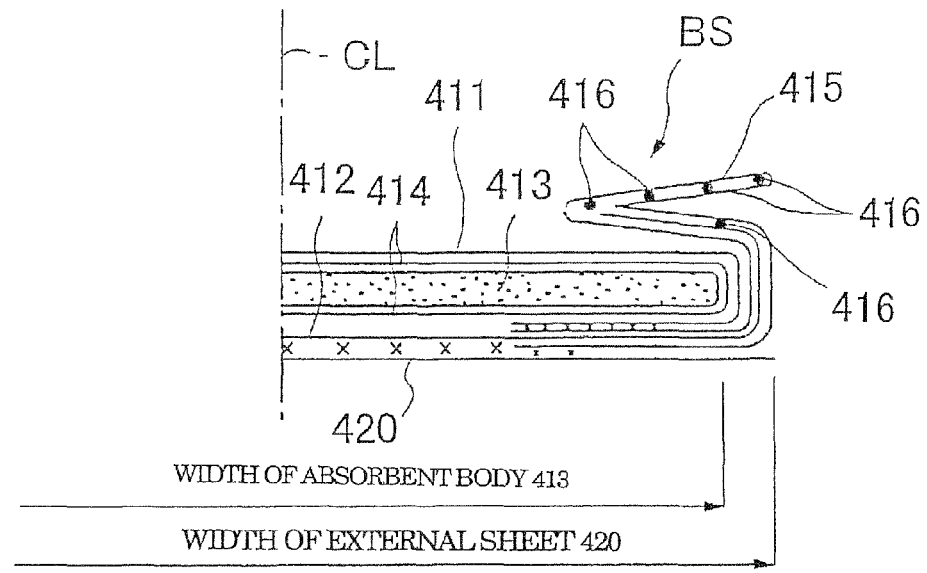
FIG. 19 is a sectional view taken along the line III-III of FIG. 18.
Figure 20:
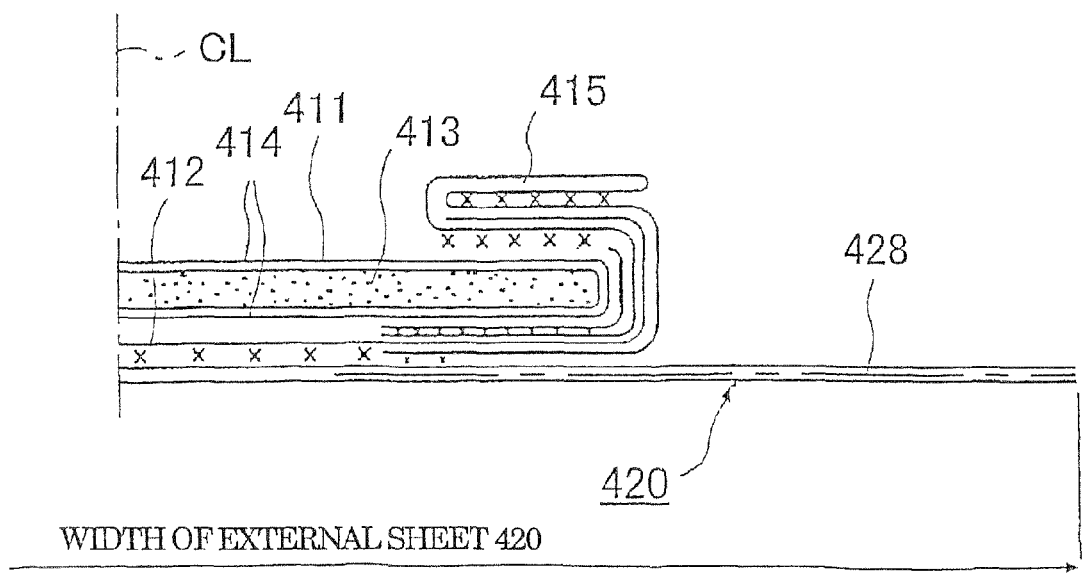
FIG. 20 is a sectional view taken along the line IV-IV of FIG. 18.

FIG. 17 is a perspective view of a product state of pant-type of disposable diaper 401 according to a fourth embodiment of the invention. FIG. 18 is its development view, FIG. 19 is a sectional view taken along the line III-III of FIG. 18 showing a development state, and FIG. 20 is a sectional view of FIG. 18 shown by an arrow taken along the line IV-IV. Incidentally, in the necessary portion of a drawing, the bonded portion is specified by marks "x".

As shown in the figures, the disposable diaper 401 of the invention (which may be referred to as a paper diaper simply, hereafter) has: a paper diaper main body 410 including a structure which has a liquid-permeable top sheet 411 composed of mainly nonwoven fabric or the like, a leakage preventing sheet 412 composed of polyethylene or the like, and an absorbent body 413 such as a cottony pulp interposed between them; and an external sheet 420 integrally disposed on the outside of the diaper main body 410.

Hereafter, the structure of the main body 410 of the disposable diaper and the external sheet 420, and the assembling structure thereof and a manufacturing method therefor will be explained in order.

(Structure of Main Body 410 of Paper Diaper)

In an embodiment shown in the figures, as the absorbent body 413, one formed to have an approximately rectangular plan shape is used, and its width size is set to be soft to a crotch portion so that a wearer may not feel stiffening. The absorbent body 413 is wrapped by a crepe paper 414 for the sake of retention of the body fluid and improving diffusion of body fluid that permeates liquid-permeable top sheet 411. It is preferable to use an air-laying absorbent body capable of reducing a bulk, as the absorbent body 413.

As liquid-permeable top sheet 411 which covers the surface side (skin contact side) of the absorbent body 413, porous or pore less nonwoven fabric, a porous plastic sheet or the like are preferably used. As a material fiber that constitutes the nonwoven fabric, olefins series such as polyethylene or polypropylene, synthetic fibers such as polyester series and polyamide series, in addition, regenerated fibers such as rayon and cupra, natural fibers such as cotton, or the like can be used. A method for feeding the fiber includes a spun lace method, a spun bond method, a thermal bonding method, a melt blow method, and a needle punch method, or the like. These methods are suitably used to obtain a nonwoven fabric. In these processing methods, the spun lace method is excellent in flexibility and drape ability, and the thermal bonding method is excellent in bulkiness and soft feature. When a plurality of through holes are formed on the liquid-permeable top sheet 411, urine is absorbed promptly, presenting an excellent dry-to-the touch feature. The liquid-permeable top sheet 411 extends to the back side of the absorbent body 413, wrapping the side edges of the absorbent body 413.

As for leakage preventing sheet 412 that covers the back side (non-skin contact side) of the absorbent body 413, non-permeable plastic sheets, such as polyethylene, polypropylene or the like, are used. However, in recent years, permeability is preferred in order to prevent effectively the skin from steaming. The water-cut and liquid permeable top sheet serves as a fine porous sheet obtained in such a way that an inorganic filler is melt-kneaded to olefin resin such as polyethylene, polypropylene or the like, then extended in uniaxial direction or biaxial direction. If having the same sheet size, the rigidity falls rather than a pore less sheet, therefore the porous sheet is more excellent in respect of flexibility than a pore less sheet.

On the other hand, gather nonwoven fabrics 415 forming three-dimensional gathers BS, as shown in FIG. 19 and FIG. 20, use a nonwoven fabric that is two-folded to be a double sheet. Side edges of the absorbent body 413 that is wrapped by the liquid-permeable sheet 411 are wrapped thereon by the nonwoven fabric, which extends to the back side of the absorbent body 413 to be integrally bonded. More specifically, the gather nonwoven fabrics 415 are bonded by a hot-melt adhesive in a range from the center to the back side of the absorbent body 413, excepting the three-dimensional gathers BS formation portion in the center of the longitudinal direction of the paper diaper shown in FIG. 19. In addition, as shown in FIG. 20, between both side edges of the longitudinal direction, the gather nonwoven fabrics 415 are bonded by a hot-melt adhesive or the like in the center of the width direction of a paper diaper extending to one of the edges, which extends to the back side of the absorbent body 413, so as to fold up the portion that forms the three dimensional gathers BS on the upper surface portion of the absorbent body 413.

In the inside of the gather nonwoven fabric 415 formed of the double sheet nonwoven fabric, a plurality of thread-shaped elastic members 416, 416 . . . are arranged in raised ends. The thread-shaped elastic members of the raised ends 416, 416 . . . are for forming the three-dimensional gathers BS by raising the nonwoven fabric portion protruded from the absorbent body side edge portion, by its expansion and contraction force, as shown in a product state in FIG. 21.

Figure 21:
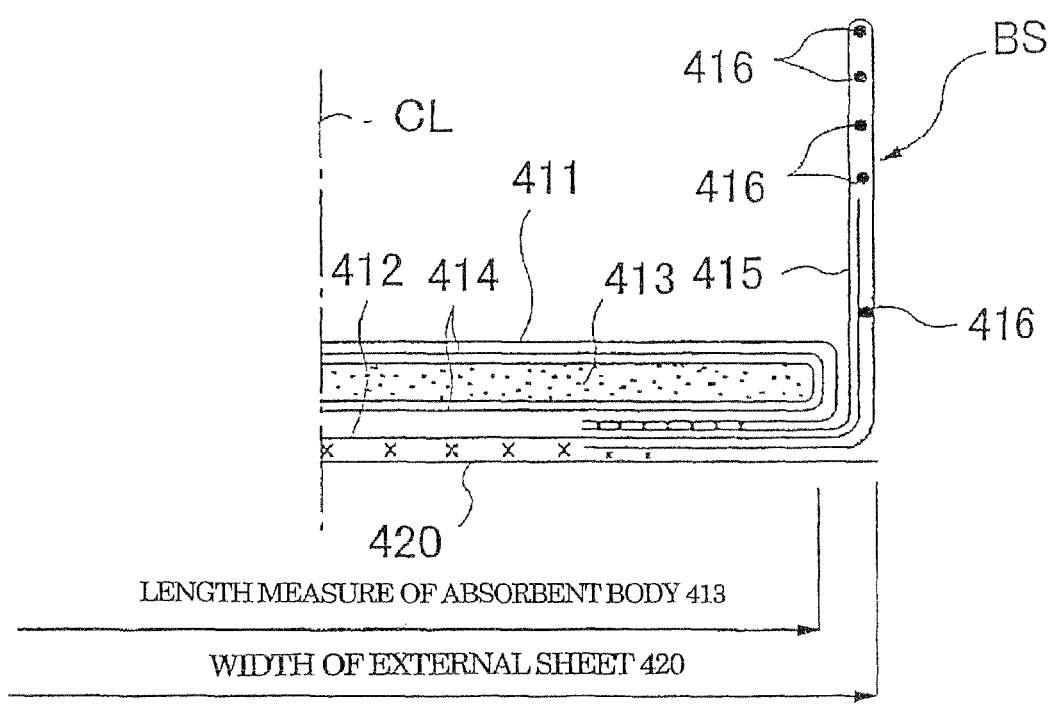
FIG. 21 is a sectional view taken along the line III-III of FIG. 18, in a product state.

The leakage preventing sheet 412 extends to the inside of gather nonwoven fabric 415, which is formed in double layer sheet structure, to constitute a leakage preventing wall on lower end side of the three-dimensional gathers BS, as shown in FIG. 21. It is preferable to use an opaque sheet as the leakage preventing sheet 412, so that brown, which is the color of excretion, may not be visible from the outside. Pigments such as calcium carbonate, titanium oxide, zinc oxide, white carbon, clay, talc, sulfuric acid barium or the like, and fillers added to the plastic to make an opaque film, are preferably used.

The thread-shaped elastic members 416 are composed of materials such as styrene series rubber usually used, olefin series rubber, urethane series rubber, ester series rubber, polyurethane, polyethylene, polystyrene, styrene butadiene, silicon, polyester or the like. Moreover, in order to make it hard to be visible from an outer side, it is preferable to set to 925 dtex or less in diameter, 150 to 350% in tension, and 7.0 mm or less in spaces therebetween. In addition, the thread-shaped elastic members can be replaced with tape-like stretchable members having a certain amount of width.

As a material fiber that constitutes the gather nonwoven fabrics 415, olefins series such as polyethylene or polypropylene, synthetic fibers such as polyester series, polyamide series or the like, in addition, regenerated fibers such as rayon, cupra or the like, and natural fibers such as cotton can be used, similarly to the liquid-permeable top sheet 411. A method for feeding the fiber includes a spun lace method, a spun bond method, a thermal bonding method, a melt blow method, and a needle punch method, or the like. These methods are suitably used to obtain the nonwoven fabric. In order to prevent effectively the skin from steaming especially, the nonwoven fabric that reduces a basis weight and excellent in air permeability is preferably used. Furthermore, as for the gather nonwoven fabrics 415, water repellent treated nonwoven fabric coated with a paraffin metal series and alkyl chromic chloride series or the like is preferably used, in order to prevent sweating and rash while preventing the oozing out of body fluid and the like from the absorbent body, thereby improving a dry-to-the-touch feature to the skin.

(Structure of External Sheet 420)

External sheet 420 is made of a nonwoven fabric sheet. In the nonwoven fabric, at least arrangement region of the elastic members is formed in a double layer sheet structure. In the embodiment shown in the figures, the external sheet of only the front side section F and the back side section B are formed in a double layer sheet structure. On the other hand, a crotch region is formed in a single layer sheet structure. Of course, the nonwoven fabric for internal surface and the nonwoven fabric for external surface may be a two-layers sheet structure by laminating using a hot-melt adhesive. Leg cut-out portions 429 that form leg openings are provided in the center, therefore a nearly hourglass form is accomplished as a whole.

Figure 22:
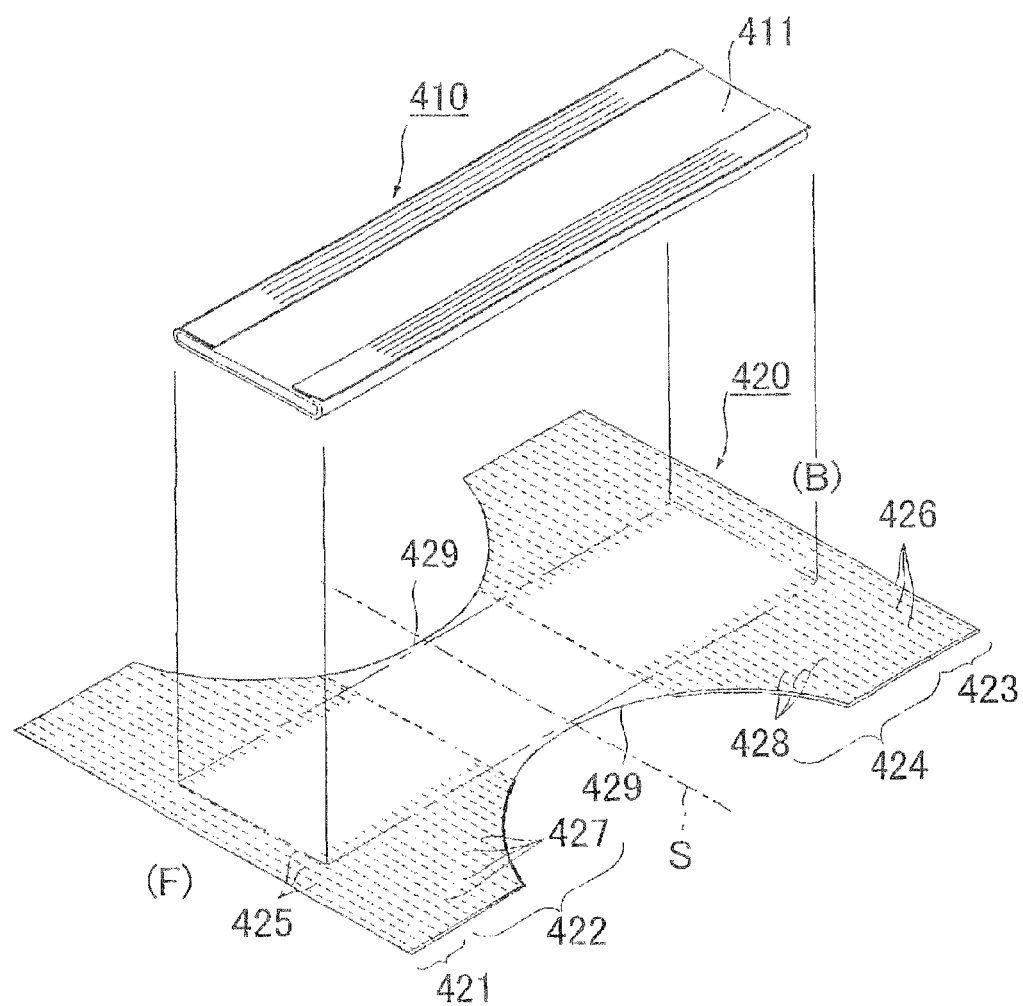
FIG. 22 is an assembly vie W of the main body portion of paper diaper 410 and external sheet 420.

Specifically, in an development form as shown in FIG. 22, in the region of the waist portions 421, 423 of front side section F and back side section B, a plurality of waist-section elastic members 425 . . . , and 426 . . . , composed of thin rubber threads, for example, are respectively provided over the full width.

Also, in the region of the under waist portions 422, 424 of front side section F and back side section B, waist section elastic members 427 . . . , and 428 . . . are arranged along the width direction in both sides region only, except the center. And no elastic members exist along the leg-surrounding portions.

(Assembly of a Paper Diaper)

As shown in FIG. 22, the paper diaper main body 410 and the external sheet 420 are integrated by bonding the paper diaper main body 410 onto the upper surface of the external sheet 420 through hot-melt adhesive or the like. A pant-type of disposable diaper is assembled by folding up a paper diaper main body 410 and the external sheet 420 so as to overlap the front side and the back side with a lengthwise directional center as a fold line S, and by thermally welding or by using hot-melt adhesive, to join both side edges thereof.

Figure 23:
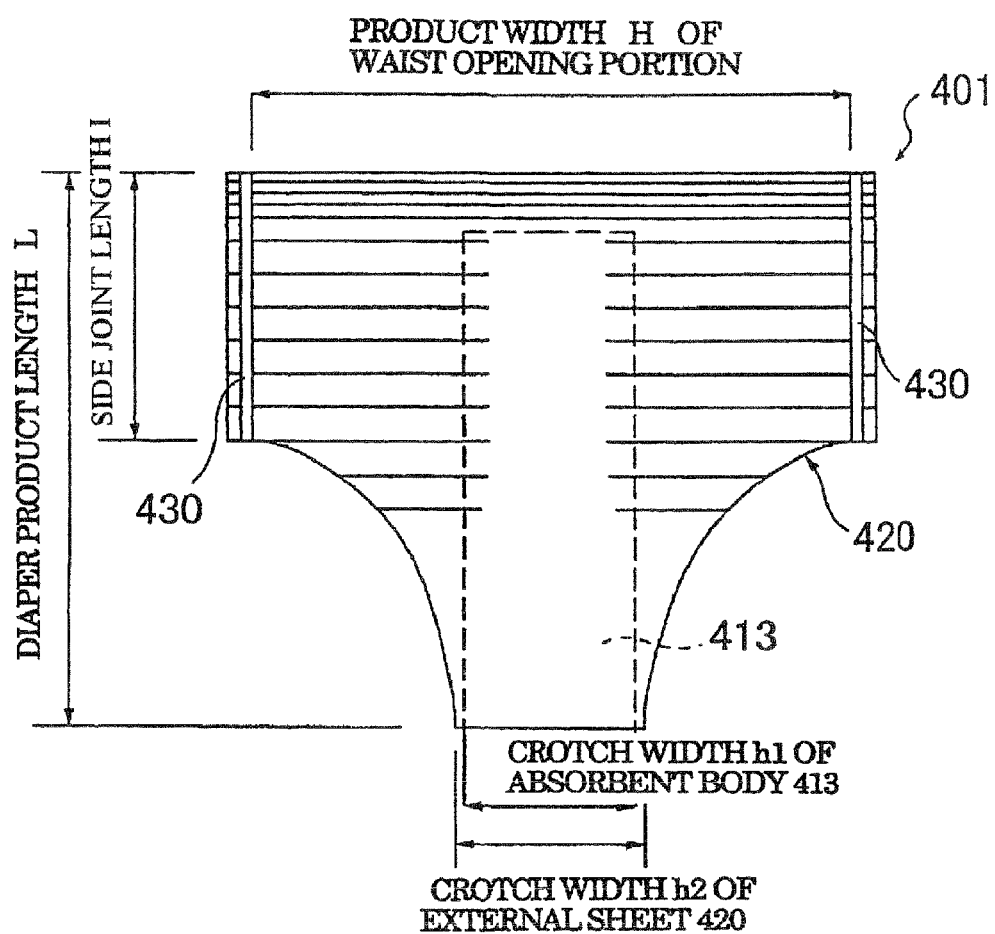
FIG. 23 is a front view showing a product state.

In a paper diaper of the invention, as shown in FIG. 23, in a two-folded product state across the crotch portion, the ratio of a side joint length I to a diaper product length L is 50% or less, and the dimensional ratio of either of larger width h2 of the external sheet 420 in the crotch portion or width h1 of the absorbent body 413 to the product width of a waist opening (in the drawing, since the width h2 of the external sheet 420 is larger, the width h2 of external sheet is adopted.) is 40% or less. In case of (side joint portion length I/diaper product length L)≧50% and (the larger size of width h2 of the external sheet in the crotch portion and width h1 of the absorbent body)/(width H of waist opening portion of product)≧40%, the appearance of a crotch section becomes massive, therefore object of the invention is not satisfied. In addition, width of waist opening portion H means inner width between heat-seal joint portions 430 and 430, when there are no contraction of the elastic members.

Figure 24:
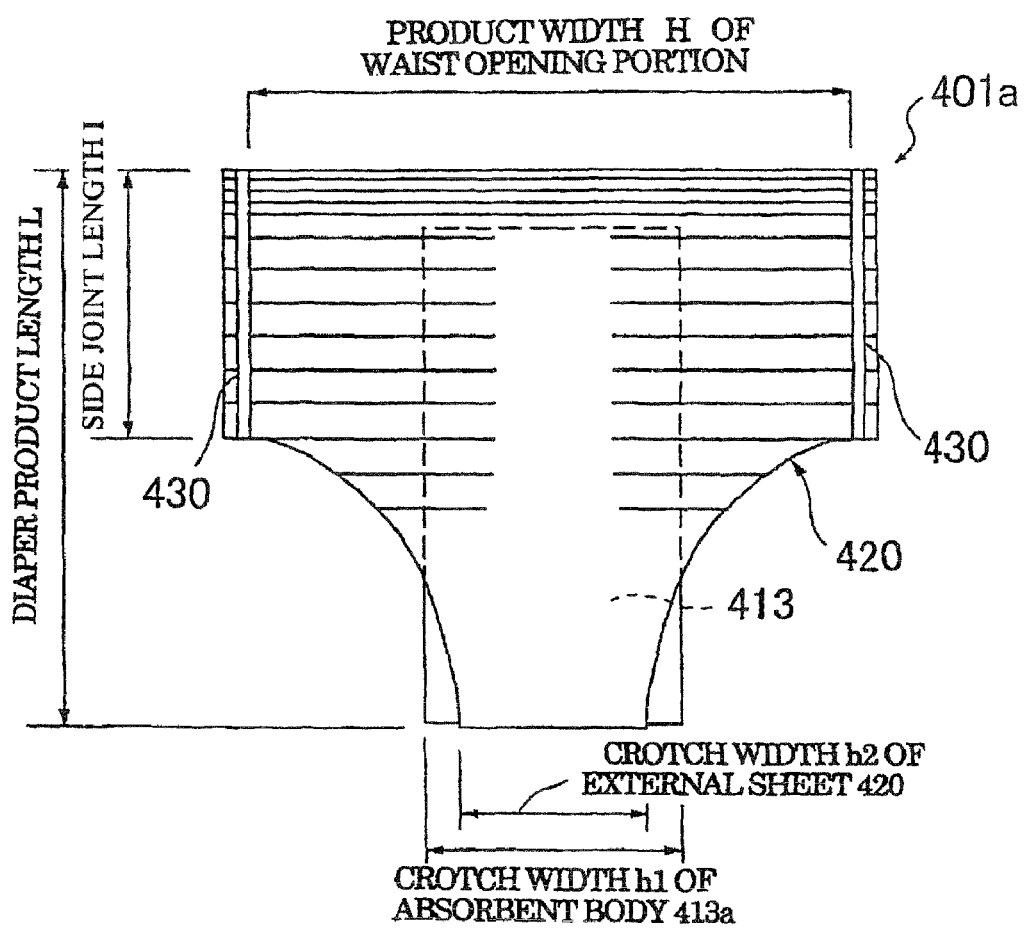
FIG. 24 is a front view showing another structural embodiment of pant-type of disposable diaper 401a of the invention, in a product state.

By determining the formation size of the crotch portion according to the above size ratio, as shown in FIG. 17, a paper diaper of the invention presents brief appearance that has a neat appearance of a crotch portion and leg surrounding portions. In addition, the crotch width is determined by taking larger size of either width of the external sheet 420 or the absorbent body 413. As shown in FIG. 24, sometimes width h2 of the external sheet 420 becomes larger than crotch width h1 of the absorbent body 41, therefore, the size of the crotch width becomes substantially the external width.

Figure 25:
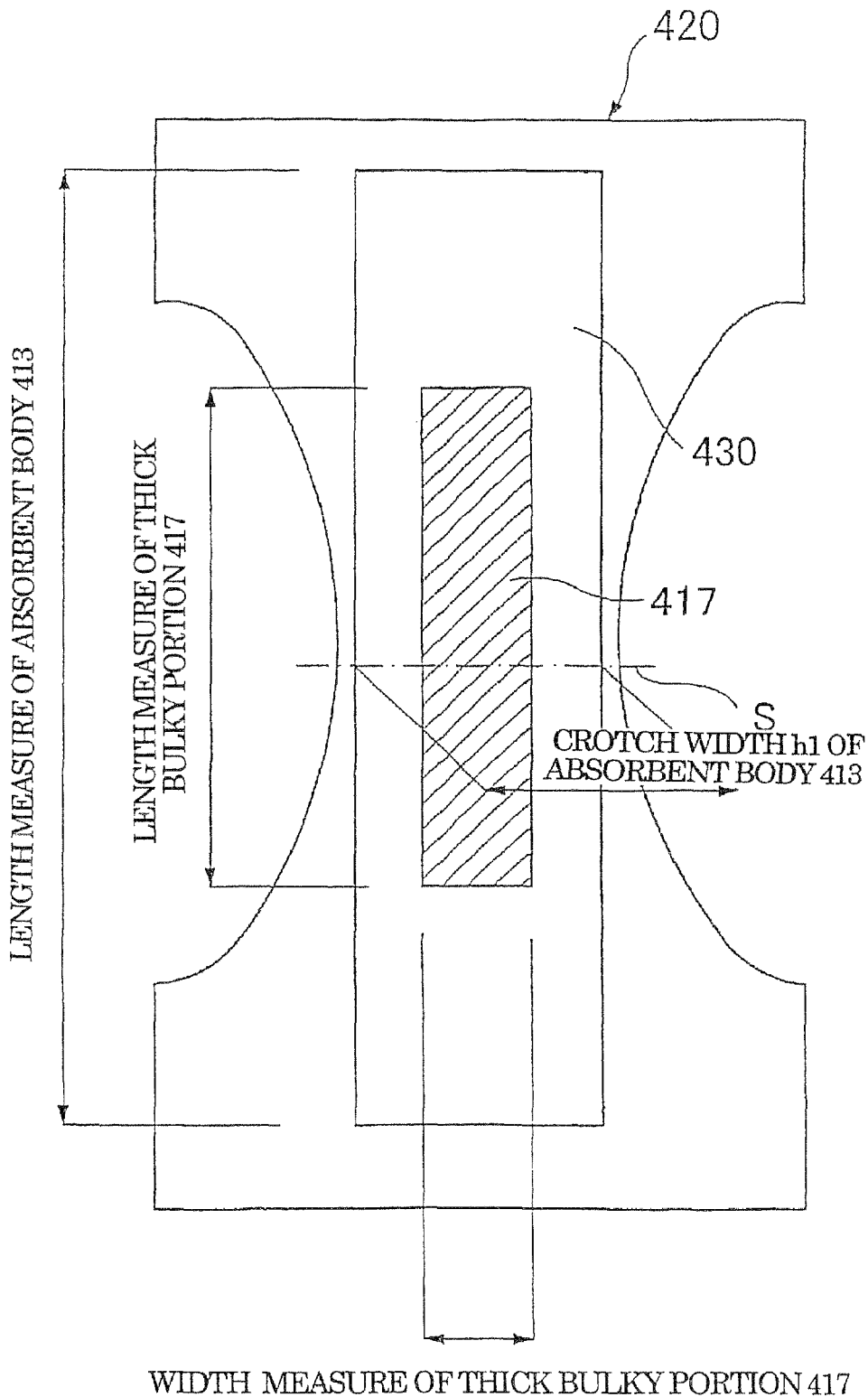
FIG. 25 is a development of a paper diaper showing a region of absorbent thick bulky portion 417.

On the other hand, in the disposable diaper described above, since the absorbent body width of the crotch portion becomes narrower compared with the conventional disposable diaper; as a result, there is a case that it becomes impossible to secure sufficient absorbing capacity. Then, it is preferable to form a thick bulky portion in the range of the absorbent body for retaining the humors discharge, to thereby aim at increase of absorbing capacity partially, as shown in FIG. 25. As a formation range of the thick bulky portion, it is preferable for a width size to be set to 20 to 90% of absorbent body crotch width, and for a length size to be set to 20 to 90% of absorbent body length. Incidentally, the crotch width of the absorbent body means the width of the absorbent body 413 itself including no crepe paper 414 existing therein, near the position of folding line S.

Figure 26A:
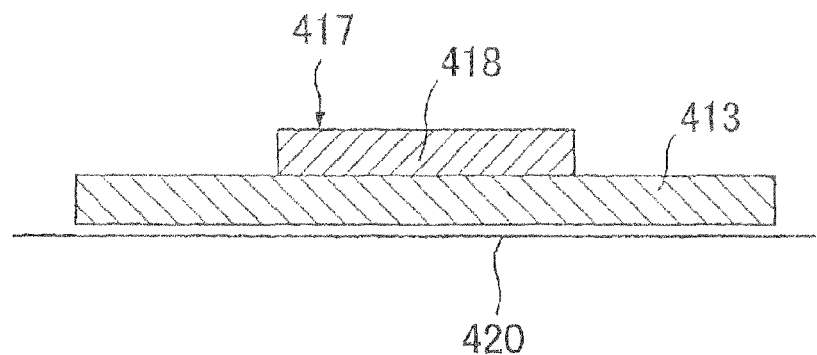
FIG. 26(A) to FIG. 26(C) are sectional views showing a formation method of absorbent thick bulky portion 417.
Figure 26B:
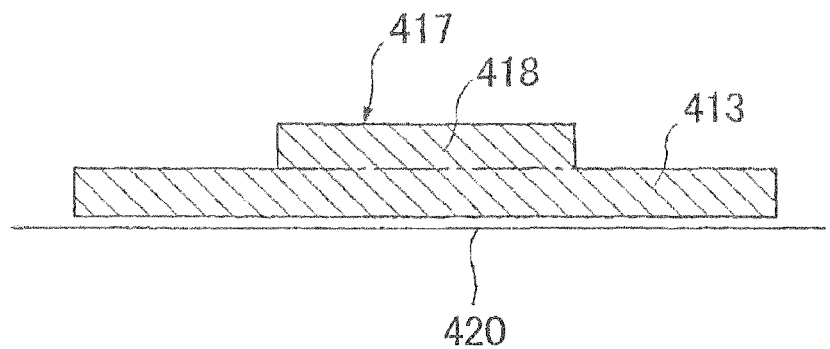
Figure 26C:
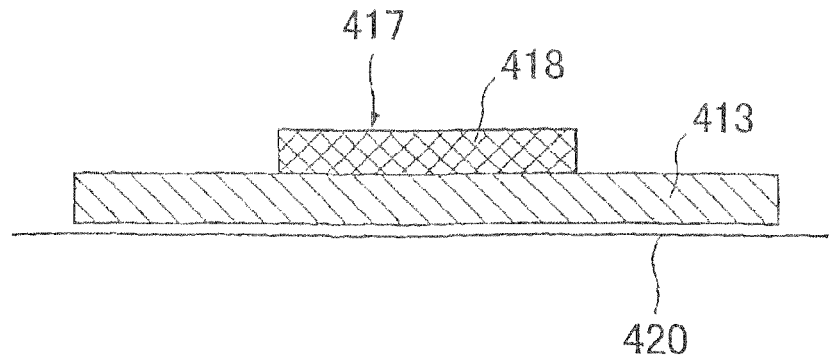

A formation method of the thick bulky portion 417 can be listed in various ways. In the method shown in FIG. 26(A), on the upper surface side of the absorbent body 413, an absorbent body 418 is laminated, wherein the absorbent body 418 is in the range of 20 to 200% increase of the absorbent body 413, preferably 50% increase. In the method shown in FIG. 26(B), the bulky portion 417 is integrally formed with the absorbent body 418 of the same physical properties. In the method shown in FIG. 26(C), the absorbent body 418 is laminated on the upper surface of the absorbent body 413, wherein as the absorbent body 418, laminated one aimed at thinner absorbent body such as an absorptive sheet and an air laying absorbent body, in which the content of a highly absorptive resin is increased, is used. In such cases, the thickness of the absorbent body 413 excepting the bulky portion is preferably 3 mm or less. More preferably, as shown in FIG. 26(A) or FIG. 26(C), as for the absorbent body 418 with the bulky portion 417, it is relatively more desirable that the absorbent body 418 of the bulky portion 417 has a higher absorbing capacity than the absorbent body 413, to aim at a thinner absorbent body as a whole.

Figure 28:
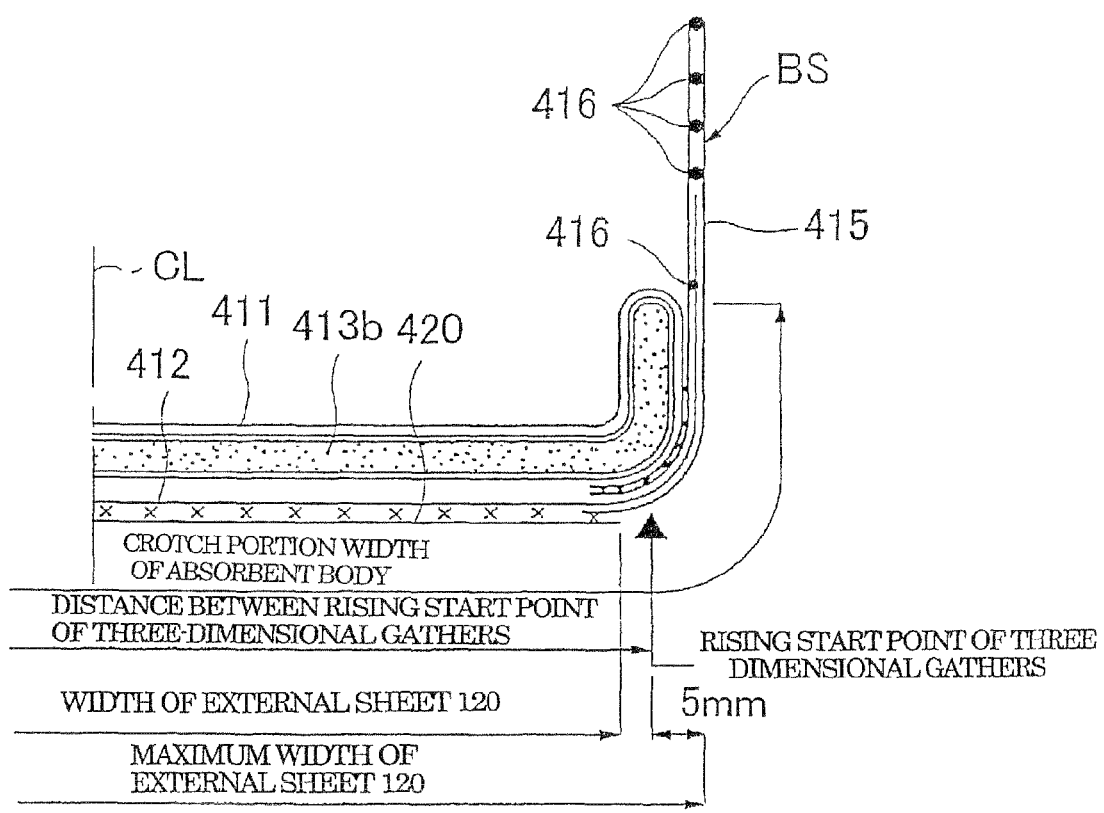
FIG. 28 is a sectional view of a crotch portion showing another embodiment of three-dimensional gathers BS.

As other method for securing the absorbing capacity of the absorbent body 413, as shown in FIG. 28, a method for forming three-dimensional gathers BS by raising both ends of the absorbent body 413b in the longitudinal direction is mentioned. The three-dimensional gathers raised by this absorbent body functions in such a way as to stop body fluid certainly, and the body fluid is absorbed and retained. Thereby, it enables preventing the adverse effect of lateral leakage which is caused by the width of the absorbent body of the crotch portion becoming narrower. In such a case, ratio of the distance between rising start points of the three dimensional gathers to the width of the absorbent body of the crotch portion is preferably 20 to 90%.

Subsequently, in the crotch section, in order to obtain a more neat appearance, frills formed by the external sheet 420 are removed as much as possible. Specifically, in a minimum width area of a crotch portion of the disposable diaper 1, leg cut-out portions 429 of the external sheet 420 forming leg openings are positioned nearer to the center than places outward by 5 mm from side edges of the absorbent body 413, to thereby provide a disposable diaper that has a neat appearance of leg surrounding portions.

Figure 27:
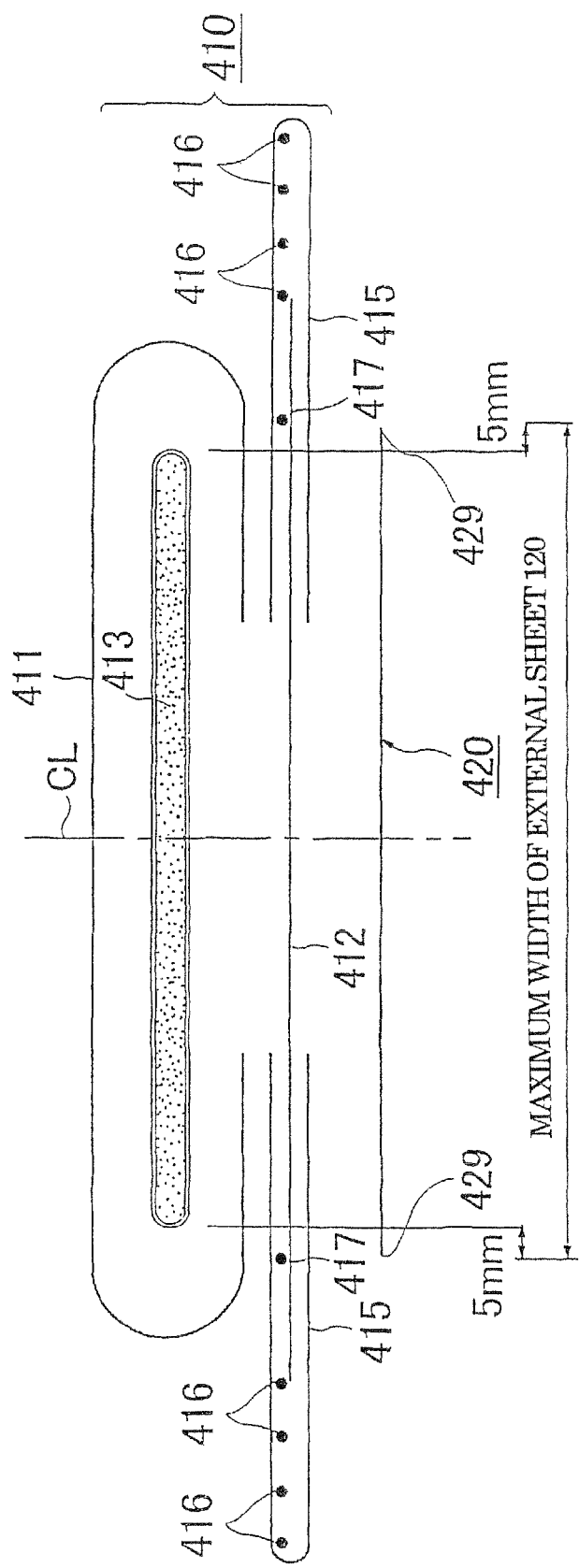
FIG. 27 is an exploded view in section of a crotch portion, showing a leg cut-out position 429 of external sheet 420 of a crotch portion.

Namely, as shown in an exploded sectional view of the crotch portion in FIG. 27, the maximum leg cut-out portion 429 of the external sheet 420 may be within a range outward by 5 mm from both side edges of the crotch width of the absorbent body 413 respectively. The above range is preferably made so that the external sheet 420 may be fit into, and the frills may not be formed as much as possible. Incidentally, side edges of the absorbent body that specifies the leg cut-out portion 429 of the external sheet 420 means the side edges of absorbent body 413 itself including no crepe paper 414 existing therein.

As shown in FIG. 28, when raising both ends of the absorbent body 413b in the longitudinal direction to form the three dimensional gathers BS, it is not necessarily appropriate to determine the leg cut-out portion 429 with respect to the side edges of the absorbent body 413, but it is preferable to determine the leg cut-out position 429 with respect to the raising ends of the three dimensional gathers BS. Accordingly, in this case, the leg cut-out portions of the external sheet forming leg openings are positioned nearer to the center than places outward by 5 mm from rising start points of the three-dimensional gathers BS.

By the way, arrangement mode of the elastic members arranged over the external sheet 420 is arbitrary. FIG. 29(A) to FIG. 29(E) are views showing the arrangement pattern. FIG. 29(A) shows an example in which two lines of elastic members 435, 435 for raising the absorbent body, are arranged in the longitudinal direction of the paper diaper. FIG. 29(B) shows an example in which two lines of elastic members 435, 435 for raising the absorbent body are arranged and leg section elastic members 436, 436 are also arranged on whole peripheries of the leg surrounding portions. FIG. 29(C) shows an arrangement of leg section elastic members 436 arranged in a crossing manner at the crotch portion. FIG. 29(D) shows an arrangement of leg section elastic members 436 arranged in parallel in the crotch portion FIG. 29(E) shows an arrangement of leg section elastic members 436 arranged along the longitudinal direction of the paper diaper.

Figure 30A:
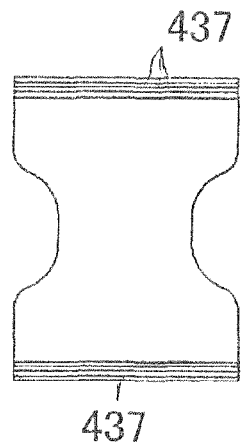
FIG. 30(A) to FIG. 30(E) are views showing arrangement patterns of a waist opening and waist surrounding section elastic member of the external sheet 420.
Figure 30B:
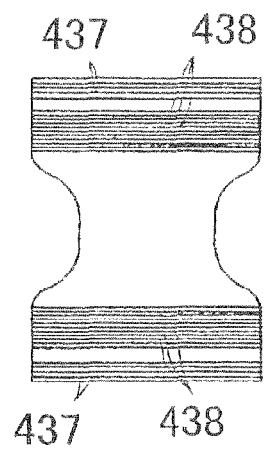
Figure 30C:
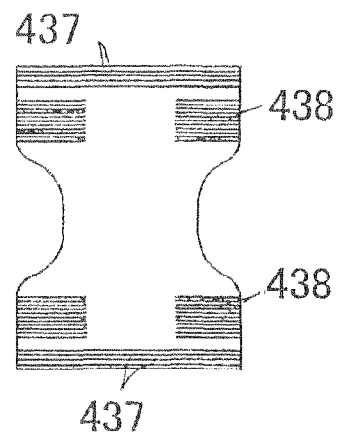
Figure 30D:
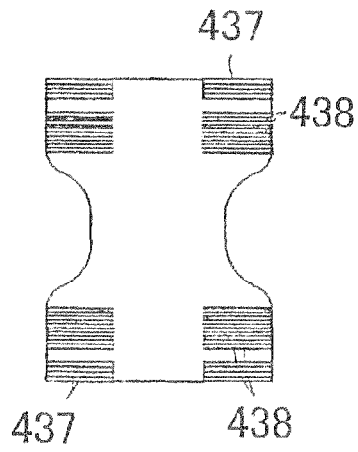
Figure 30E:
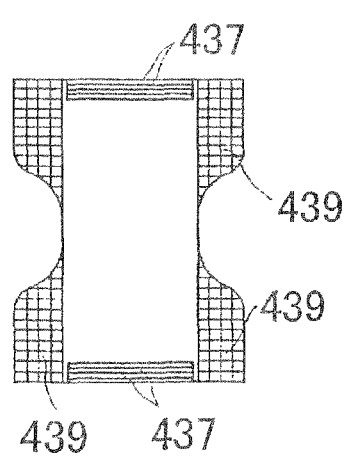

Also, the arrangement mode of the waist section elastic members and the under waist section elastic members are similarly arbitrary. FIG. 30(A) to FIG. 30(E) are views showing the arrangement pattern, wherein FIG. 30(A) shows an arrangement of the waist-section elastic members 437 only, and FIG. 30(B) shows an arrangement of the waist section elastic members 437 and the under waist section elastic members 438, extending on the whole width. FIG. 30(C) shows an arrangement of the waist-section elastic members 437 extending on the whole width and of the under waist section elastic members 438 at both sides only, excepting a central section. FIG. 30(D) shows an arrangement of the waist-section elastic members 437 and the under waist section elastic members 438 at both sides only, excepting a central section. FIG. 30(E) shows an arrangement of side sheets 439 composed of another elastic material which are attached to the body side portion.

As described above, the pant-type of paper diaper was taken for the example for explaining the invention. However, the invention is completely applicable similarly to a tape fastening type of paper diaper.

As explained in detail above, the fourth embodiment provide a paper diaper which makes leg opening edges with no frills and hardly flutterable and makes portions around the legs neat and attractive. In addition, problems, such as itchy rash or stiffening feeling when wearing trousers thereon, due to contact of the frill to the skin can be solved.

Next, a disposable diaper according to the fifth embodiment of the invention will be explained, taking a pant-type of disposable diaper for example. Subsequently, a disposable diaper according to the sixth embodiment of the invention will be explained taking a tape fastening type of paper diaper, so to speak, having a fixing section bonded by tape fastener (an adhesion agent tape fastener and a field fastener are included) at both sides in the longitudinal direction, wherein side edges of the back side is brought to side edges of the belly side, for example.

Fifth Embodiment

The disposable diaper according to the fifth embodiment of the invention will be explained in conjunction with FIG. 32 to FIG. 36, while giving term explanation about the portion and direction of the invention referring to FIG. 31.

Figure 32:
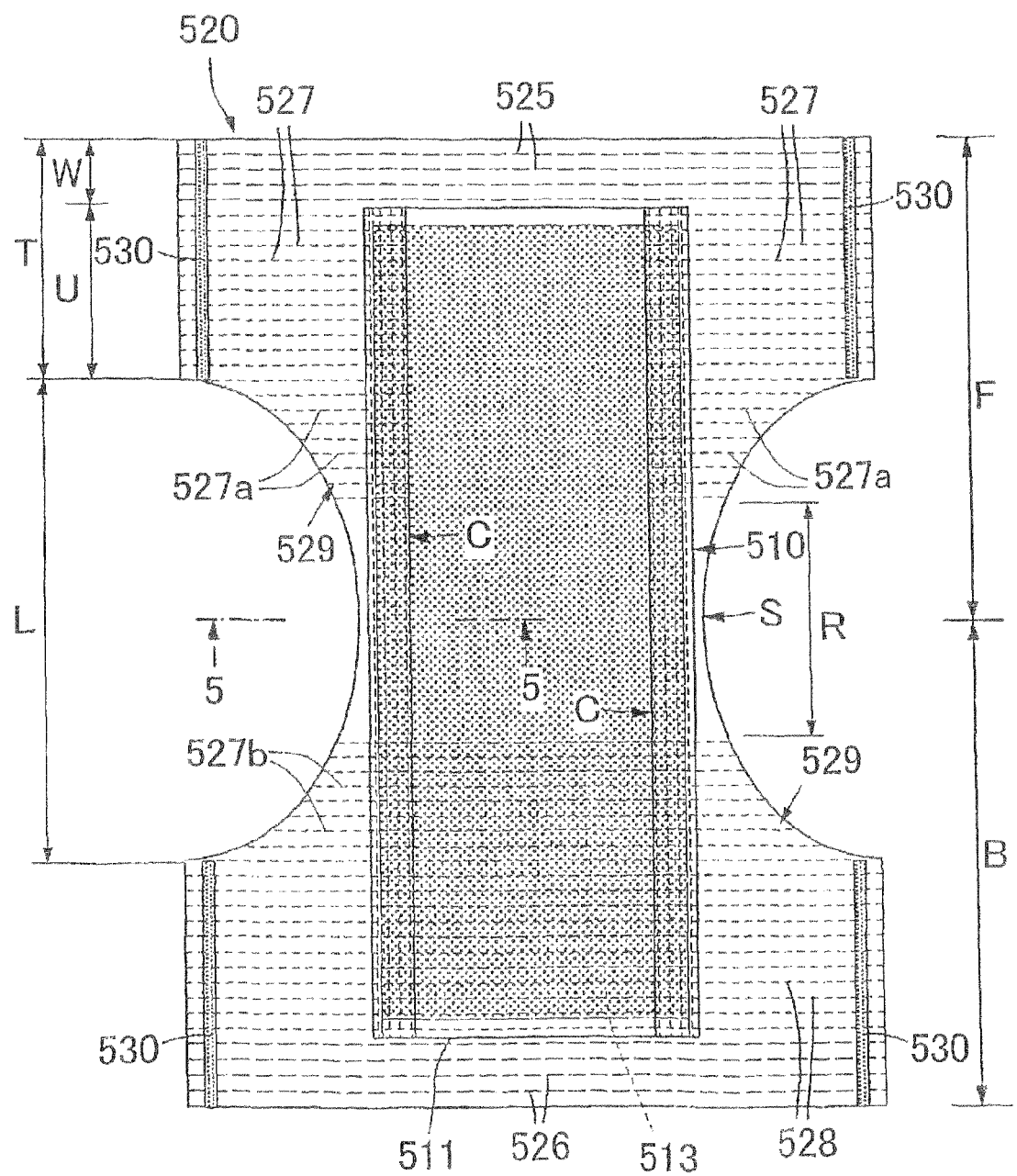
FIG. 32 is a plan view from a use surface side showing a development of a pant-type of disposable diaper according to the fifth embodiment of the invention.
Figure 33:
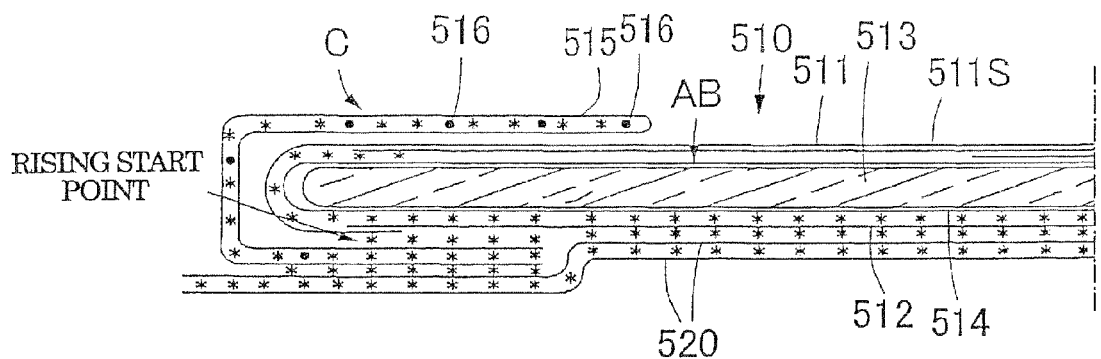
FIG. 33 is a sectional view taken along the line 5-5 of FIG. 32.
Figure 34:
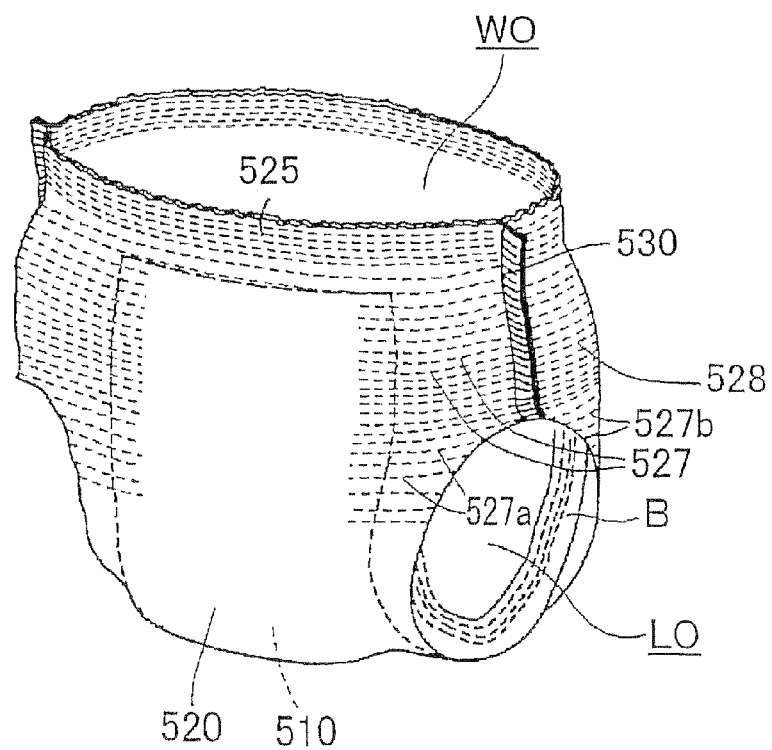
FIG. 34 is a perspective view showing a use state.

As shown in FIG. 32 and FIG. 33, a pant-type of disposable diaper according to the fifth embodiment is mainly constituted by flexible external sheet 520 and paper diaper main body 510 extending across the crotch portion in the longitudinal direction (front and back direction).

The external sheet 520 is formed by laminating fixation of an air permeable and water-repellent nonwoven fabric of two sheets or three sheets or more. And in the final stage of the manufacturing process after the external sheet 520 is laminated on the paper diaper main body 510, the whole longitudinal direction of both side edges of front side section F and back side section B are bonded by ultrasonic seal or thermal fusion (the joint portion is denoted as 530), to thereby form waist opening portion WO and a pair of leg openings LO in right and left.

Figure 31:
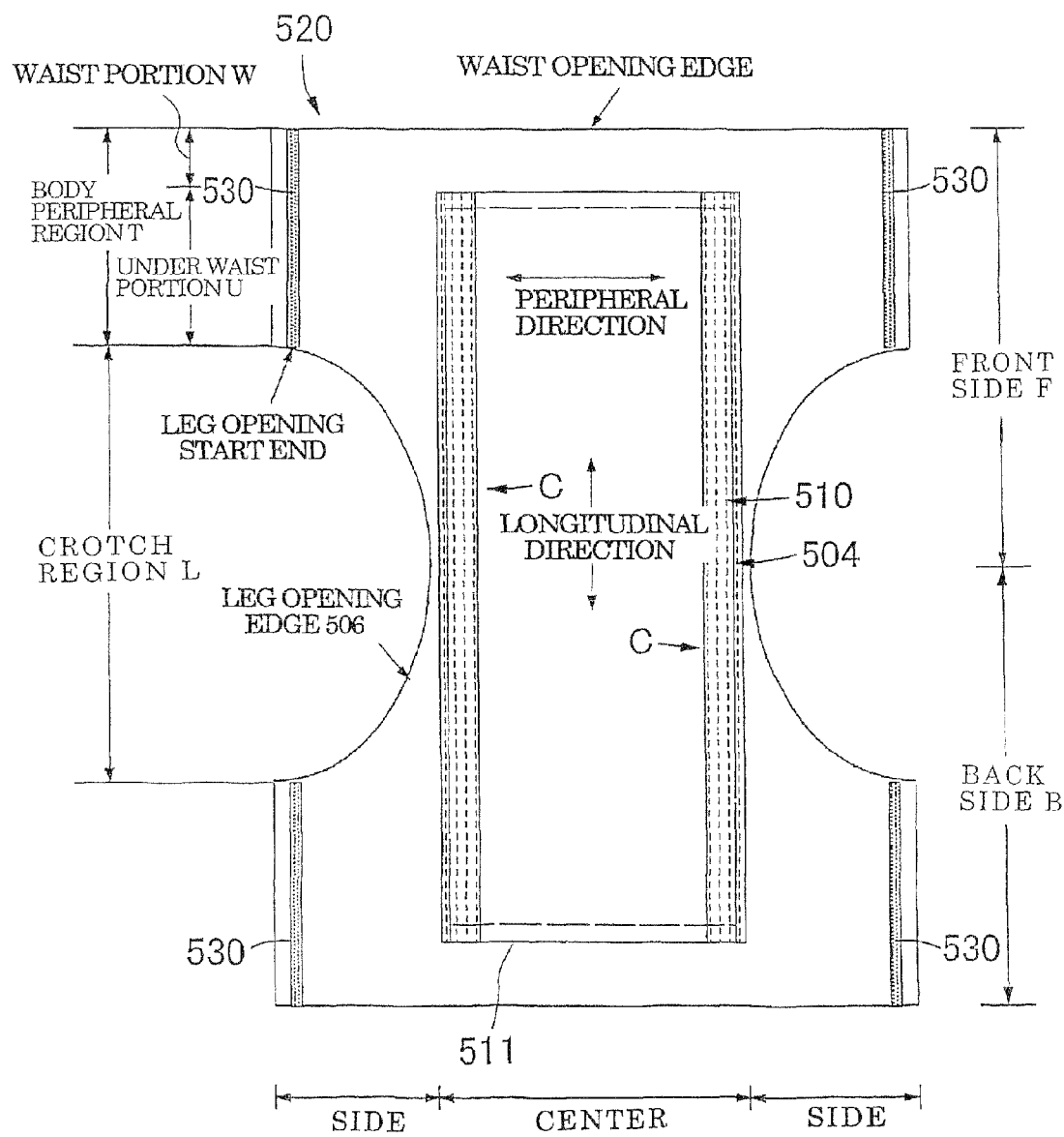
FIG. 31 is a plan view from a use surface side, showing a development of a pant-type of disposable diaper according to the fifth embodiment of the invention, in view of a term explanation.

As denoted in FIG. 31, "longitudinal direction" means the direction to connect a belly and back side, and "peripheral direction" means the direction that intersects with the longitudinal direction perpendicularly (or product width direction). "Waist opening edges" mean the edges of the waist opening WO, and a "leg opening edges" mean the edges of the leg opening LO. "Leg opening initial end" means the position which intersects the leg opening edges of the leg opening LO and joint portion 530, meaning the beginning portion of the leg opening edges. The "body peripheral region" T means the whole length range region from the waist opening edges to the leg opening initial end. The body peripheral region T can be notionally divided into "waist portion" W and "under waist section" U. Length thereof in the longitudinal direction changes by sizes of a product, however the waist portion W is 15 to 40 mm and the under waist section U is 45 to 120 mm. "Crotch region" L means the region forming the leg opening portions, that is, the whole region from the leg opening initial end of the front side section to the leg opening initial end of the back side section. Moreover, "Central portion or center" means the middle region including a central line of a product excepting a side portion. "Side portion" means both-sides portion in the body peripheral region T.

As shown in FIG. 33, the disposable diaper main body 510 comprises a rectangular shaped liquid-permeable top sheet 511 made of nonwoven fabric or the like which touches a wearer's skin directly; an absorbent body AB which comprises an absorbent core 513 mainly composed of a cottony pulp and having a certain amount of rigidity (semi-rigid), and a rectangular shaped crepe paper 514 that wraps the whole upper and lower surfaces of the absorbent core; and a rectangular shaped leakage preventing sheet 512 composed of polyethylene plastic film or the like extending to the vicinity of both edges of the back side of the absorbent body AB. The liquid-permeable top sheet 511 extends around the outside of the side edges of the absorbent body AB to reach the back side thereof, and laminated on the leakage preventing sheet 512. Each of these elements is integrally bonded (joint portion is specified by * in the figure) by a hot-melt adhesive. As shown in the figure, the liquid permeable second sheet 5115 can be interposed between the liquid permeable top sheet 511 and the crepe paper 514 as shown in the figure, as needed. The whole surface of the back side of the paper diaper main body 510 is integrally bonded to the external sheet 520 by a hot-melt adhesive.

Leg section rising cuffs C and C for portions around legs projecting toward a use face of the paper diaper main body 510 are formed on both sides. The rising cuff C is formed of a raising sheet 515 continuous in the width direction and one or a plurality of elastic expansion members 516, 516 . . . made up of thin rubber thread or the like.

More specifically, the rising cuff C is formed double by folding inwardly the raising sheet so as to wrap each elastic expansion member 516, 515 . . . fastened by a hot melt adhesive or the like. The raising sheet 515 having each rising cuffs C and C formed thereon is preferably not permeable but non-permeable, or hydrophobic. For this reason, another sheet (such as film and nonwoven fabric) may be laminated in the inner surface of the raising sheet 515, thereby improving the water-proof property. In addition, the liquid permeable top sheet such as nonwoven fabric may be subjected to silicon processing, so that water-repellent property is added thereto. Furthermore, air permeability or steam permeability is preferably presented.

The inner surface of the double raising sheet 515 extends to the back side of the absorbent body AB and leakage preventing sheet 512, and is bonded by a hot-melt adhesive or the like to be fastened thereto. Consequently, the fastening initial end of the double raising sheet 515 forms the rising ends of the rising cuff C.

In the side nearer to the tip end than the rising end, free portions, which are not fastened to a product main body, is formed.

On the other hand, at both ends of the longitudinal direction, the free portions are fastened by a hot-melt adhesive to the product, more specifically to outer surface of the liquid-permeable sheet 511. The tip end of the rising portion is heading from the rising end to the center side of a product.

In addition, at least one of thread-shaped elastic members 516, 516 is included in the free portion as a basic form. Especially, the thread-shaped elastic members 516 are preferably included in the tip end of the free portion. Further, as shown in FIG. 33, the thread-shaped elastic members 516 are preferably included in a root side. In the edge, as shown in the figure, a plurality of thread-shaped elastic members are preferably included.

FIG. 32 is a view showing a paper diaper in an development state in the longitudinal direction. The paper diaper is fitted into human body in a boat-shaped form, and expansion and contraction elasticity of each thread-shaped stretchable members 516, 516 . . . works. Therefore, in the leg section, the rising cuff C is raised by the contraction force of each thread-shaped elastic members 516, 516 . . . . At this time, the side portion of the disposable diaper main body 510 is changed in form and raised, and the absorbent body AB is also changed in form and raised, to thereby form a deep pocket space.

The space surrounded by right and left rising cuffs C and C forms a body fluid retaining pocket. If urinating in this space, the urine is absorbed in the absorbent body element AB through liquid permeable top sheet 511, and as for a solid portion of the excretion liquid, the rising cuff C serves as barrier, to prevent oozing out.

On the other hand, in the edge of the longitudinal direction of the front side section F and the hack side section B, and between nonwoven fabrics of the external sheet 520 in the waist portion W, the waist section elastic members 525, 526 composed of thin rubber thread are arranged and fastened in a state of being elongated, so as to be expanded and contracted, keeping an space in parallel to the edges of the waist opening portion WO, in order to improve fitting property of the waist section. The space between and the number of the waist section elastic members 525, 526 can be determined suitably. However, for example, about 2 to 8 mm is preferable as the space, and 4 to 10 is preferable as the number. In addition, thin rubber thread is preferably used for the waist section elastic members 525, 526, specifically, the elastic members of the diameter of 620 dtex or less is preferably used.

Further, in the invention, the under waist section elastic members 527, 528 are provided along the peripheral direction in the lower belly portion of the front side section F and an abdomen portion of the back side section B, serving as lower waist section U, which is the region from the waist portion W of the front side section F and the back side section B to the crotch region L. In this example, the under waist section elastic members 527 of the front side section F is provided at right and left side portions of the product, in the region from the joint portion 530 of one side to the joint portion 530 of the other side, excluding almost whole portion of the absorbent body 513. On the other hand, the under waist section elastic members 528 of the back side section B is continuously formed extending from the joint portion 530 of one side to the joint portion 530 of the other side.

Preferably, thin rubber thread is used for the under waist section elastic members 527, 528, and specifically, the elastic members of the diameter of 620 dtex or less is used. The space between the elastic members is 7.0 mm or less in the longitudinal direction. Thereby, 15 to 10 pieces of elastic members are arranged and fastened in parallel respectively, between the nonwoven fabric of the external sheet 520. Mutual space between the under waist section elastic members 527 and 528 is preferably the same or shorter compared with the space between the waist section elastic members 525, 526.

Also, thin rubber thread used for the under waist section elastic members 527, 528 can be smaller in extension stress and a cross-sectional outer diameter, or substantially the same, compared with the thin thread rubber used for the waist section elastic members 525. Specifically thin thread rubber used here has preferably the extension stress of the range of 4 to 17 g, at the time of 150% extension, especially the extension stress of the range of 5 to 10 g.

According to the above-described constitution of the invention, a plurality of shaping elastic members 527*a*, 527*b* for expansion and contraction elasticity that works on the leg opening edges 529, 529 toward the central portion of the width direction are formed at spaces in the longitudinal direction in at least leg opening edges 529, 529 of the crotch region L. More specifically, in this embodiment, the shaping elastic members 527*a* are continuously formed over the front side section F of the crotch region L, from both leg opening edges 529, 529 to the position corresponding to the absorbent core, and not formed in the central portion of the absorbent core 513. Also, over the back side section 5, the shaping elastic members 527*b* are continuously formed from one of the leg opening edges 529 to the other. Especially, in an example of the invention, the shaping elastic members 527*a*, 527*b* are formed excluding length range A of 2 to 3 cm respectively (4 to 6 cm in total) in front and back portions of the crotch section 4 in the crotch region L.

The elastic members 527*a* is also preferably constituted including the elastic members of the diameter 629 dtex or less that are arranged and fastened at spaces of 7.9 mm or less in the longitudinal direction between the nonwoven fabrics, similarly to the under waist section elastic members 527, 528.

Figure 35A:
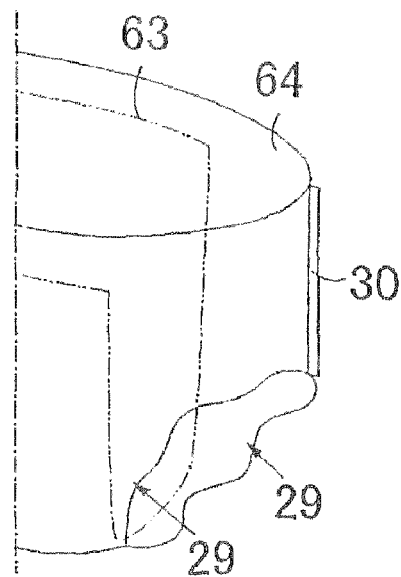
FIG. 35(A) is a major structure of a conventional pant-type of diaper by way of perspective view.
Figure 35B:
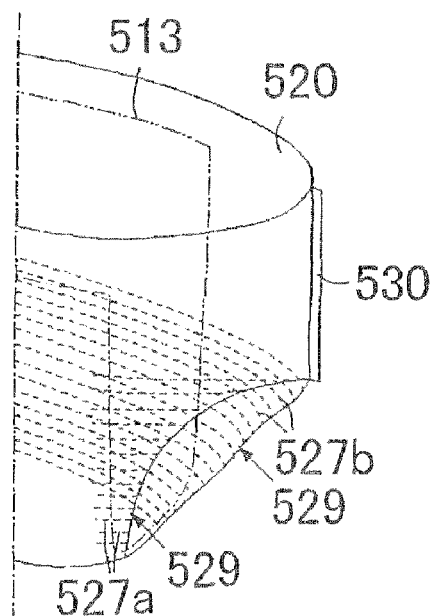
FIG. 35(B) is a major structure of a pant-type of diaper by way of perspective view according to the fifth embodiment of the invention.

In a paper diaper of the invention thus formed, as shown in FIG. 35(B), the leg opening edges 529, 529 shrink in parallel to the under waist section by the shaping elastic members 527*a*, 527*b*, and a plurality of complicated fine wrinkles are formed in parallel along the longitudinal direction (direction that intersects the shrinkage direction perpendicularly). And the rigidity of the leg opening edges 529,529 is increased by these vertical fine wrinkles. By obtaining a combined effect with the above, a paper diaper which makes leg opening edges 529, 529 hardly flutterable like the conventional product (see FIG. 35(A)), and makes portions around the leg neat and attractive is provided. Further, by the above advantageous effects, fitting property to trousers is improved, to thereby present a neat appearance even when wearing trousers layered on the paper diaper.

Especially in the embodiment of the invention, in addition to the above-described advantageous effects, the advantageous effects to prevent lateral leakage is obtained. More specifically, the shaping elastic members 527*a*, 527*b* of the front side section F are not continuously formed in the place corresponding to the absorbent core 513, therefore, expand and contraction force in the width direction applied to the absorbent core 513 is weakened. The vertical wrinkles thus formed along the tightening direction of the body peripheral direction by the action of the elastic members, which are laterally crossing over the absorbent body AB, prevent the absorbent body from detaching the skin, to thereby prevent the lateral leakage. On the other hand, in the back side section B, the shaping elastic members 527*a* are continuously formed from the leg opening edges of one side to the other, to thereby improve the fitting property of the contact portion to the skin, preventing slipping down.

Figure 36A:
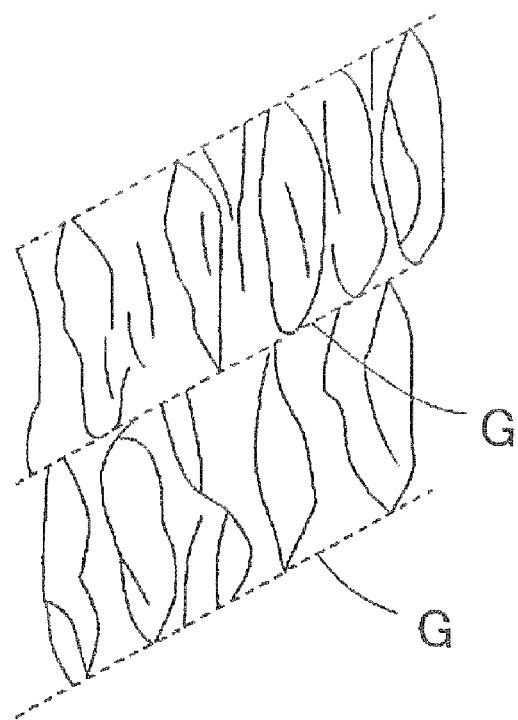
FIG. 36(A) and FIG. 36(B) are schematic view showing wrinkle generation states of a conventional pant-type of diaper and of the pant-type of diaper according to the fifth embodiment of the invention, respectively.

As for the waist section elastic members 525, 526, the under waist section elastic members 527, 528, and the shaping elastic members 527*a*, 527*b*, in the outside of the diameter range or the space range of longitudinal direction, as schematically shown in FIG. 36(A), wrinkles generate between adjoining thin rubber threads in such a manner as to extend from one of the adjoining thin rubber thread G to the other thin rubber thread, accompanying contraction of thin rubber thread G, as schematically shown in FIG. 36(A). The uneven wrinkles generate in a state of repetition in the direction of the under waist section. Furthermore, the adjoining wrinkles between thin rubber threads G and the next adjoining wrinkles thereto between thin rubber threads G do not continue, but are apt to generate independently. When the arrangement space between mutual thin rubber threads is large, these wrinkles have long ridge or valley according to the separating distance of the mutual thin rubber threads, and the pitch of the unevenness in the body peripheral direction is large. Accordingly, if viewed on the whole in the external surface of a product, large wrinkles generate at random. The external surface of the product becomes stuffy, and the image is far from the pant-type of clothing. Furthermore, each thin rubber thread G in the conventional product is thick, and its shrink force is large. Therefore, if one ridge wrinkle is taken for an example, the valley on the thin rubber threads G side becomes deep, making the existence of the thin rubber thread G conspicuous. Moreover, since the ridge or the valley is large and shrink force acts strongly, complicated fine wrinkles generate at random in the ridge portion or the valley portion. On the other hand, the existence of the thick rubber threads G is visible through the non-woven fabric. Therefore, it is feared that thick rubber threads C possibly bind a wearing person's skin tight strongly. Actually, in the side portion in which an absorbent body does not exist, the shrink force of the thick rubber threads G acts strongly, thereby forming traces of rubber. Moreover, friction of the inner surface of the product and the skin mainly in the portion where each rubber thread contact with the skin prevents the product from slipping down. However, if large shrink force does not work, the product may possibly slip down.

Figure 36B:
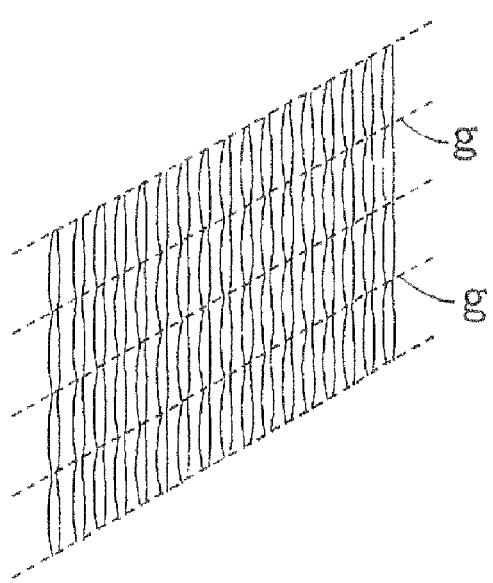

On the other hand, as schematically shown in FIG. 36(B) in the above-described range, the wrinkles narrow in width in the body peripheral direction, short in length in the crotch direction, generate continuously in the crotch direction. Ridge and groove of each wrinkle is very small. In addition, tightening in the rubber thread g portion is rationalized. When the color of a sheet forming external surface and the color of the thin rubber thread g are the same color, it is hard to distinguish existence of the thread rubber g. Consequently, a disposable diaper having no wrinkles conspicuous, having complicated fine wrinkles even if visible, and presenting a flat external surface, with sufficient fitting property and good in appearance without stuffy external surface is produced. In addition, in a disposable diaper of the invention, no formations of traces of rubber are generated by being pressed to the skin on the face, avoiding too much pressure to the skin locally. Since the friction of the inner surface of the product and the skin covers the whole surface, the property of fitting to the physique of a wearing person is improved, and a product is prevented from slipping down also.

Moreover, in order to exert this advantageous effects, 60% or more, preferably 70% or more, and preferably 90% or more elastic members of the range for arranging the elastic members, may have the diameter and spaces described above. In the range of maximum of 40%, the diameter or the space is not necessarily required.

Sixth Embodiment

The shaping elastic members 527a, 527b of the fifth embodiment are fixed to the external sheet 520 by adhesives such as a hot-melt adhesive, in usual case. In this case, there is a possibility that outside edge of the shaping elastic members are drawn in toward a center.

Figure 37:
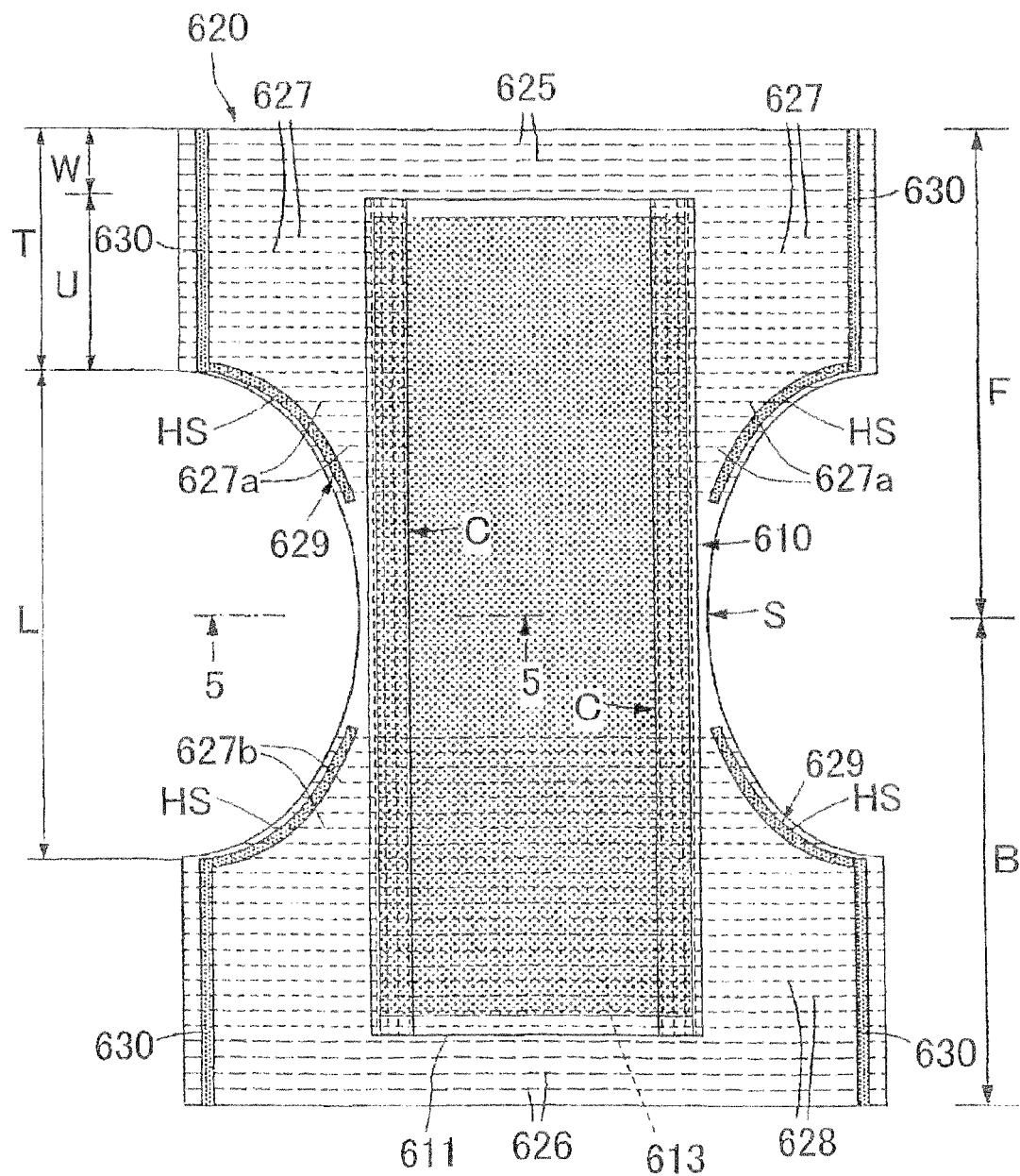
FIG. 37 is a plan view from a use surface side showing a development of a pant-type of disposable diaper according to the sixth embodiment of the invention.
Figure 38:
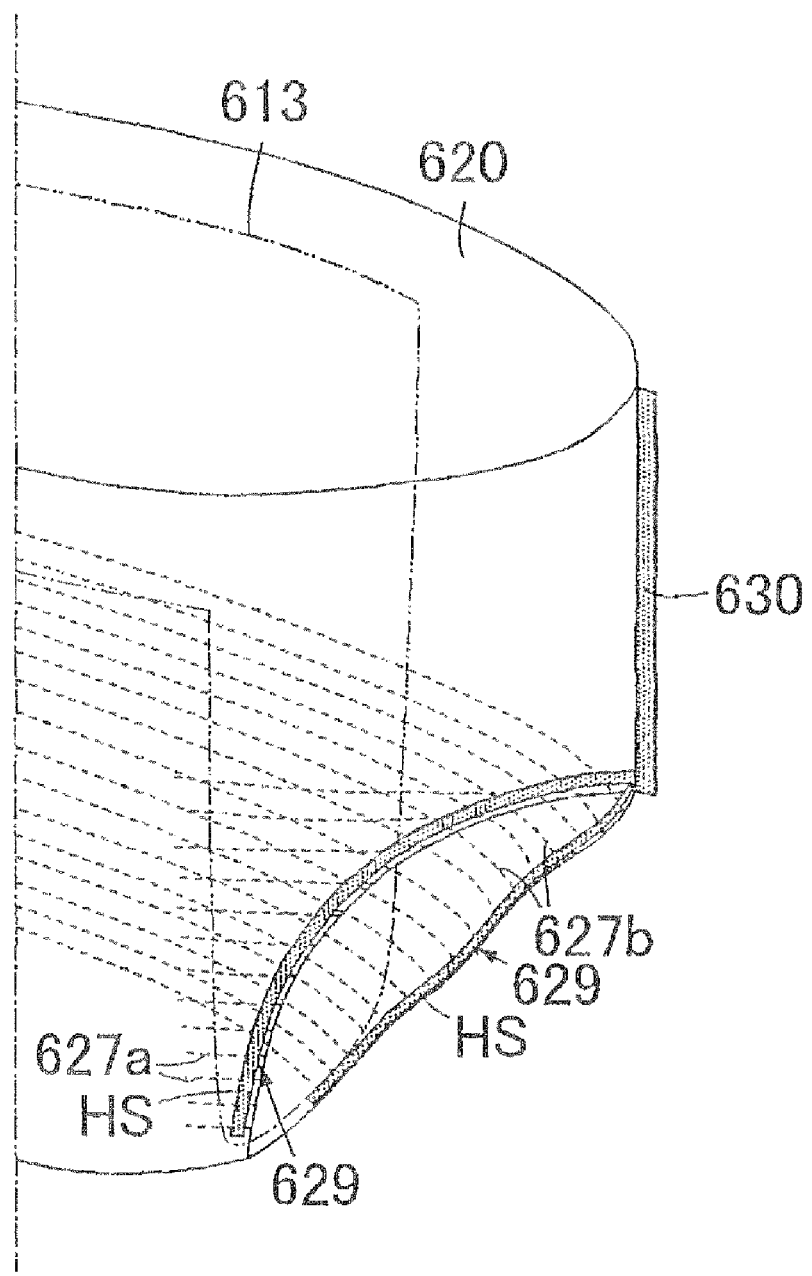
FIG. 38 is a perspective view showing a major structure of a pant-type of diaper according to the sixth embodiment.

Hereupon, in the sixth embodiment, as shown in FIG. 37 and FIG. 38, the outside edge of the shaping elastic members 627a, 627b are reliably fixed by heat seals HS and HS to the external sheet 620. Thus, by such heat seals HS and HS, the outside edge of the shaping elastic members 627a, 627b are reliably fixed and the drawing in is hardly occurred.

Seventh Embodiment

Figure 39:
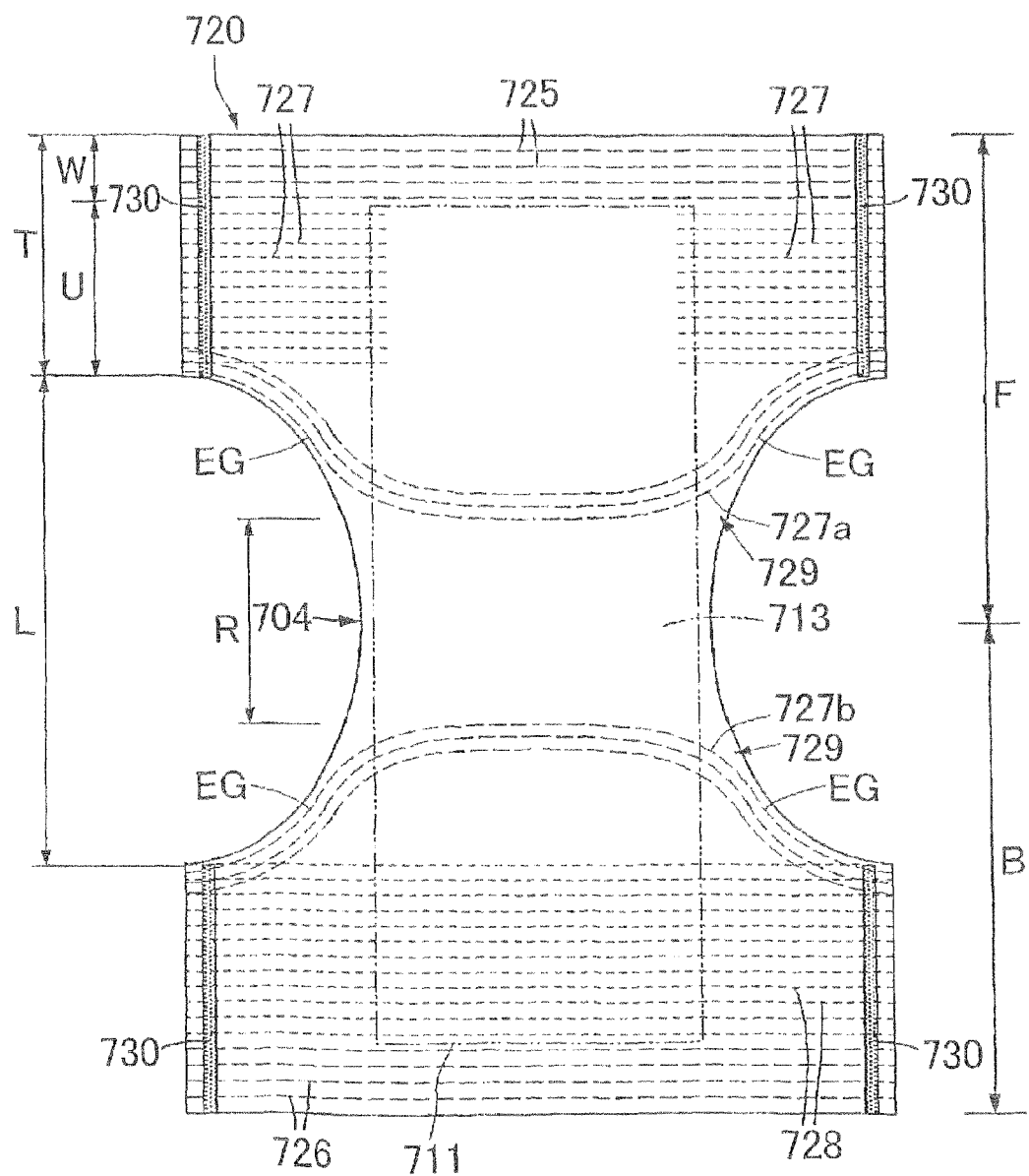
FIG. 39 is a plan view from a use surface side showing a development of a pant-type of disposable diaper according to the seventh embodiment of the invention.
Figure 40:
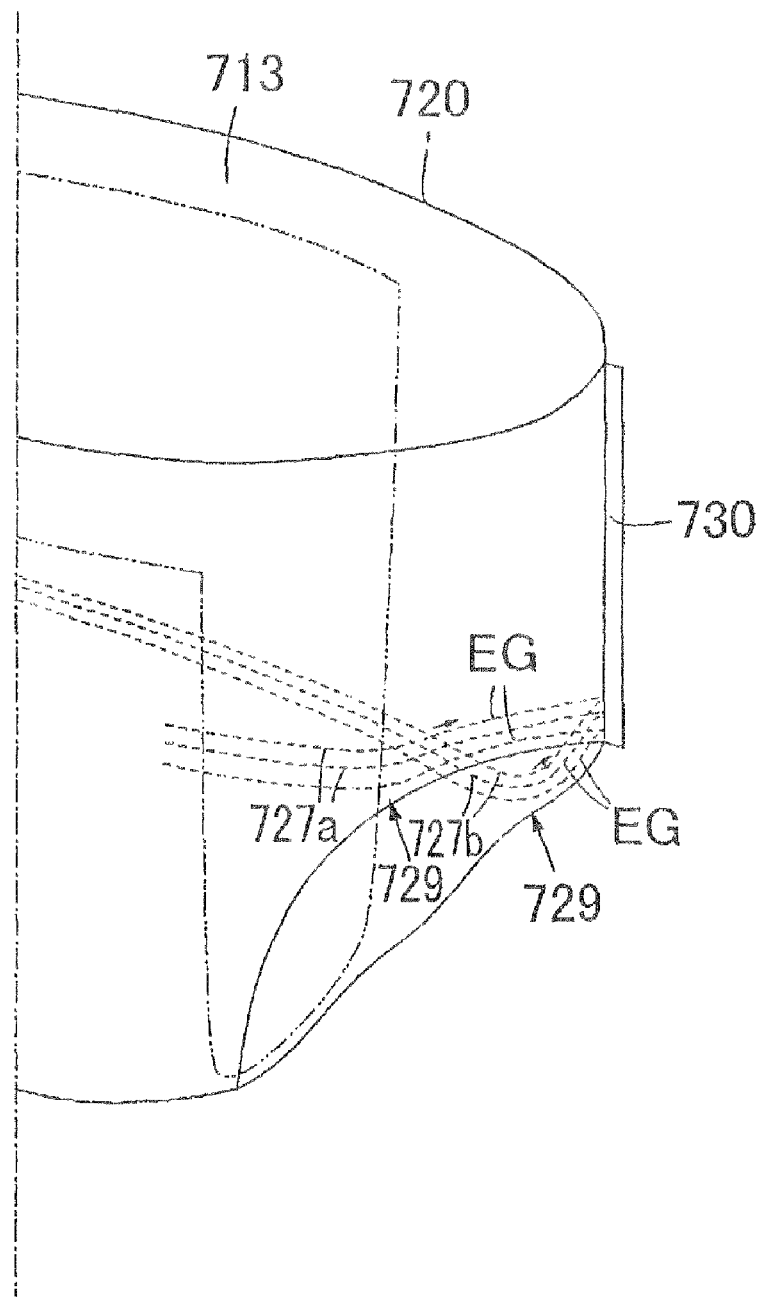
FIG. 40 is a perspective view showing a major structure of a pant-type of diaper according to the seventh embodiment.

As shown in FIG. 39 and FIG. 40, the seventh embodiment provides a formation of the shaping elastic members 727a, 727b that are extended to joint portion 730 (upside portion of the leg opening initial end) along the leg openings corresponding to each body section. This extension portion is denoted by EG.) In this case, the shaping elastic members 727a, 727b are formed excluding the front and rear portion of the length range R of the crotch portion 704 in the length region R by 2 to 3 cm, especially 4 to 6 cm.

According to this embodiment, similarly to the fifth embodiment, in addition to the shrinkage of the leg opening edges 729, 729 by the shaping elastic members 727a, 727b that are parallel to the under waist section, the whole region of the crotch portion including the leg opening edges 729, 729 can be raised by the extension portions EG, EG . . . toward the joint portion 730, that is, toward waist side. Thereby the fitting property to the skin of the whole region of the crotch section is improved.

Eighth Embodiment

Figure 41:
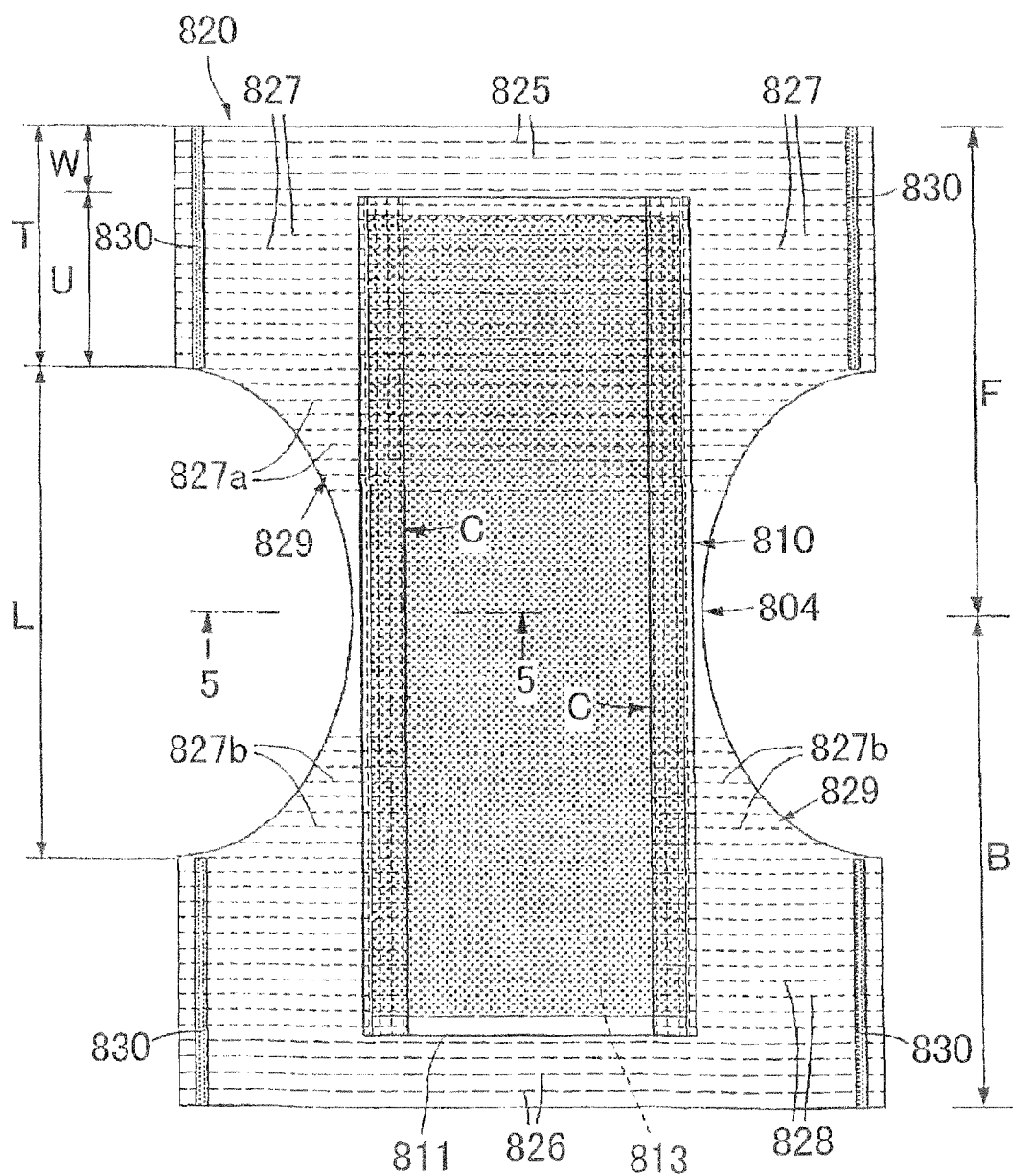
FIG. 41 is a plan view from a use surface side showing a development of a pant-type of disposable diaper according to the eighth embodiment of the invention.

As shown in FIG. 41, contrary to the fifth embodiment, the eighth embodiment provides a formation of the shaping elastic members, in such a way that the shaping elastic member 827a of the front side section F is continuously formed from the leg opening edges 829 of one side to the other, the shaping elastic member 827b of the back side section is continuously formed respectively from both leg opening edges 829, 829 to the position corresponding to the absorbent core, excluding the central portion of the absorbent core 813. In an example shown in the figure, continuation or discontinuity of the elastic members of the lower waist sections 827, 828 are formed in agreement with the elastic members 827a, 827b of the front and back side section, and formed conversely to the fifth embodiment.

Ninth Embodiment

Figure 42:
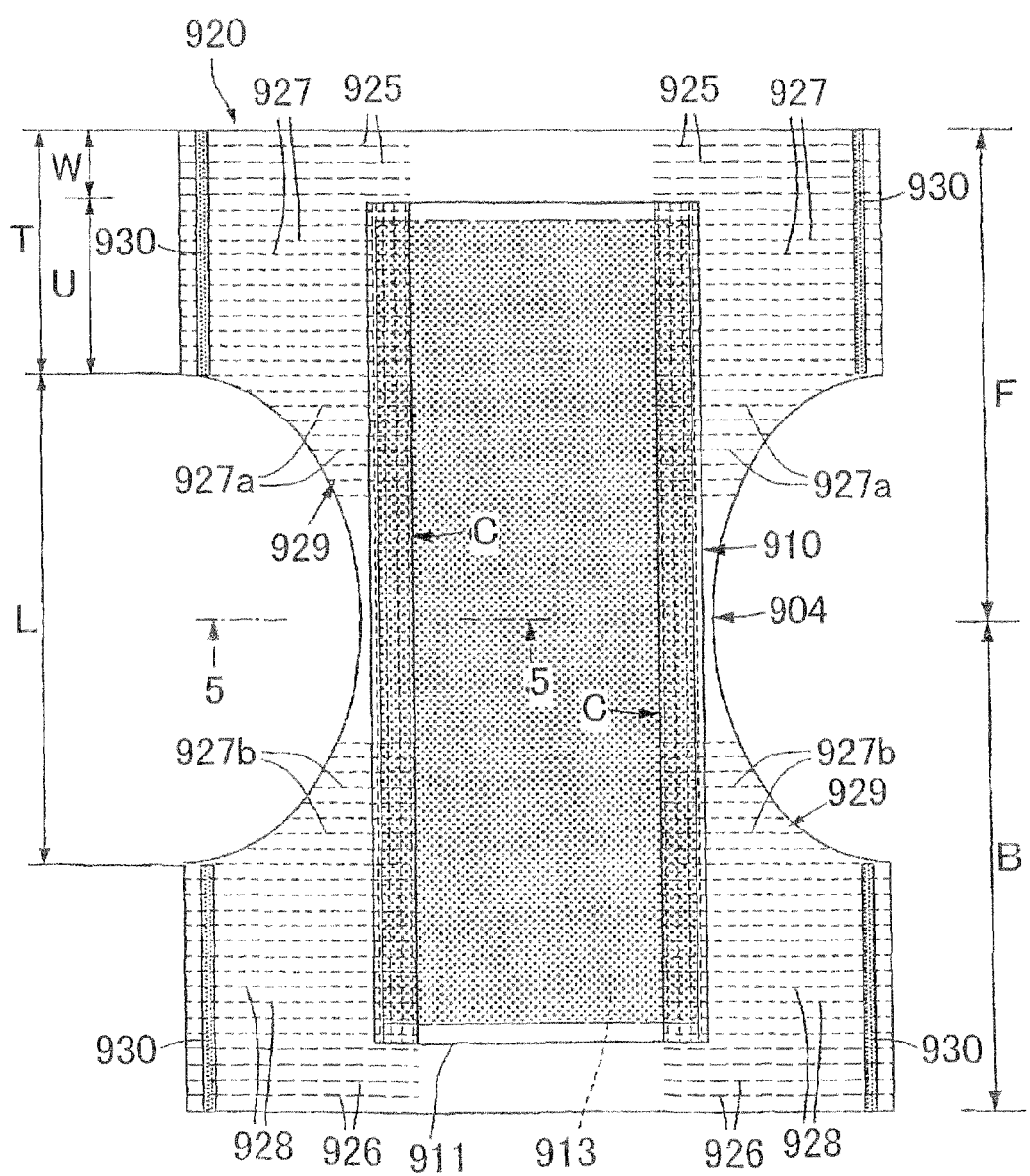
FIG. 42 is a plan view from a use surface side showing a development of a pant-type of disposable diaper according to the ninth embodiment of the invention.

As shown in FIG. 42, the ninth embodiment provides a formation of the shaping elastic members in such a way that both shaping elastic members 927b of the front side section F and the shaping elastic members 927b of the back side section B are continuously formed from both leg opening edges 929, 929 to the position corresponding to the absorbent core respectively, excluding the center of the absorbent core 913. In an example shown in the figure, both of the waist section elastic members 925, 926 and both of the under waist section elastic members 927, 928 include discontinuous portion in the center respectively in agreement with the shaping elastic members 927a, 927h.

Tenth Embodiment

Figure 43:
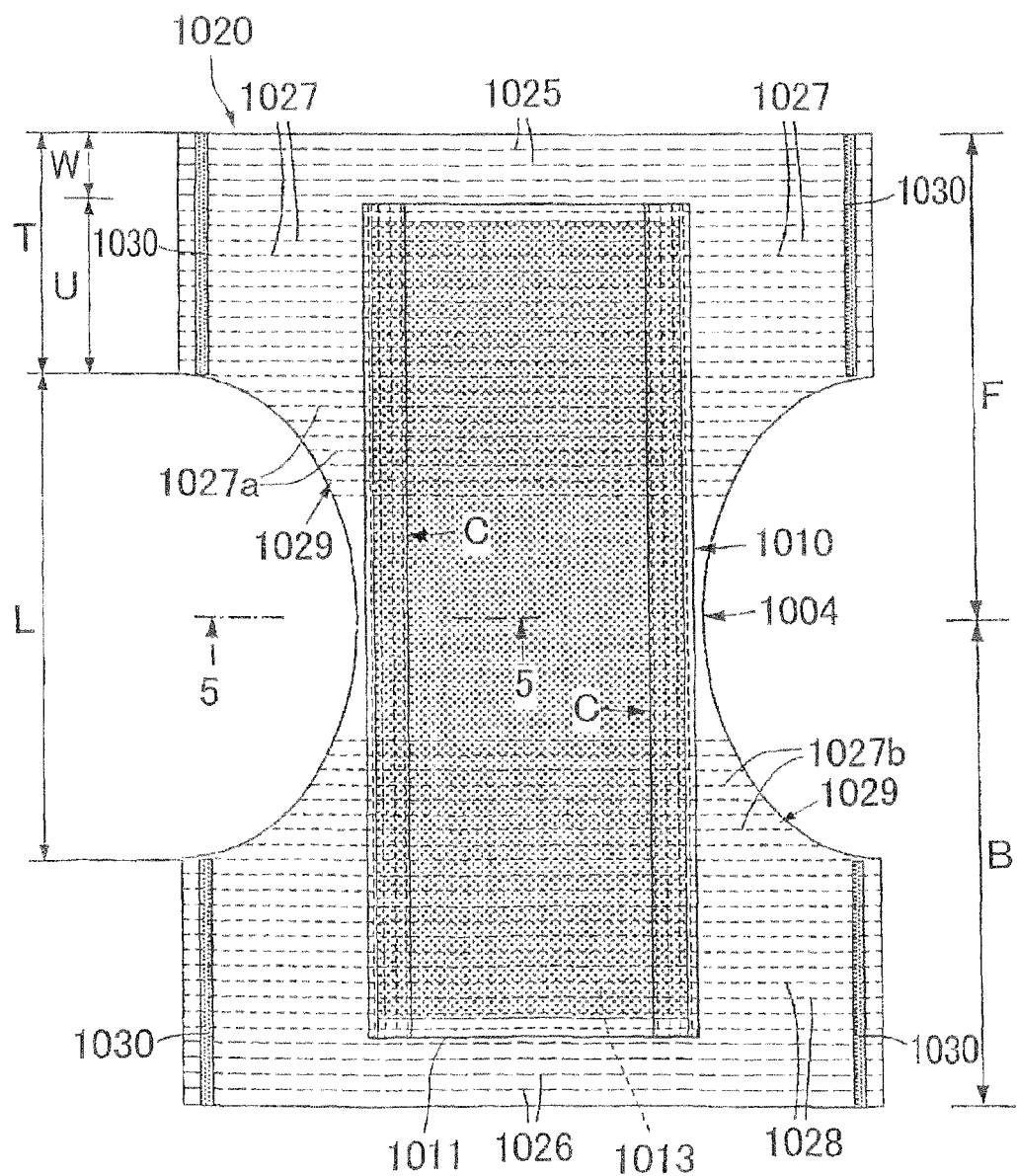
FIG. 43 is a plan view from a use surface side showing a development of a pant-type of disposable diaper according to the tenth embodiment of the invention.
Figure 44:
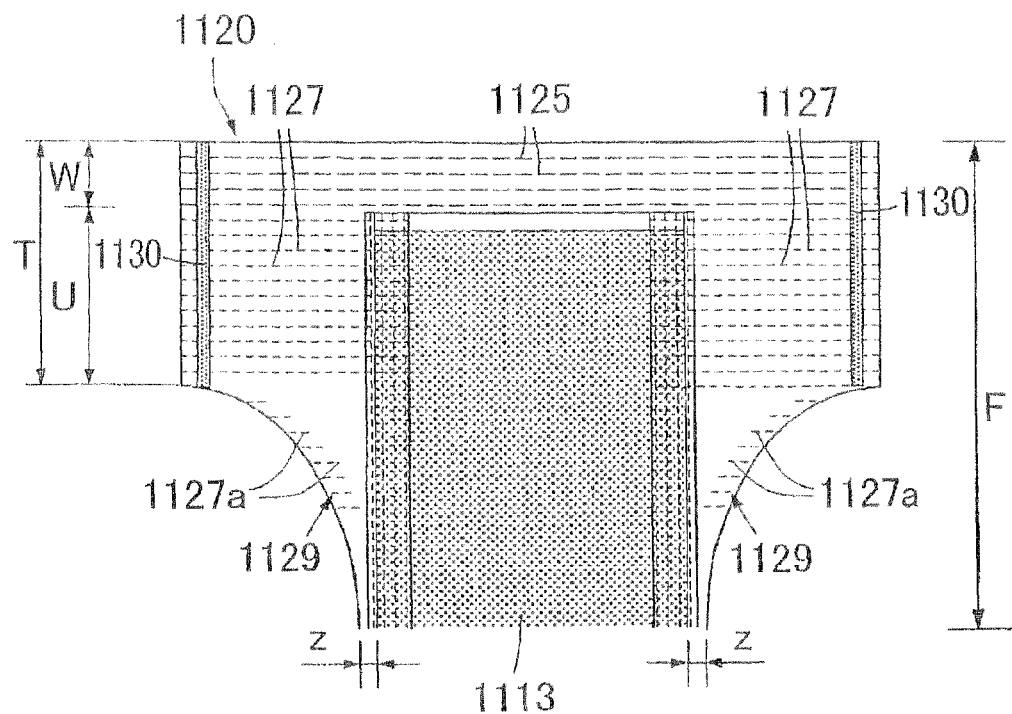
FIG. 44 is a plan view from a use surface side showing a development of a pant-type of disposable diaper according to the eleventh embodiment of the invention.

As shown in FIG. 43, the tenth embodiment provides a formation of the shaping elastic members in such a way that both of the front side section F of the shaping elastic member 1027a and the back side section B of the shaping elastic member 1027b are formed continuously from the leg opening edges 1029 one side to the other. In an embodiment shown in the figure, both of the waist section elastic members 1025, 1026 and both of the under waist section elastic members 1027, 1028 are formed continuously from the girth region T of one joint portion to the other joint portion, in agreement with the shaping elastic members 1027a, 1027b.

Eleventh Embodiment

In the shaping elastic members of the invention, as shown in the embodiment of the front side section F, the shaping elastic members may be formed so as to extend from the leg opening edges of the crotch region L only up to the position in the vicinity of the absorbent core, preferably only to the position spaced by 5 mm, especially by 2 mm from the absorbent core 1113. In an embodiment of the figure, the spaced distance is denoted by "z". The formation of the shaping elastic members described above may be applicable to either front side section of the shaping elastic member 1127a, or back side section B of the shaping elastic member 1127b.

Twelfth Embodiment

Figure 45:
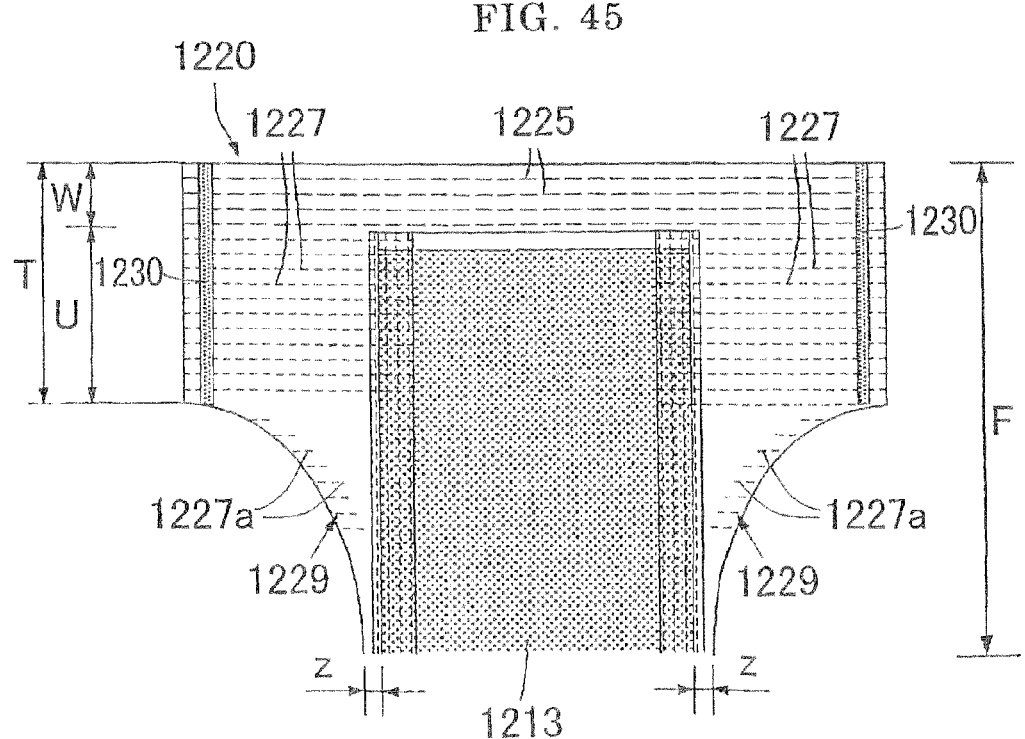
FIG. 45 is a plan view from a use surface side showing a development of a pant-type of disposable diaper according to the twelfth embodiment of the invention.

As shown in an embodiment of the front side section F of the shaping elastic member 1227a in FIG. 45, for example, the shaping elastic members of the invention can be formed in the leg opening edges 1229, 1229 of the crotch region L only. The formation of the shaping elastic members described above may also be applicable to either front side section of the shaping elastic member 1227a, or back side section B of the shaping elastic member 1227b.

Thirteenth Embodiment

Further, in the embodiment given above, the shaping elastic members 1227a, 1227b are not formed in a length range R of 2 to 3 cm, especially 4 to 6 cm in the front and back portions of the crotch portion 4. However, the shaping elastic member of the invention can be formed in the whole portion of the crotch region L in the longitudinal direction.

Figure 46:
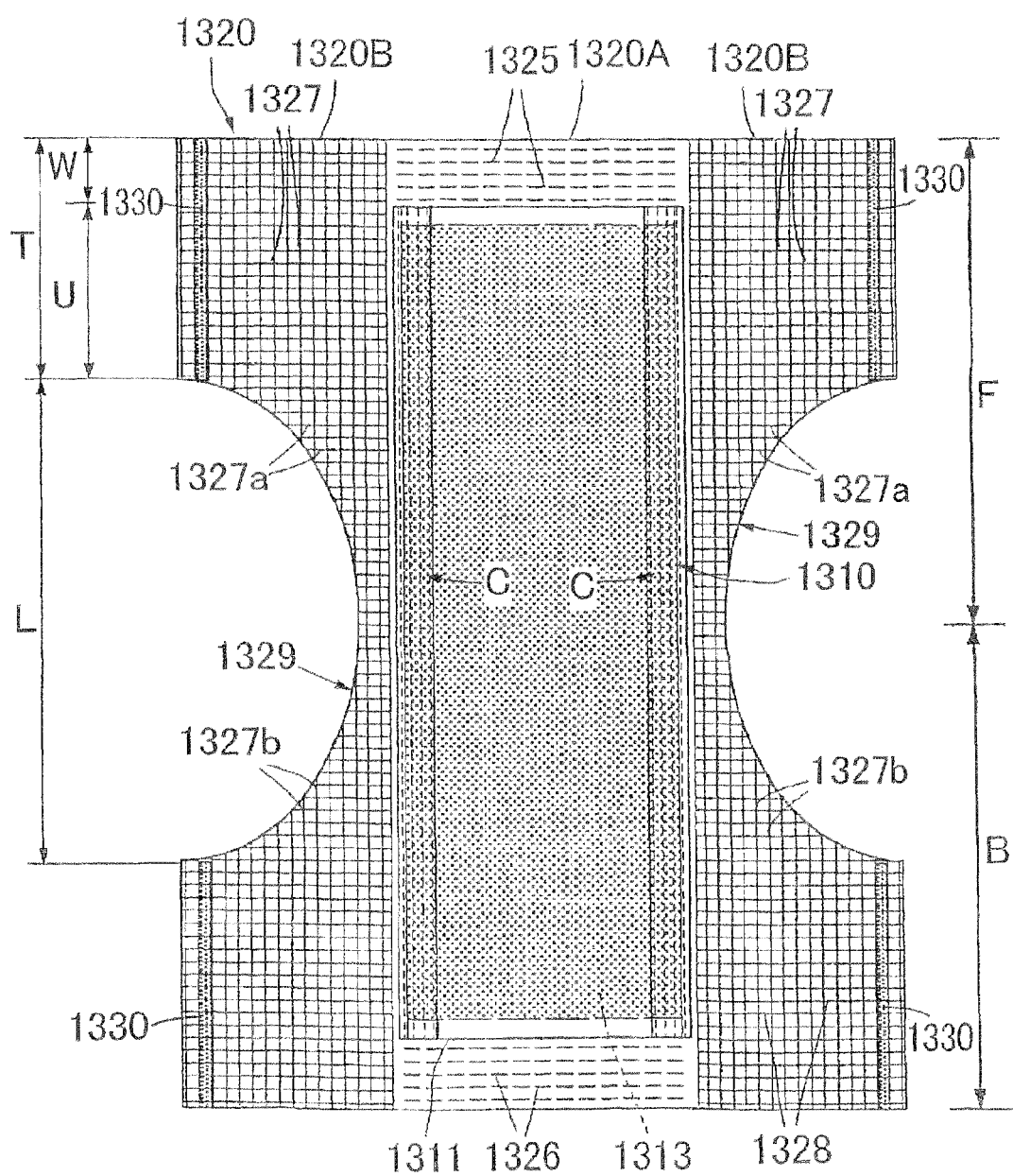
FIG. 46 is a plan view from a use surface side showing a development of a pant-type of disposable diaper according to the thirteenth embodiment of the invention.

One embodiment of this formation is shown in FIG. 46. In the thirteenth embodiment, the external sheet 1320 is formed of central sheet 1320A of the width direction and side sheets 1320B, 1320B of both sides, wherein each side sheet 1320B, 1320B employs thin rubber thread fixed in a shape of lattice or net. And the side sheets 1320B, 1320B of both sides are bonded to the central sheet 1320A in the width direction, wherein each side sheet 1320B, 1320B are set so as to expand or contract in the width direction and longitudinal direction. The thin rubber thread used in this case, forms not only the elastic members of the waist section W, and lower waist section U, but also the shaping elastic members of the invention.

Fourteenth Embodiment

Figure 47:
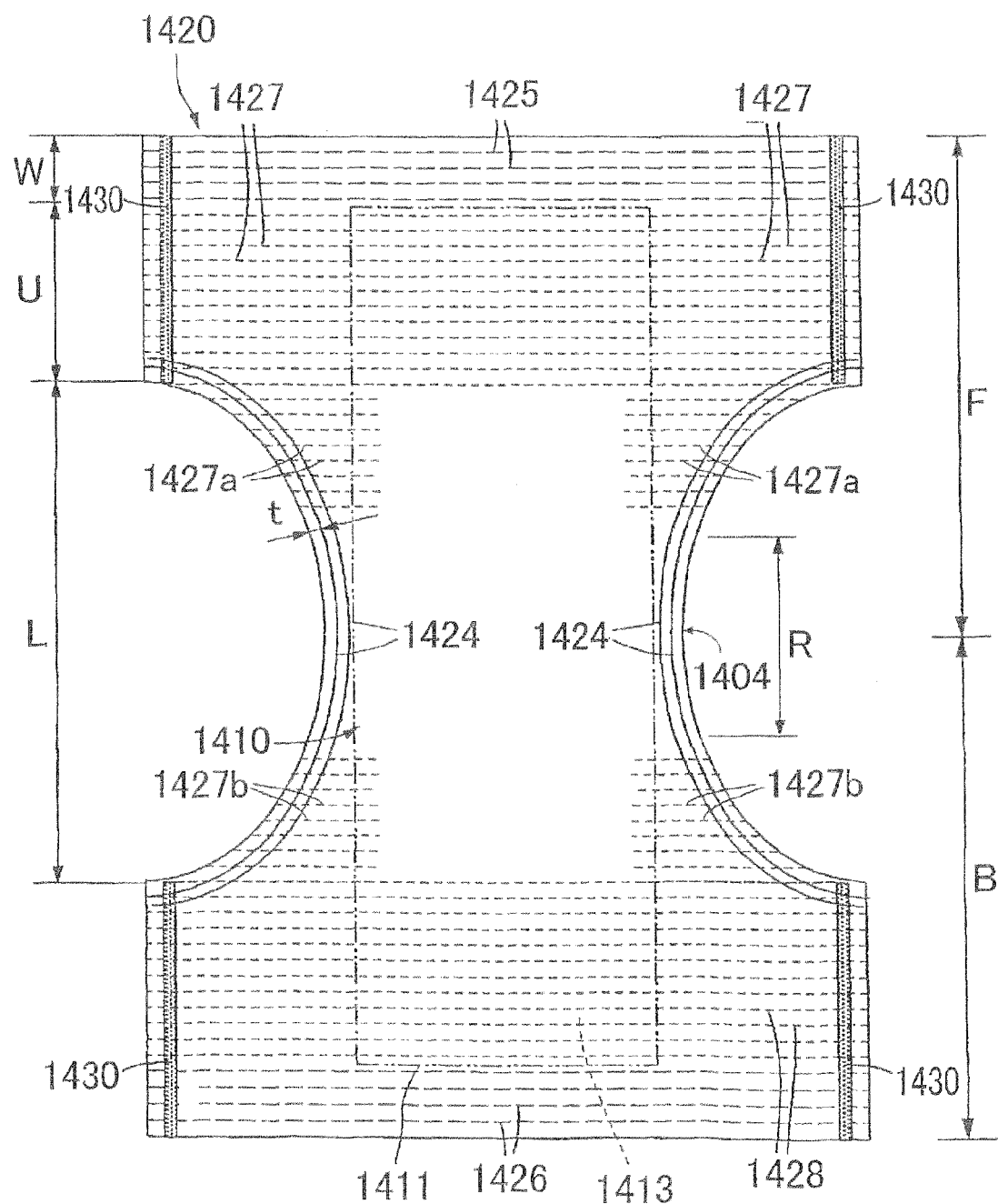
FIG. 47 is a plan view from a use surface side showing a development of a pant-type of disposable diaper according to the fourteenth embodiment of the invention.

In the invention, in addition to the shaping elastic members, the elastic members of various formations can be formed in the external sheet 1420, in order to obtain a fitting property of the crotch portion. In the fourteenth embodiment, as shown in FIG. 47, in addition to the shaping elastic members 1427a, 1427b, the leg section elastic members 1424, 1424 formed continuously along the leg openings are fixed to the nonwoven fabric of the external sheet 1420. In the invention, protrusion breadth t of the leg opening edges 1429, 1429 from the leg section elastic members 1424, 1424 is preferably 5 mm or less (more preferably 2 mm or less). In addition, in FIG. 47, the paper diaper main body 1410 is shown by phantom (the same with embodiments shown in FIG. 48 and FIG. 49, as described above).

The elastic member 1424 described above is formed in order to prevent lateral leakage of body fluid by shrinkage of the leg openings LO generally. However, protrusion breadth t of the leg opening edges 1429, 1429 from the leg section elastic members 1424, 1424 is set to 5 mm or less, to thereby provide a paper diaper which makes leg opening edges hardly flutterable and make portions around the legs neat and attractive, by obtaining combined effect with the shrinkage of the leg opening edges by the shaping elastic members 1427a, 1427b.

Fifteenth Embodiment

Figure 48:
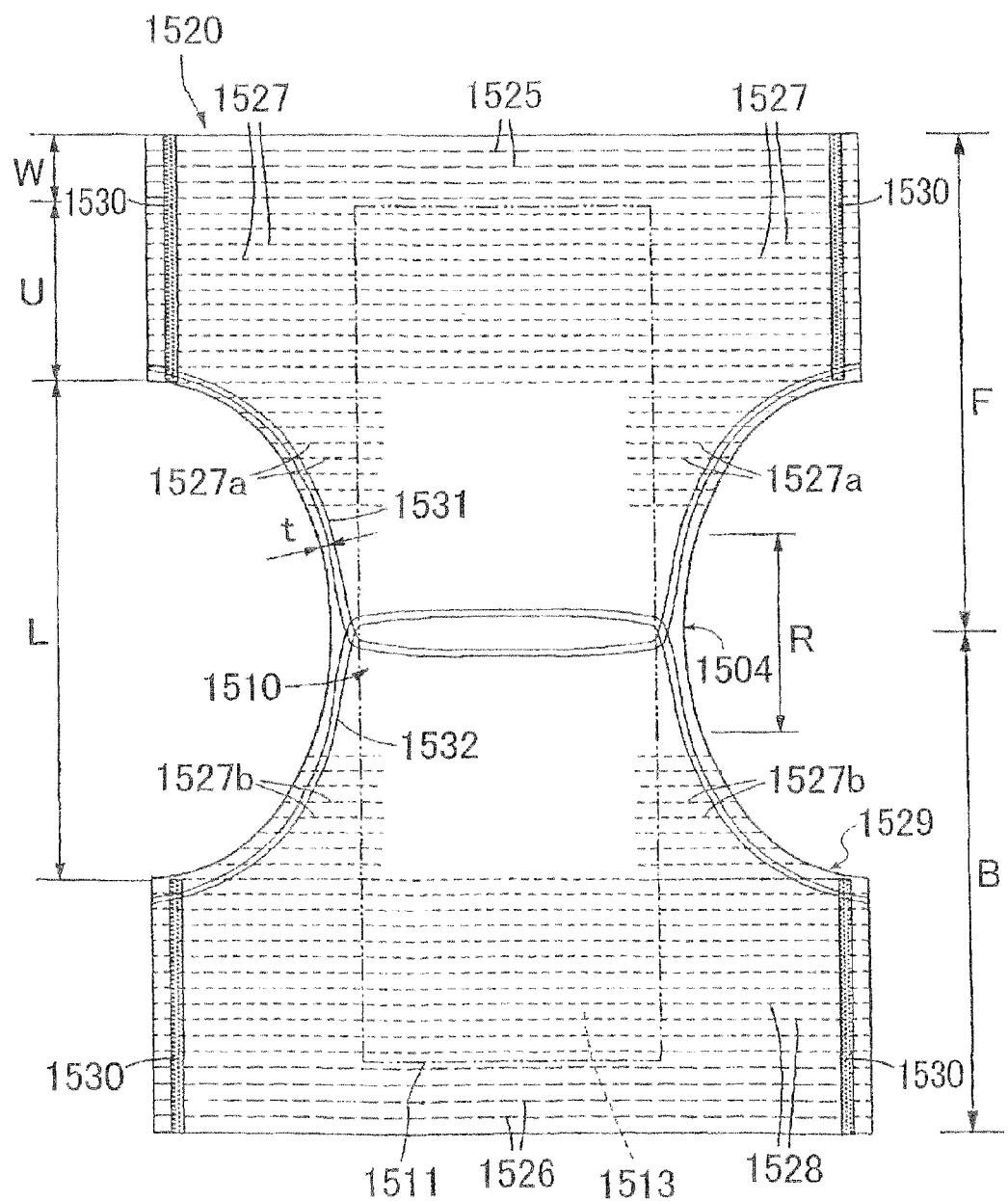
FIG. 48 is a plan view from a use surface side showing a development of a pant-type of disposable diaper according to the fifteenth embodiment of the invention.

In the fifteenth embodiment, as shown in FIG. 48, in the front side section F and the back side section B, the leg section and crotch section elastic members 1531, 1532 are fixed between nonwoven fabrics of the external sheet 1520 by continuously extending from the edge of the left side portion, across the crotch (lower crotch) section, and through the leg opening edge 1529 of right side to the edge of the right side portion. Also, in this embodiment, the leg section and crotch section elastic members 1531, 1532 of the front side section F side and the back side section B side are partially crossed in the range of 2 to 3 cm, especially 4 to 6 cm in the front and back portions of the crotch section 1504.

In the above formation, when protrusion breadth t of the leg opening edges 1529, 1529 from the leg section elastic members 1531, 1532 is preferably 5 mm or less (more preferably 2 mm or less), a paper diaper which makes leg opening edges 1529 hardly flutterable and makes portions around the legs neat and attractive, as similar to the fourteenth embodiment, is produced.

Sixteenth Embodiment

Figure 49:
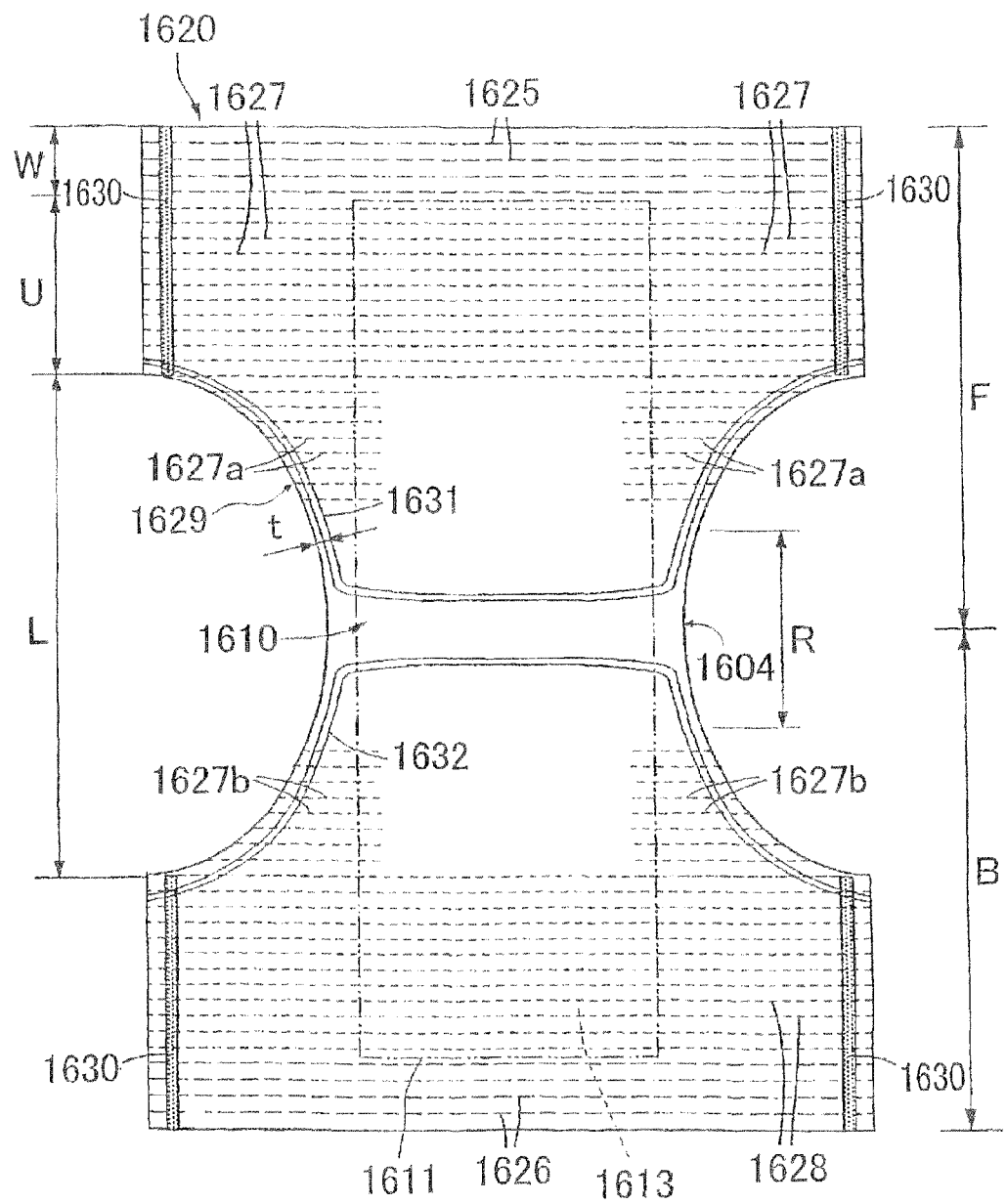
FIG. 49 is a plan view from a use surface side showing a development of a pant-type of disposable diaper according to the sixteenth embodiment of the invention.

As shown in FIG. 49, in the sixteenth embodiment, difference from the fifteenth embodiment resides in that the leg section and crotch section elastic members 1631, 1632 of the front side section F side and the back side section B side are formed in the front and back portions of 2 to 3 cm, especially 4 to 6 cm of the range R of the crotch section 1604, but not crossed therein. In the above formation, when protrusion breadth t of the leg opening edges 1629, 1629 from the leg section elastic members 1631, 1632 is preferably 5 mm or less (more preferably 2 mm or less), a paper diaper which makes leg opening edges 1629 hardly flutterable and makes portions around the legs neat and attractive, as similar to the fourteenth embodiment, is produced.

[Supplementary Explanation about Each Form of Pant-Type of Disposable Diaper, and Other Embodiment]

In order to enable an examination by comparing, the shaping elastic members of the invention adopts an arrangement form of the shaping elastic members which is continuously formed and traverse the paper diaper main body to be fastened in parallel to the under waist section, and the arrangement form of the shaping elastic members which is fastened to only the right and left side portions of a product without extending the whole portion of the absorbent core. Also, the shaping elastic members in the front side section are not formed in approximately the whole portion of the absorbent core, but arranged and fastened to only right and left side portions of a product, while the shaping elastic members of the back side section traverse the paper main body and can be arranged and fastened continuously in parallel to the under waist section. Of course, vice versa is satisfactory.

In addition, especially the protrusion breadth from the absorbent core in the leg opening edges of the back side section B is apt to be long and flutterable compared with that of the front side section F. Therefore, the shaping elastic members are preferably formed at least in the leg opening edges of the back side section. In such a case, however, the shaping elastic members in the front side section F can be omitted. Of cause, to the contrary, only front side section F can have the shaping elastic members formed thereon.

Further, when including the rising cuffs C as described in the above embodiment, side edge of the absorbent body main body is shrunk by the thread-shaped elastic members 516, 516 . . . in the direction of the leg section, therefore, the surplus leg opening edges in the side direction are further flutterable. Therefore, the invention is especially preferable to the disposable diaper including the rising cuffs.

Also, it is preferable that the leg section is cut so as to be entered inwardly or stretched out outwardly by 5 to 15 mm, or especially 5 to 10 mm, from the rising end when the crotch side end section of the external sheet includes a rising cuff C, and from side end of the absorbent core, when the crotch side end section of the external sheet includes no rising cuff. Thereby, surplus portion of the external sheet becomes smaller, and the combined effects of the shaping elastic members of the invention are provided, presenting the leg opening edges hardly flutterable.

On the other hand, as for the waist section elastic members and the under waist section elastic section members, whether they are needed to be formed or not, or whether they are formed continuously or discontinuously, is suitably selected.

In the above embodiment, rectangular main body of a paper diaper is bonded to the sandglass-shaped external sheet. However, in the invention, the above embodiment shows that the liquid permeable top sheet of the same form with the external sheet is formed by laminating two or three or more nonwoven fabrics having air permeability and water repellent property to be fastened. However, one nonwoven fabric is also satisfactory, and in this case, elastic members 527, . . . , 528, . . . are bonded to the use surface of the nonwoven fabric. Furthermore, a plastic sheet can be interposed in a middle section of the laminated nonwoven fabrics or can be laminated face to face on the use surface of the back side of the nonwoven fabrics.

Figure 50A:
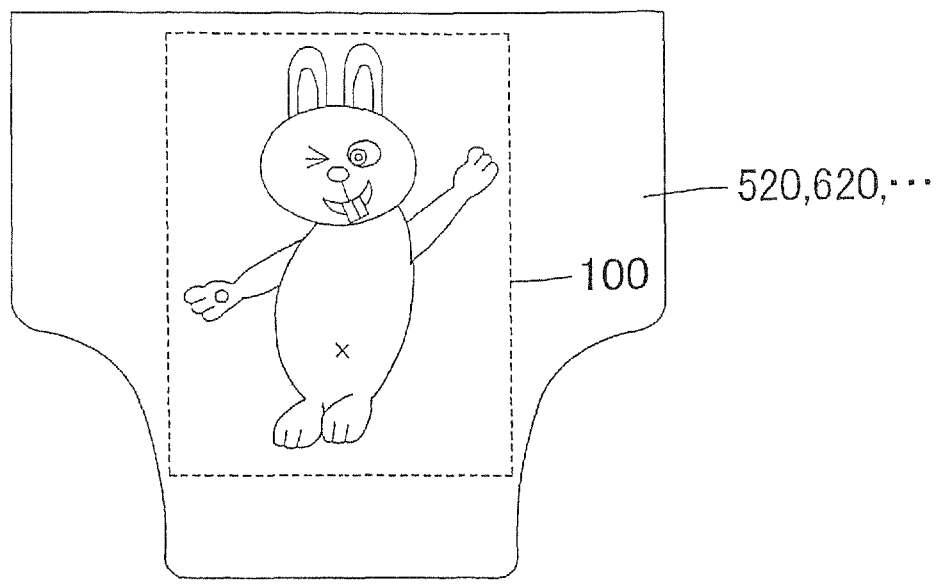
FIG. 50(A) and FIG. 50(B) are views showing an embodiment of a design of both sides of a product.
Figure 50B:
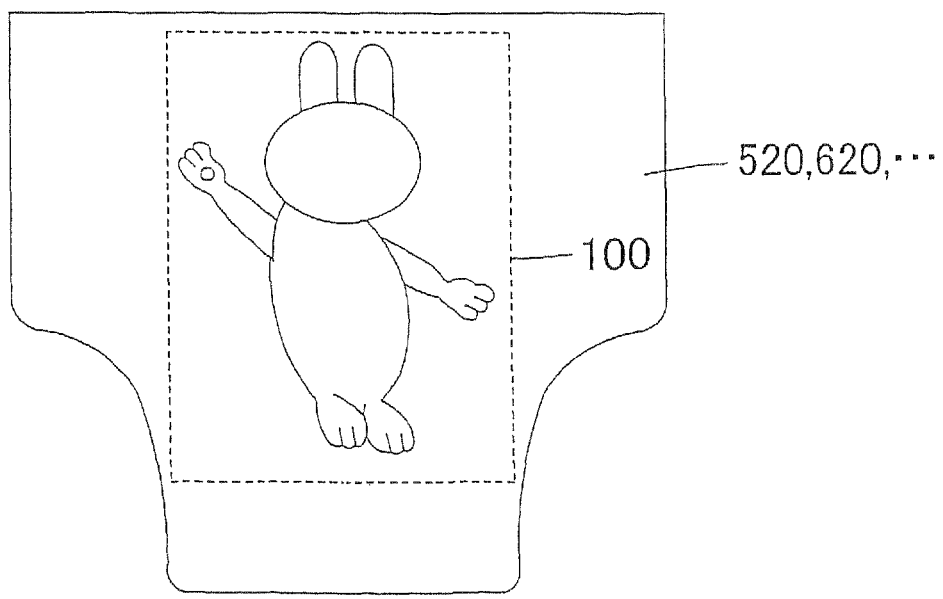

On the other hand, in the central portion of a product (approximately the whole region of the absorbent core), as shown in FIG. 50A, and FIG. 50B, design sheet 100 is included so that character or the like can be designed on the external surface of the design sheet 100. The design portion includes the absorbent core having a certain amount of rigidity, and the external sheet (520, 620 . . . ) does not change in form or wrinkles are not produced according to the invention, therefore it can be recognized vividly without the design collapsing. The design sheet 100 can be interposed between the external sheet. In addition, it can be printed on the external sheet or can be printed on the back side of the leakage preventing sheet (512 . . . ). Further, as shown in the figure, if the front and the back of the character are determined corresponding to the front and the back of a product, distinction of front and back is easy so as to be distinguished by anyone at a glance. A diaper change becomes pleasant and is pleased also by a wearer. The constitution according to the above design is applicable also to the tape fastening disposable diaper as will be explained hereafter.

Seventeenth Embodiment

Figure 51:
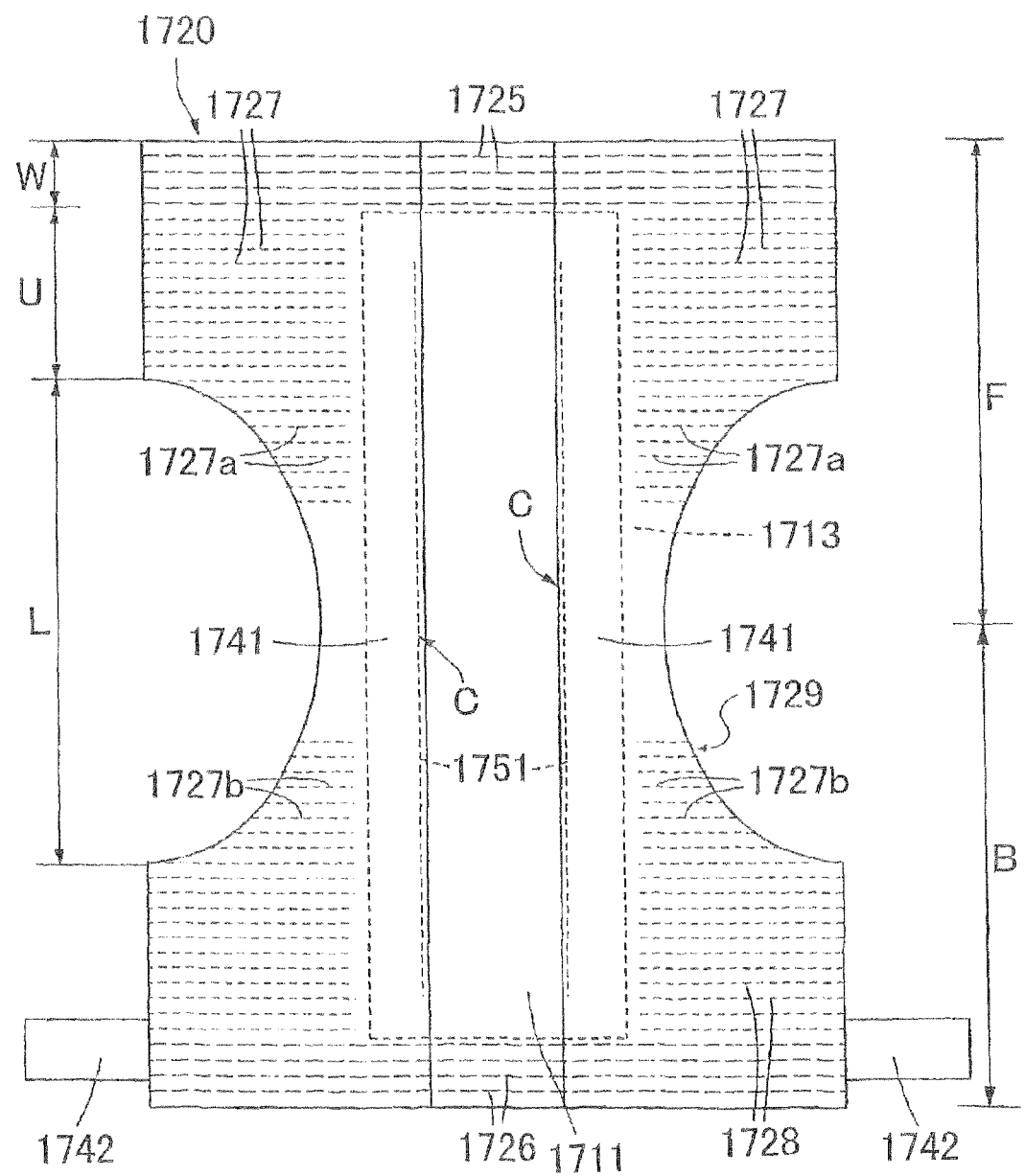
FIG. 51 is a plan view from a use surface side showing a development of a pant-type of disposable diaper according to the seventeenth embodiment of the invention.
Figure 52:
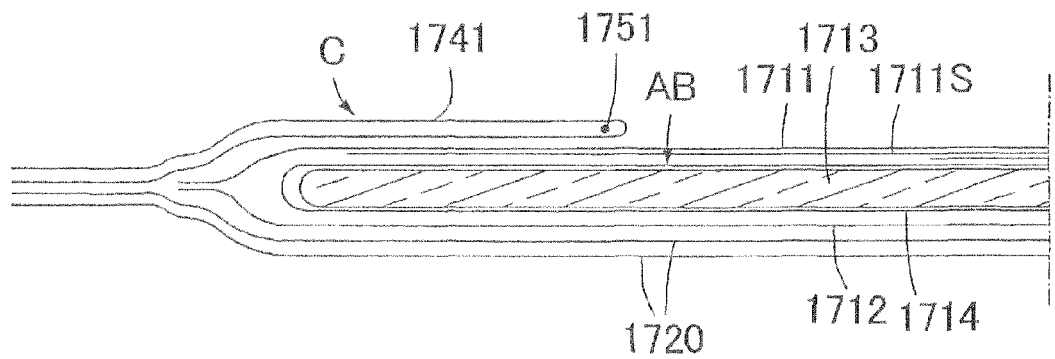
FIG. 52 is a vertically sectional view of the central portion in the crotch region of a tape type of paper diaper according to the seventeenth embodiment.

As describe above, the invention also targets a tape type disposable diaper in addition to a pant-type of disposable diaper. The seventeenth embodiment is shown in FIG. 51 and FIG. 52. This embodiment includes rising sheets 1741, 1741 on both sides, and elastic members 1751, 1751 on tip end portion of the free rising portion, to thereby form the rising cuffs C, C. The rising sheet 1741 is bonded to back side sheet 1720 that is similar to the external sheet. 1742 is a tape fastener for joint of right and left side edges by bringing both right and left side portions of the back side to the right and left side portions of the belly side to be matched. In this embodiment, in the edge of the longitudinal direction of the front side section F and the back side section B, and between nonwoven fabrics of the external sheet 1720 in the waist portion W, the waist section elastic members 1725, 1726 . . . composed of thin rubber thread are arranged and fastened in a state of being elongated, so as to be expanded and contracted, keeping an space in parallel to the edges of the waist opening portion WO, in order to improve fitting property of the waist section. Further, the under waist section elastic members 1727, 1728 are formed at lower belly section of the front side section F and at buttock section of the back side section B along the body peripheral direction.

And the shaping elastic members 1727a, 1727b of the invention are formed by extending from the leg opening edges 1729, 1729 in the crotch region T to the position near the absorbent core 1713 in parallel to the under waist section, excluding a range corresponding to the whole portion of the absorbent core 1713 where no shaping elastic members are formed.

Eighteenth Embodiment

Figure 53:
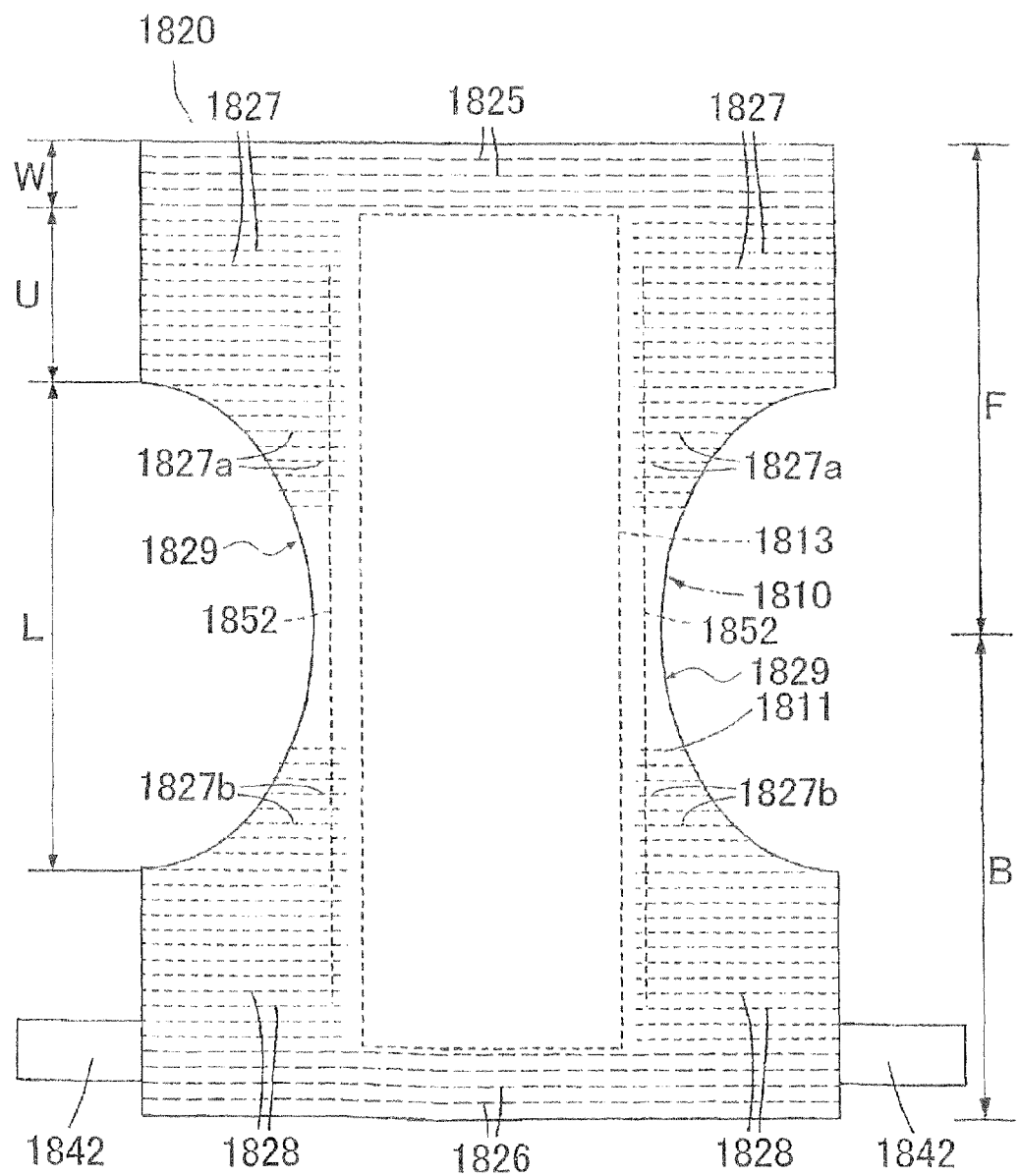
FIG. 53 is a plan view from a use surface side showing a development of a pant-type of disposable diaper according to the eighteenth embodiment of the invention.
Figure 54:
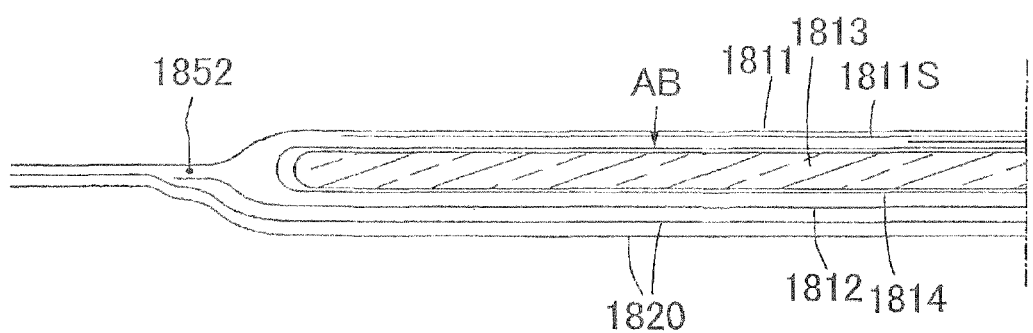
FIG. 54 is a vertically sectional view of the central portion in the crotch region of a tape type of paper diaper according to an eighteenth embodiment.

The eighteenth embodiment is shown in FIG. 53 and FIG. 54. An embodiment including no rising cuffs is shown here. And the elastic members 1852, 1852 are fastened to outside flap portions of the absorbent core 1813 between the liquid permeable sheet 1811 and the back sheet 1812. In this embodiment also, the waist section elastic members 1825, 1826, and the under waist section elastic members 1827, 1828 are formed.

And in this embodiment also, the shaping elastic members 1827a, 1827b of the invention are formed extending from the leg opening edges 1829, 1829 of the crotch region T to the position near the absorbent core 1813 in parallel to the under waist section, excluding the range corresponding to the whole portion of the absorbent core 1813 where the shaping elastic members are not formed.

(Elastic Member)

Figure 55:
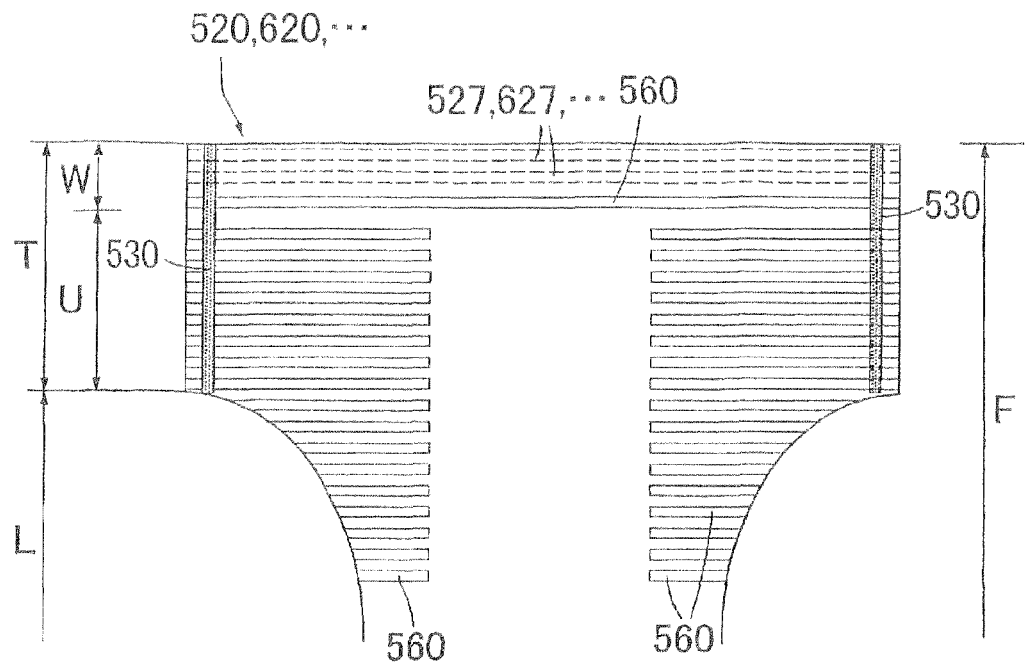
FIG. 55 is a plan view from a use surface side showing a development of a diaper in case of including other elastic members.
Figure 56:
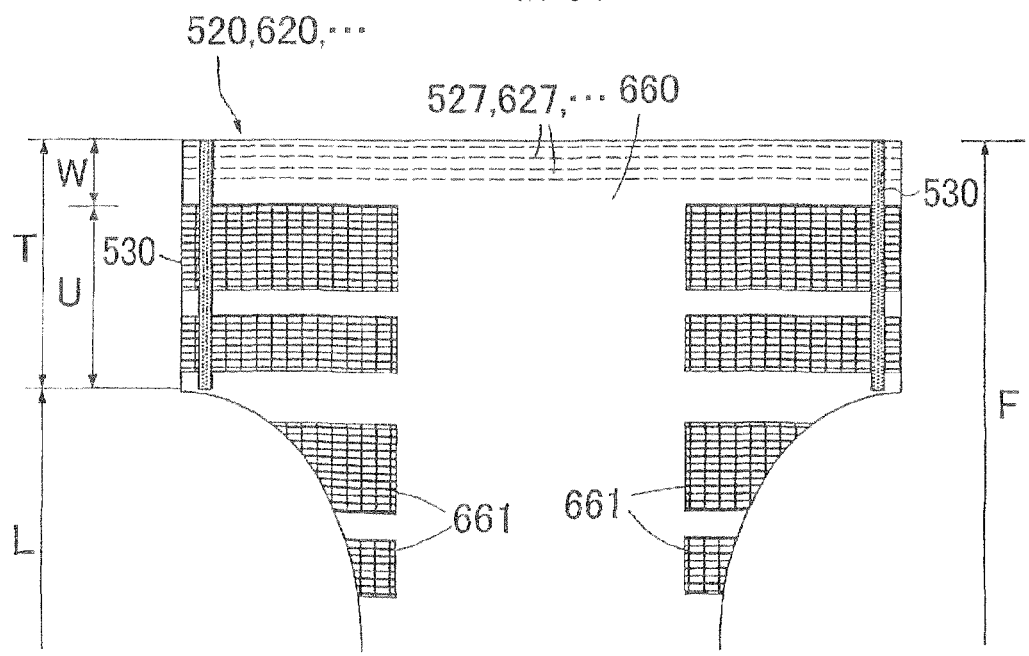
FIG. 56 is a plan view from a use surface side showing a development of a diaper in case of including other elastic members.

As each elastic members of the invention, in addition to materials such as a natural rubber and a synthetic rubber, the material having expansion and contraction elasticity such as urethane is also used. Also, a belt-like elastic member or a sheet-like elastic member having large area is also used. Embodiments of the above elastic members, belts such as urethane, films, and sheets, or the like are mentioned. As a film, a no-porous film or a porous film, and further as a sheet, a reticulated layered sheet can be suitably selected. An arrangement embodiment of the no-porous film 560 is shown in FIG. 55. Also, the arrangement embodiment of reticulated layered film 561 is shown in FIG. 56.

As described above, according to the above embodiments 5 to 18, advantages of a paper diaper such that leg opening edges are made so as to be hardly flutterable and portions around the legs are made neat and attractive are obtained.

Next, the nineteenth embodiment of the invention will be explained in detail taking a pant-type of disposable diaper as an embodiment first. Subsequently, a tape fastening type pant-type of disposable diaper, so to speak, for joint of right and left side edges by bringing both right and left side portions of the back side to the right and left side portions of the belly side to be matched by tape fastener (An adhesion agent tape fastener and a field fastener are included.) will be explained.

Nineteenth Embodiment

The disposable diaper according to the nineteenth embodiment of the invention will be explained in conjunction with FIG. 58 and FIG. 59, while giving term explanation about the portion and direction of the invention referring to FIG. 57.

Figure 57:
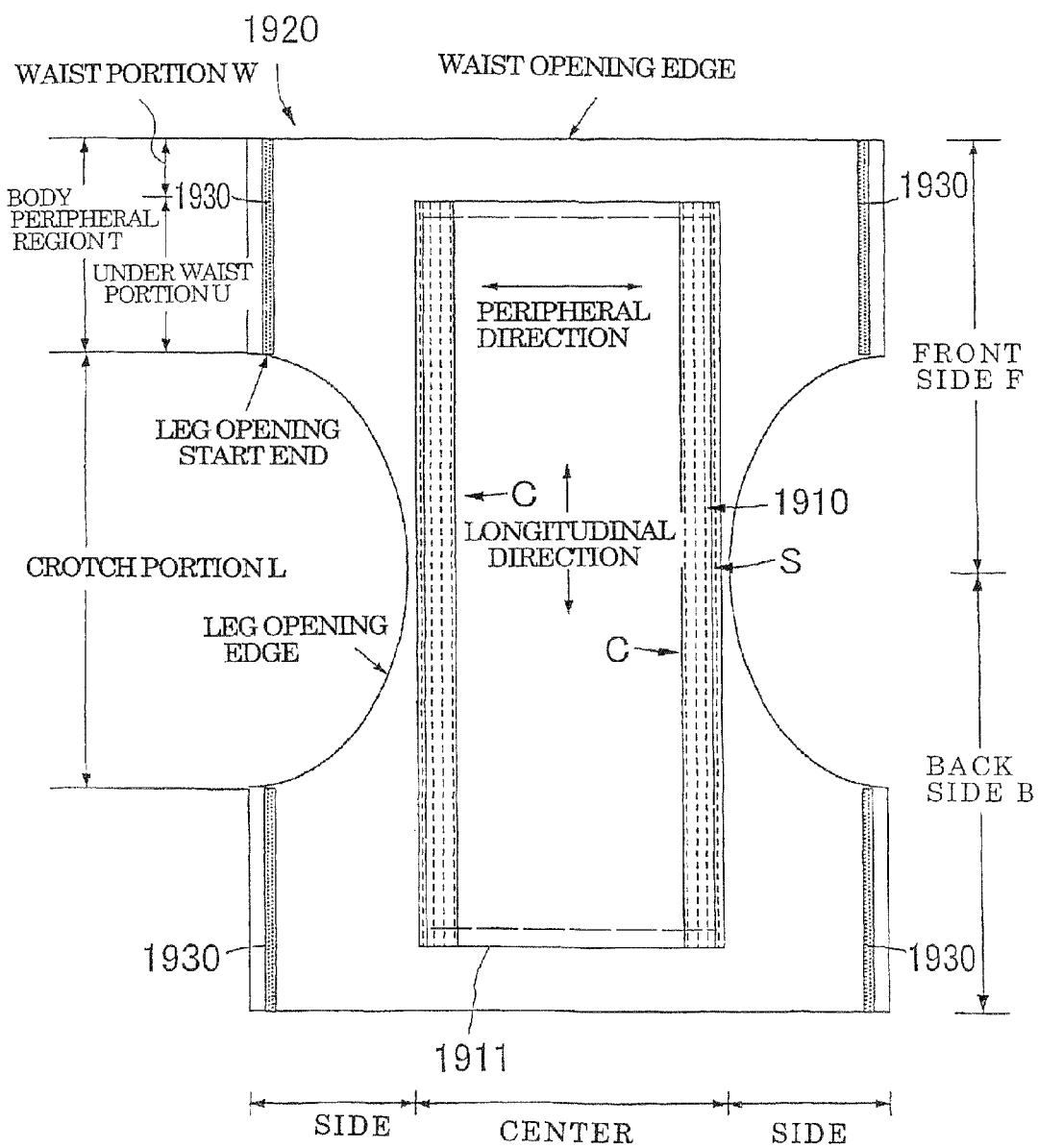
FIG. 57 is a plan view from a use surface side, showing a development of a pant-type of disposable diaper according to the nineteenth embodiment of the invention, in view of a term explanation.
Figure 58:
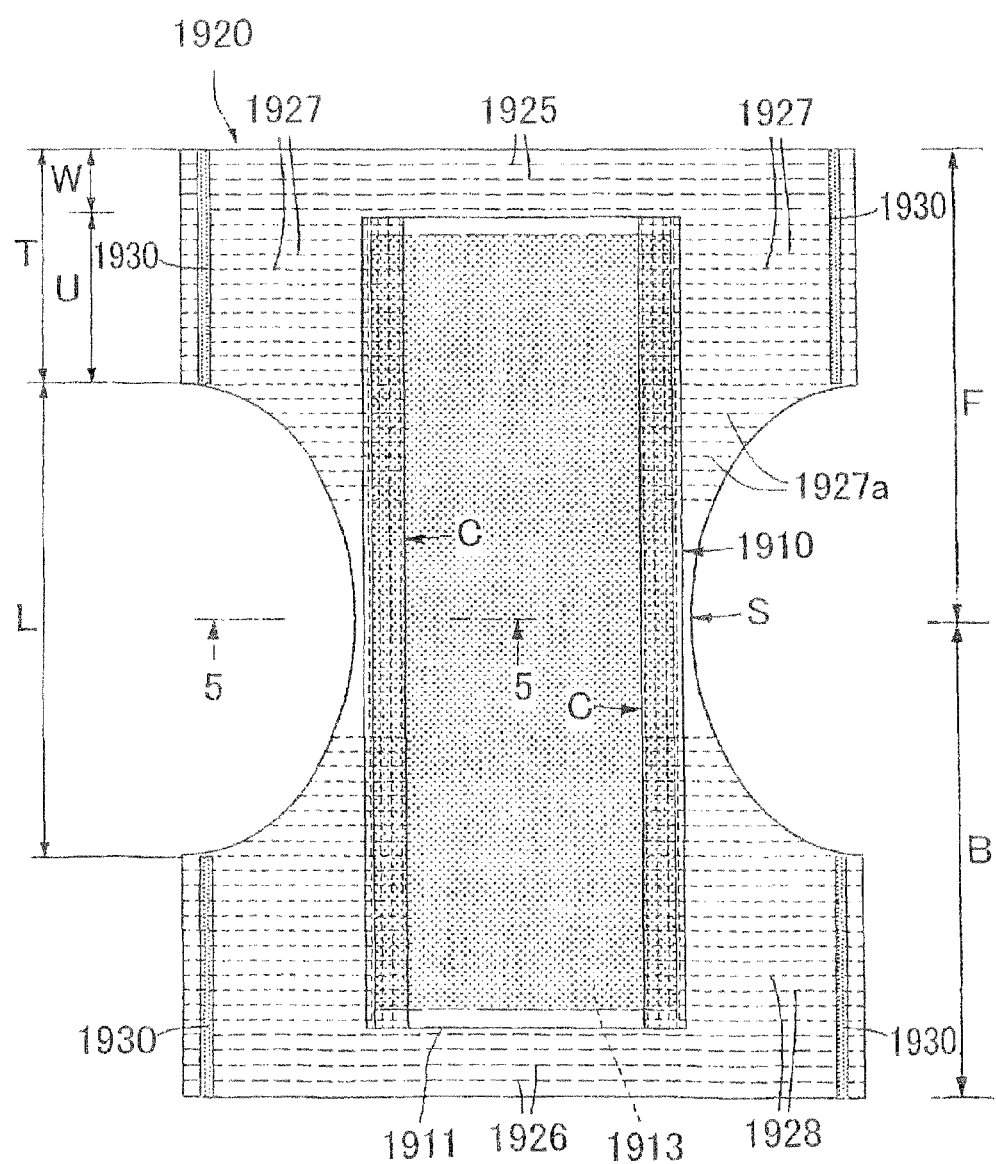
FIG. 58 is a plan view from a use surface side showing a development of a pant-type of disposable diaper according to the nineteenth embodiment of the invention.

As shown in FIG. 57 and FIG. 58, a pant-type of disposable diaper according to the nineteenth embodiment is mainly constituted by flexible external sheet 1920 and paper diaper main body 1910 extending across the crotch portion S in the longitudinal direction (front and back direction).

Figure 60:
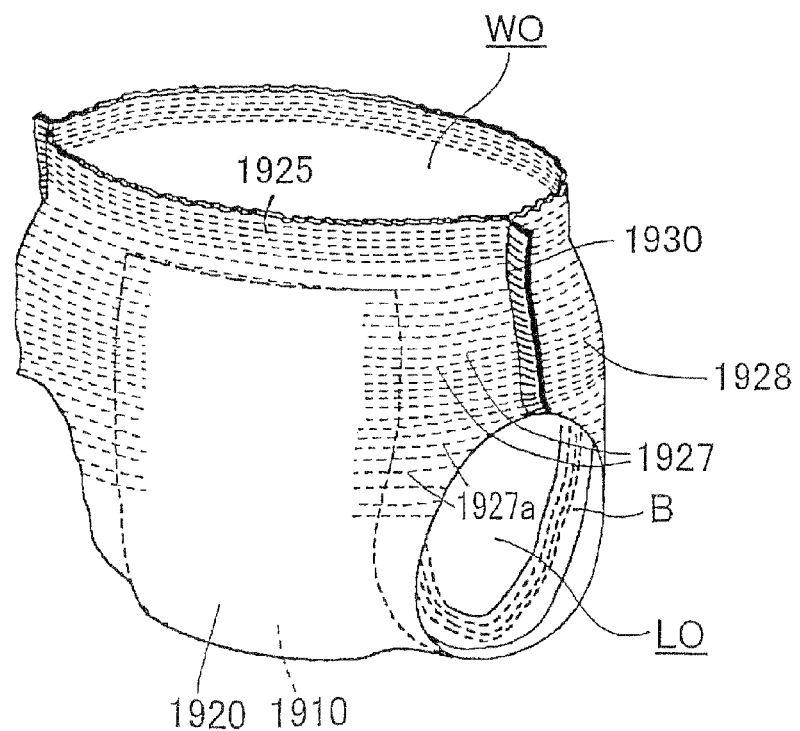
FIG. 60 is a perspective view of a product according to the nineteenth embodiment.

The external sheet 1920 is formed by laminating fixation of an air permeable and water-repellent nonwoven fabric of two sheets or three sheets or more. In the final stage of the manufacturing process after the external sheet 1920 is laminated on the paper diaper main body 1910, the whole longitudinal direction of both side edges of front side section F and back side section 5 are bonded by an ultrasonic seal method or a thermal fusion method (the joint portion is denoted as a reference numeral 1930) or the like, to thereby form waist opening portion NO and a pair of leg openings LO in right and left, as shown in FIG. 60.

As denoted in FIG. 57, "longitudinal direction" means the direction to connect a belly and back side, and "peripheral direction" means the direction that intersects with the longitudinal direction perpendicularly (or product width direction). "Waist opening edges" mean the edges of the waist opening WO, and a "leg opening edges" mean the edges of the leg opening LO. "Leg opening initial end" means the position which intersects the leg opening edges of the leg opening LO and joint portion 1930, meaning the beginning portion of the leg opening edges. The "body peripheral region" T means the whole length range region from the waist opening edges to the leg opening initial end. The body peripheral region T can be notionally divided into "waist portion" W and "under waist section" U. Length thereof in the longitudinal direction changes by sizes of a product, however the waist portion W is 15 to 40 mm and the under-waist section U is 65 to 120 mm. "Crotch region" L means the region forming the leg opening portions, that is, the whole region from the leg opening initial end of the front side section to the leg opening initial end of the back side section. Moreover, "Central portion or center" means the middle region including a central line of a product excepting a side portion. "Side portion" means both-sides portion in the body peripheral region T.

Figure 59:
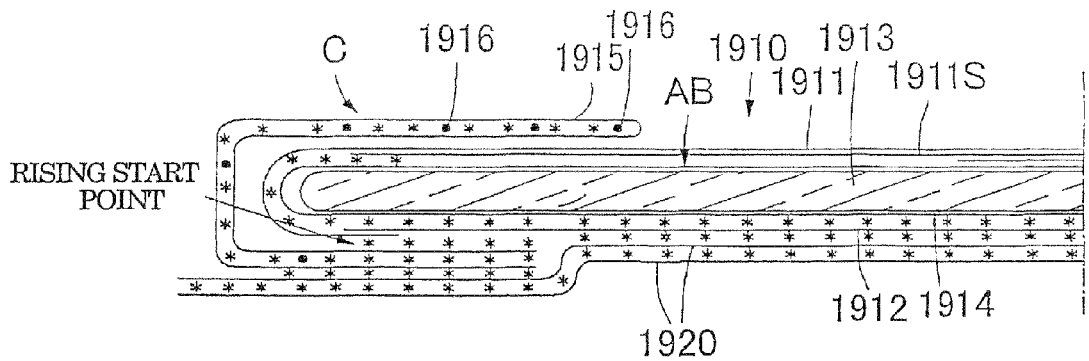
FIG. 59 is a sectional view taken along the line 5-5 thereof.

As shown in FIG. 59, the disposable diaper main body 1910 comprises a rectangular shaped liquid-permeable top sheet 1911 made of nonwoven fabric or the like which touches a wearer's skin directly; an absorbent body AB which comprises an absorbent core 1913 mainly composed of a cottony pulp and having a certain amount of rigidity (semi-rigid), and a rectangular shaped crepe paper 1914 that wraps the whole upper and lower surfaces of the absorbent core; and a rectangular shaped leakage preventing sheet 1912 composed of polyethylene plastic film or the like extending to the vicinity of both edges of the back side of the absorbent body AB. The liquid-permeable top sheet 1911 extends around the outside of the side edges of the absorbent body AB to reach the back side thereof, and laminated on the leakage preventing sheet 1912. Each of these elements is integrally bonded (joint portion is specified by * in the figure) by a hot-melt adhesive.

Leg section rising cuffs C and C for portions around legs projecting toward a use face of the paper diaper main body 1910 are formed on both sides. The rising cuff C is formed of a raising sheet 1915 continuous in the width direction and one or a plurality of elastic expansion members 1916, 1916 . . . made up of thin rubber thread or the like.

More specifically, the rising cuff C is formed double by folding inwardly the raising sheet 1915 so as to wrap each elastic expansion member 1916, 1916 . . . fastened by a hot melt adhesive or the like. The raising sheet 1915 having each rising cuffs C and C formed thereon is preferably not permeable but non-permeable, or hydrophobic. In addition, the liquid permeable top sheet such as nonwoven fabric may be subjected to silicon processing, so that water-repellent property is added thereto. Furthermore, air permeability steam permeability is preferably presented. A liquid non-permeable film sheet may be sandwiched between the raising sheets 1915, to improve the water-proof property.

The inner surface of the double raising sheet 1915 extends to the back side of the absorbent body AB and leakage preventing sheet 1912, and is bonded by a hot-melt adhesive or the like to be fastened thereto. Consequently, the fastening initial end of the double raising sheet 1915 forms the rising ends of the rising cuff C.

In the side nearer to the top end than the rising end, free portions, which are not fastened to a product main body, is formed.

On the other hand, at both ends of the longitudinal direction, the free portions are fastened by a hot-melt adhesive to the product, more specifically to outer surface of the liquid-permeable sheet 1920. The tip end of the rising portion is heading from the rising end to the center side of a product.

In addition, at least one of thread-shaped elastic members 1916, 1916 is included in the free portion as a basic form. Especially, the thread-shaped elastic members 1916 are preferably included in the tip end of the free portion. Further, as shown in FIG. 59, the thread-shaped elastic members 1916 are preferably included in a root side. In the edge, as shown in the figure, a plurality of thread-shaped elastic members are preferably included.

FIG. 58 is a view showing a paper diaper in an development state in the longitudinal direction. The paper diaper is fitted into human body in a boat-shaped form, and expansion and contraction elasticity of each thread-shaped stretchable members 1916, 1916 . . . works. Therefore, in the leg section, the rising cuff C is raised by the contraction force of each thread-shaped elastic members 1916, 1916 . . . . At this time, the side portion of the disposable diaper main body 1910 is changed in form and raised, and the absorbent body AB is also changed in form and raised, to thereby form a deep pocket space.

The space surrounded by right and left rising cuffs C and C forms a body fluid retaining pocket. If urinating in this space, the urine is absorbed in the absorbent body element AB through liquid permeable top sheet 1911, and as for a solid portion of the excretion liquid, the rising cuff C serves as barrier, to prevent oozing out.

Figure 61:
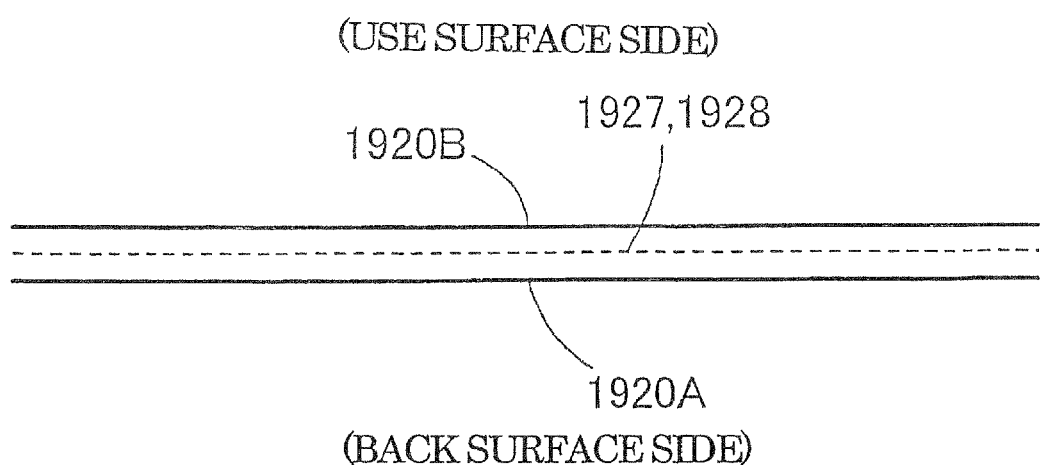
FIG. 61 is a sectional view of an external sheet construction.

On the other hand, in the edge of the longitudinal direction of the front side section F and the back side section B, as shown in FIGS. 60 and 61 schematically, between nonwoven fabrics 1920A and 1920B of the external sheet 1920 in the waist portion W, the waist section elastic members 1925 and 1926, composed of thin rubber thread are arranged and fastened by a hot-melt adhesive, in a state of being elongated, so as to be expanded and, contracted, keeping an space in parallel to the edges of the waist opening portion WO, in order to improve fitting property of the waist section. The space between and the number of the waist section elastic members 1925, 1926 can be determined suitably. However, for example, about 4 to 8 mm is preferable as the space, and 4 to 10 is preferable as the number.

Further, in the invention, the under waist section elastic members 1927, 1928 are provided along the peripheral direction in the lower belly portion of the front side section F and an abdomen portion of the back side section B in the under waist portion U extending the region from the waist portion W of the front side section F and the back side section B to the crotch region L. In this embodiment, the under waist section elastic members 1927 of the front side section F is provided at right and left side portions of the product excluding almost whole portion of the absorbent core 1913 of the portion ranging from the joint portion 1930 of one side to the joint portion 1930 of the other side.

The nonwoven fabric sheet 1920A of the back side of the external sheet 1920 is not less than 40% in opacity under JIS P 8138, more preferably not less than 50%. Opacity can be measured based on JIS P 8138 by "a colorimetric hue color-difference meter", which is a product of NIPPON DEN-SHOKU KOGYOSHA KK.

Moreover, back side nonwoven fabric sheet 1920A is preferably 40 g/m$^2$ or less, 0.1 mm or more in thickness, and 10 mm or more in rigidity under JIS P 8143. When the thickness of the back side of the nonwoven fabric sheet is 0.1 mm or more, hiding property of the elastic members 1927 and 1928 is improved, and when the basis weight is 40 g/m² or less and the rigidity is 10 mm or less, a disposable diaper having a superior expansion and contraction elasticity, and soft and puffy feeling is provided. The color of the nonwoven fabric sheet 1920A of the back side of the external sheet 1920 is preferably white in view of feeling of purity. The same is the nonwoven fabric 1920B formed in laminates.

In the embodiment shown in the figure, as the under waist section elastic members 1927 and 1928, thin rubber threads are used. The diameter of the elastic members used is not more than 925 dtext, more preferably, not more than 620 dtex. The color of the under waist section elastic members 1927 and 1928 is preferably white, which is the same color with the back side of the nonwoven fabric sheet. The color of the elastic members is made translucence or transparent, as needed. For example, if the elastic members having the opacity of 50% or more are used, existence of which is not recognizable and it is preferable.

In the front side section F and the back side section B, 15 to 40 pieces of under waist section elastic members 1927 and 1928 are arranged and fastened between nonwoven fabrics of the external sheet 1920 in parallel respectively. In the above arrangement, spaces therebetween in the under waist section elastic members are preferably 7.0 mm or less, more preferably 5.0 mm or less in four direction of the lower crotch section. Mutual space between the under waist section elastic members 1927 and 1928 is preferably the same with the space between the waist section elastic members 1925, 1926 . . . , or shorter than the same.

Also, thin rubber thread used for the under waist section elastic members 1927 and 1928 can be smaller in extension stress and a cross-sectional outer diameter than the thin rubber thread used for the waist section elastic members 1925 or can be substantially the same with the thin rubber thread. Specifically thin rubber thread used here has preferably the extension stress of the range of 4 to 17 g, at the time of 150% extension, especially the extension stress of the range of 5 to 10 g.

On the other hand, in the nineteenth embodiment, the crotch section elastic member 1927a is also formed in right and left portion of crotch section L, excluding the central portion thereof. As for the crotch section elastic member 1927a also, which is arranged and fixed between nonwoven fabrics, the expansion and contraction elastic member is preferably 925 dtex, more preferably 620 dtex or less in diameter, and 7.0 mm or less in space in the longitudinal direction similarly to the waist section elastic members.

Twentieth Embodiment

Figure 62:
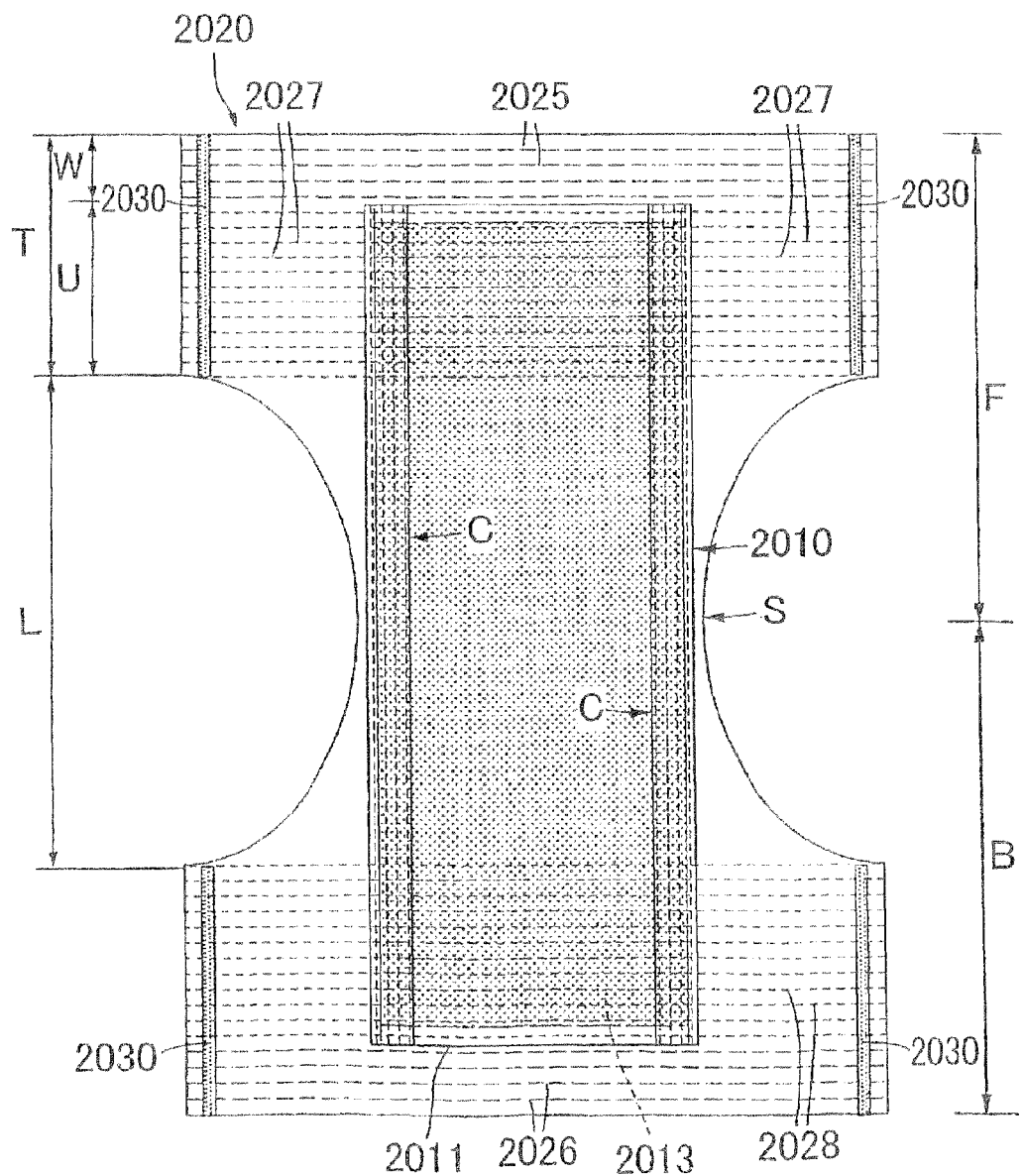
FIG. 62 is a plan view from a use surface side showing a development of a pant-type of disposable diaper according to the twentieth embodiment of the invention.
Figure 63:
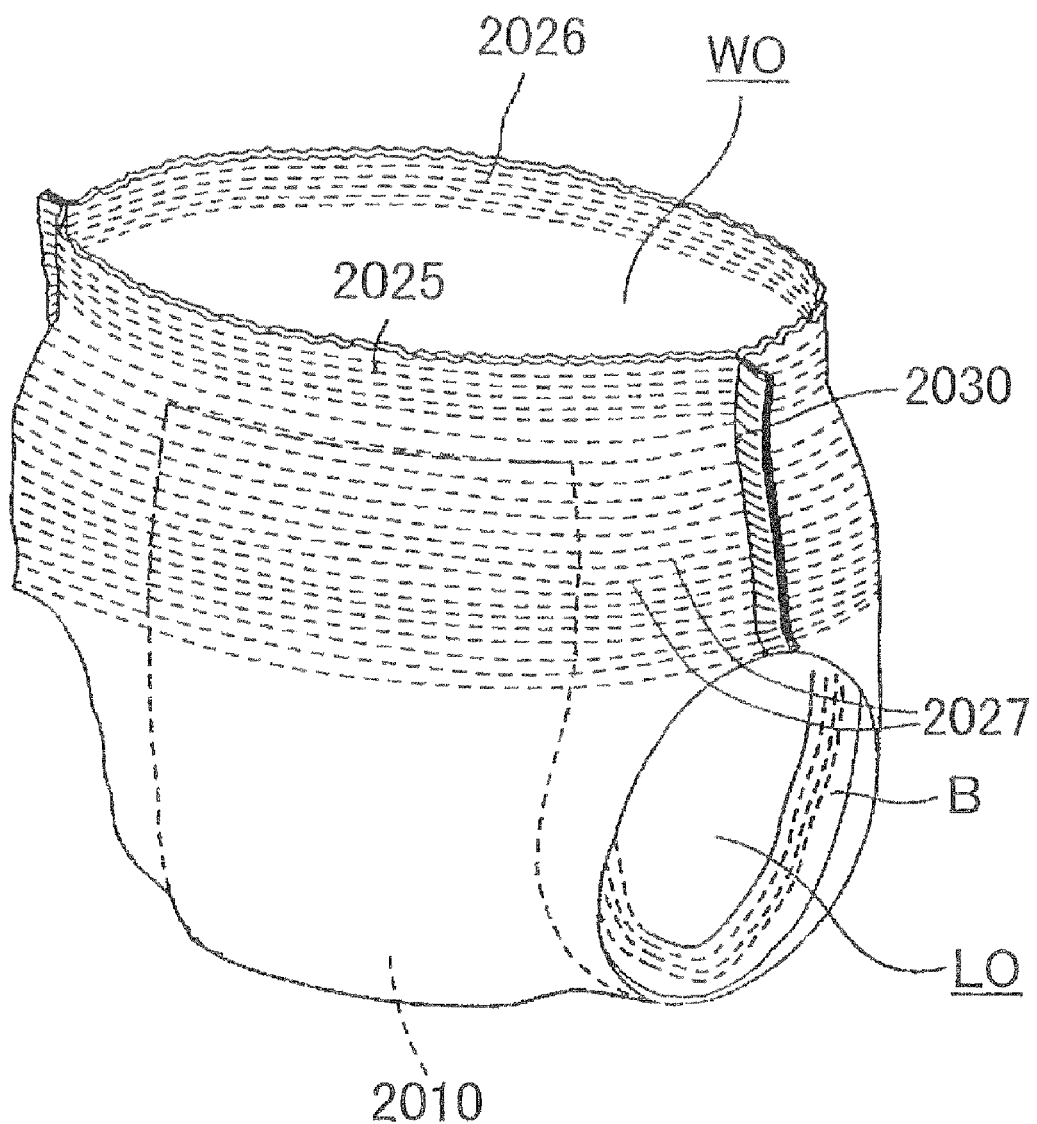
FIG. 63 is a perspective view of a product according to the twentieth embodiment of the invention.

The twentieth embodiment shown in FIG. 62 and FIG. 63 differs from the nineteenth embodiment in that no crotch section elastic member 1927a is formed in the crotch portion L, and the under waist section elastic members 2027, 2028 traverse the paper diaper main body 2010, and are arranged and fixed continuously in the peripheral direction between the nonwoven fabrics.

Twenty-First Embodiment

Figure 64:
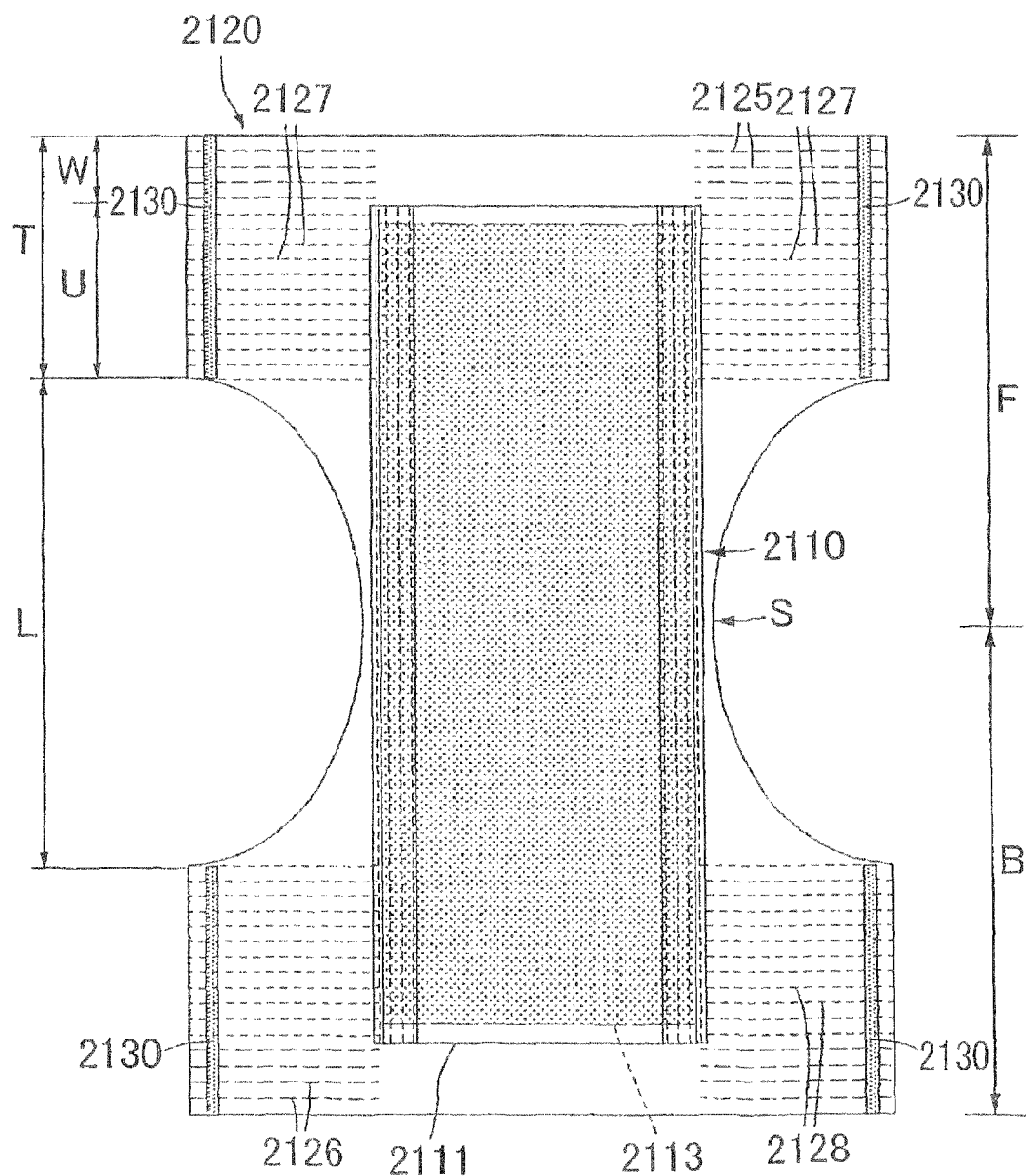
FIG. 64 is a plan view from a use surface side showing a development of a pant-type of disposable diaper according to the twenty-first embodiment of the invention.
Figure 65:
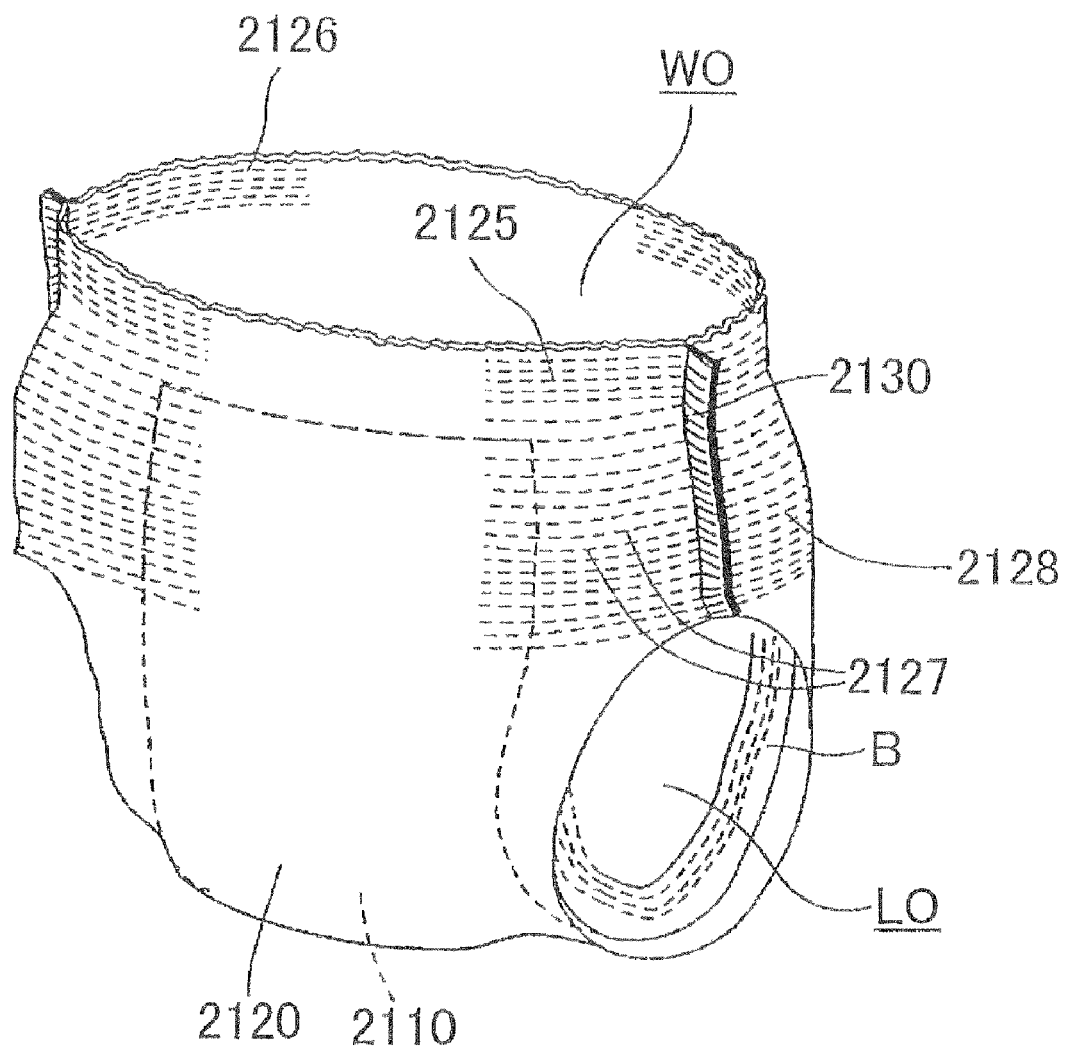
FIG. 65 is a perspective view of a product according to the twenty-first embodiment of the invention.

FIG. 64 differs from the nineteenth embodiment in that no crotch section elastic members 1927a are formed in the crotch portion L, and the waist section elastic members 2125, 2126 are not formed in the central portion, but in the side portions only. This constitution is shown in an development view similar to FIG. 58. A use state is shown in FIG. 65.

Twenty-Second Embodiment

Figure 66:
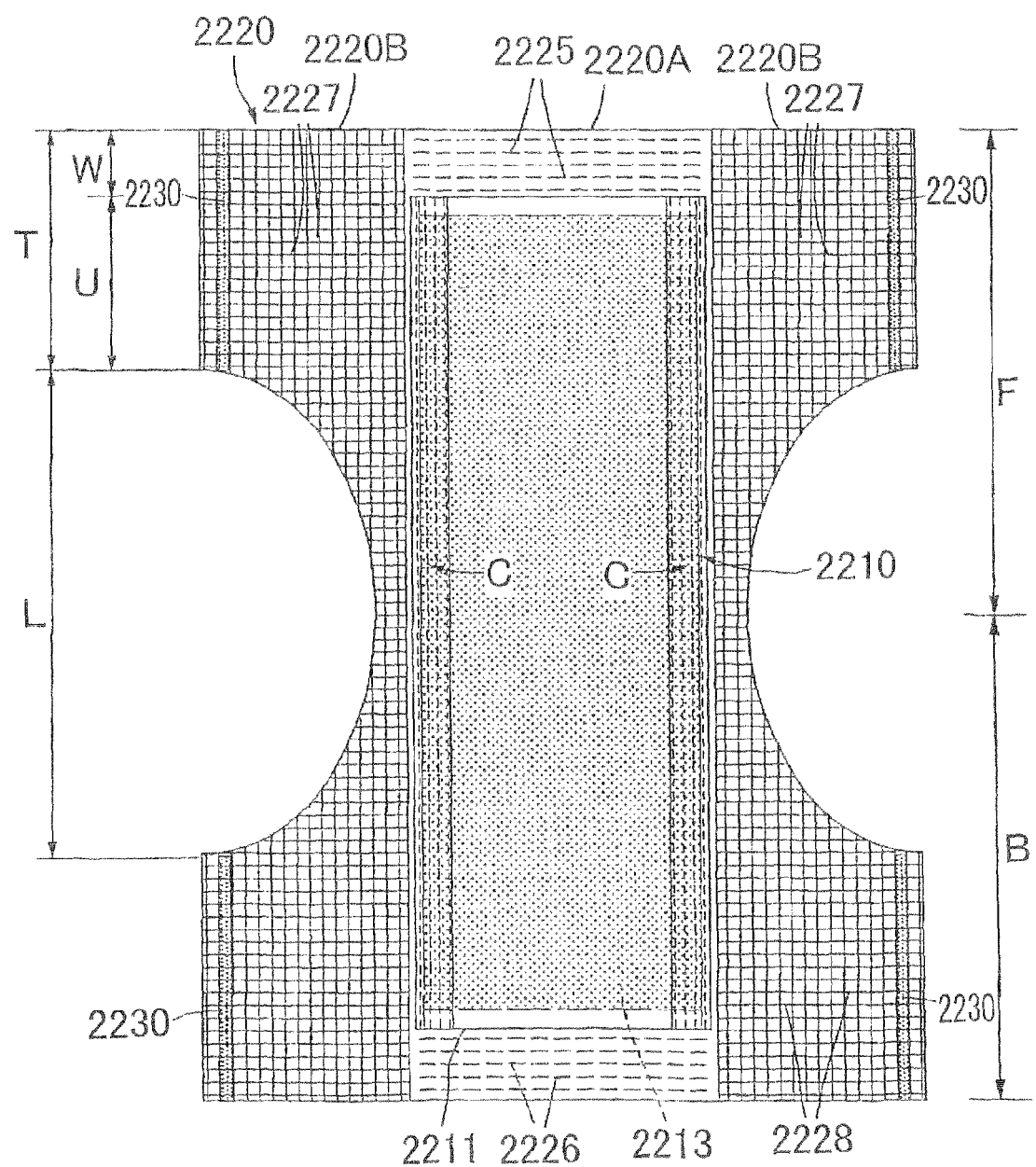
FIG. 66 is a plan view from a use surface side showing development of a pant-type of disposable diaper according to the twenty-second embodiment of the invention.

FIG. 66 is a view showing the external sheet 2220 having a central sheet 2220A which is provided at the center in the width direction, and side sheets 2220B, 2220B which are provided at both sides, wherein each side sheet 2220E, 2220B includes thin rubber thread fixed between nonwoven fabrics in a shape of net, or lattice. The side sheets 2220B, 2220B of both sides are bonded to the central sheet, so that each side sheet 2220S, 2220B is elastic circumferentially and laterally. The thin rubber threads in the peripheral direction in the above case, form the elastic members of waist section W and of lower waist section U.

[Supplementary Explanation and Other Embodiments of Each Mode of Pant-Type of Disposable Diaper]

Figure 67A:
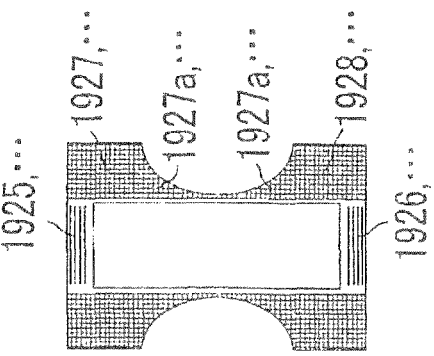
FIG. 67(A) to FIG. 67(F) are explanatory views of arrangements of the elastic members.
Figure 67B:
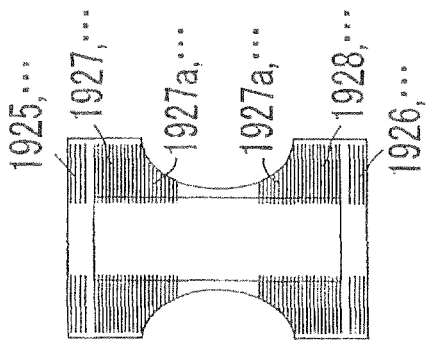
Figure 67C:
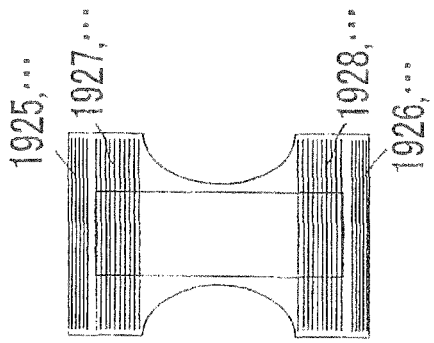
Figure 67E:
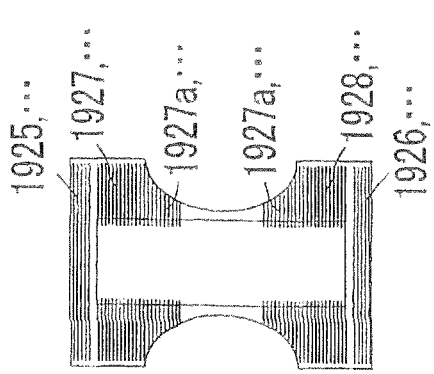
Figure 67D:
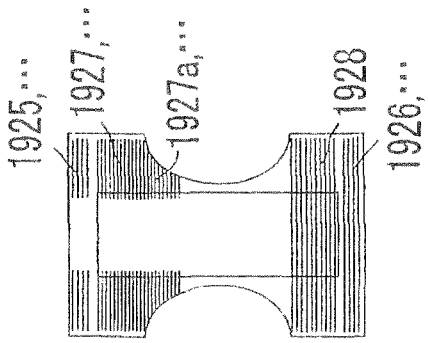
Figure 67F:
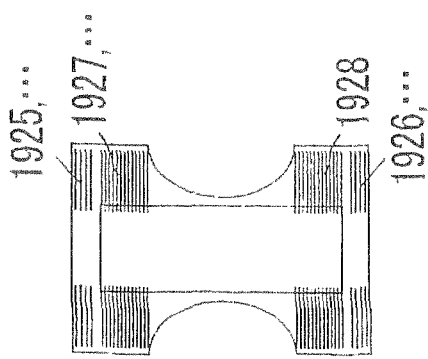

FIG. 67(A) to FIG. 67(D) are views from the nineteenth embodiment to the twenty-second embodiment, which are summarized conceptionally. As supposed by comparing them with each other, the shaping elastic members of the invention adopts two arrangement forms. In one form, the waist section elastic members 1925, 2025, . . . , 1926, 2026, . . . , and the under waist section elastic members 1927, 2027, . . . , 1928, 2028, . . . , traverse the paper diaper main body 1910, 2010, . . . and are arranged and fastened continuously in the peripheral direction. In the other form, the above elastic members do not exist in the central portion having the absorbent core 1913, 2013, . . . but are arranged and fastened in right and left side portions of a product only. These forms can be alternatively selected. In addition, whether the arrangement of the crotch section elastic members 1927a, 2027a, are needed or not can also be selected. Further, the arrangement form of the elastic members can be differentiated between the front side section F and the back side section B. Accordingly, shown in FIG. 67(E) as another embodiment, the waist section elastic members 1925 . . . , 1926 . . . and the under waist section elastic members 1927 . . . , 1928 . . . , are arranged and fastened to right and left side portion of a product only, without existing in the central portion of the position having the absorbent core 1913 . . . , and further the crotch section elastic members 1927a are not formed. In addition, as shown in FIG. 67(F), as another embodiment, the waist section elastic members 1925 . . . , 1926 . . . and the under waist section elastic members 1927 . . . , 1928 . . . are arranged and fastened to the right and left side portion of a product only, without existing in the position having the absorbent core 1913 . . . and further the crotch section elastic members 1927a . . . are also adopted. Thus, the arrangement form of the elastic members is suitably selected. When the under waist section elastic members 1927, 1928 . . . or the crotch section elastic members 1927a are arranged and fastened to the right and left side portion only, without existing in the central portion having the absorbent core 1913 . . . , there are two cases such as a case that edges of the under waist section elastic members 1927 . . . , 1928 . . . , or the edges of the crotch section elastic members 1927a . . . are overlapped on the side edges of the absorbent core 1913 . . . , and a case that the above edges are positioned in spaced from the side edges of the absorbent core 1913 . . . without reaching the side edges of the absorbent core 1913.

In addition, in the above embodiment, a rectangular shaped paper diaper main body 1910 . . . is bonded to the nearly sandglass shaped external sheet 1920 . . . . However, the liquid permeable top sheet 1911 . . . formed in the same shape with the external sheet 1920 . . . may be provided to interpose absorbent body AB therebetween. Further, the external sheet 1920 and paper diaper main body 1910 . . . may be integrally formed, without demarcating.

The sheet that constitutes the external surface of a product is formed of laminates of two, three or more nonwoven fabrics having air permeability and water repellent property. However, one nonwoven fabric is satisfactory, and in this case, the elastic members 1927 . . . , 1928 . . . can be bonded to a use face of the nonwoven fabric. Furthermore, a plastic sheet can be interposed in a middle point between the laminated nonwoven fabrics, or laminated on the use face of the back side of the nonwoven fabric.

The under waist section elastic members 1927 . . . or the under waist section elastic members 1928 . . . may be arranged in a shape of lattice or net. An embodiment of the above arrangement is shown in FIG. 66. In this embodiment also, the elastic members have spaces to one another in the longitudinal direction defined in the invention.

The above-described disposable diaper has the elastic members that exist over 60% or more, preferably over 70% or more, or more preferably over 90% or more of length range of the body peripheral region, extending from the waist opening edges to the leg opening initial end. Therefore, in a maximum of 40% region, a neat appearance as a whole is not spoiled even when the under waist section elastic members 1927 . . . has no diameter nor space defined by the invention.

Figure 68:
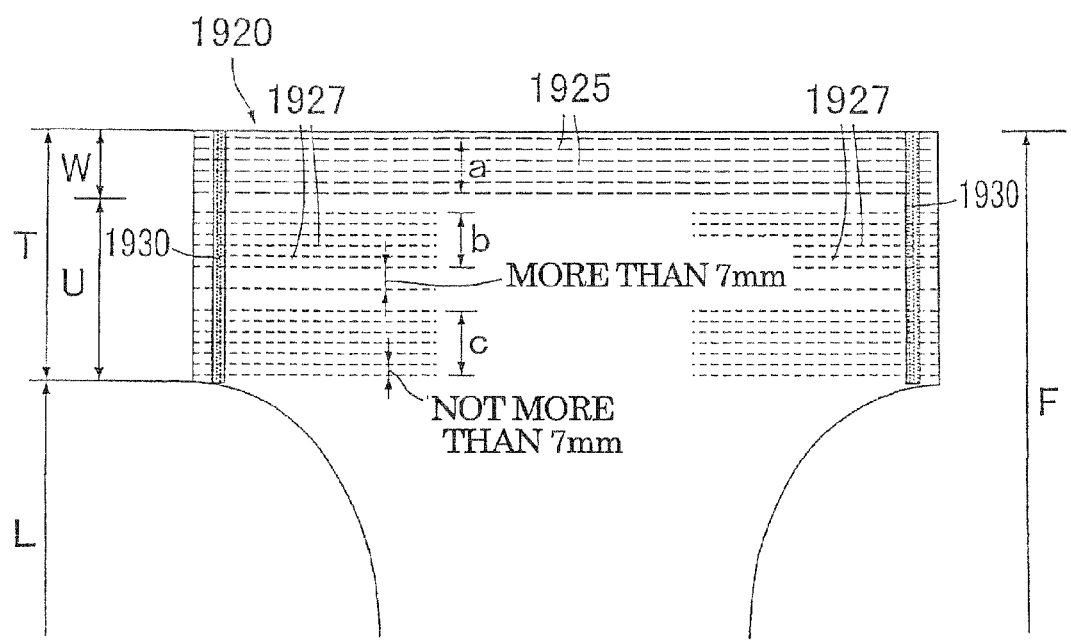
FIG. 68 is an explanatory view about an arrangement ratio of the elastic members.

To be explained in detail in conjunction with a specific embodiment, as shown in FIG. 68 in enlarged view, the length range "a" of the waist section elastic members 1925 . . . , 1925 . . . with spaces each of which is arranged at 7 mm or less and the length range "b" and "c" with spaces each of which is arranged at 7 mm or less, excluding the length range with spaces each of which is more then 7 mm from the arrangement of the under waist section elastic members 1927 . . . , 1925, are totaled. Ratio of the total value to the length of body peripheral region T (that is, (a+b+c)/T is defined to be 60% or more.

By the way, in the external sheet 1920, the elastic members can be provided in various forms so that the crotch section or the lower crotch section may be fitted to the physique of a wearing person.

Figure 69:
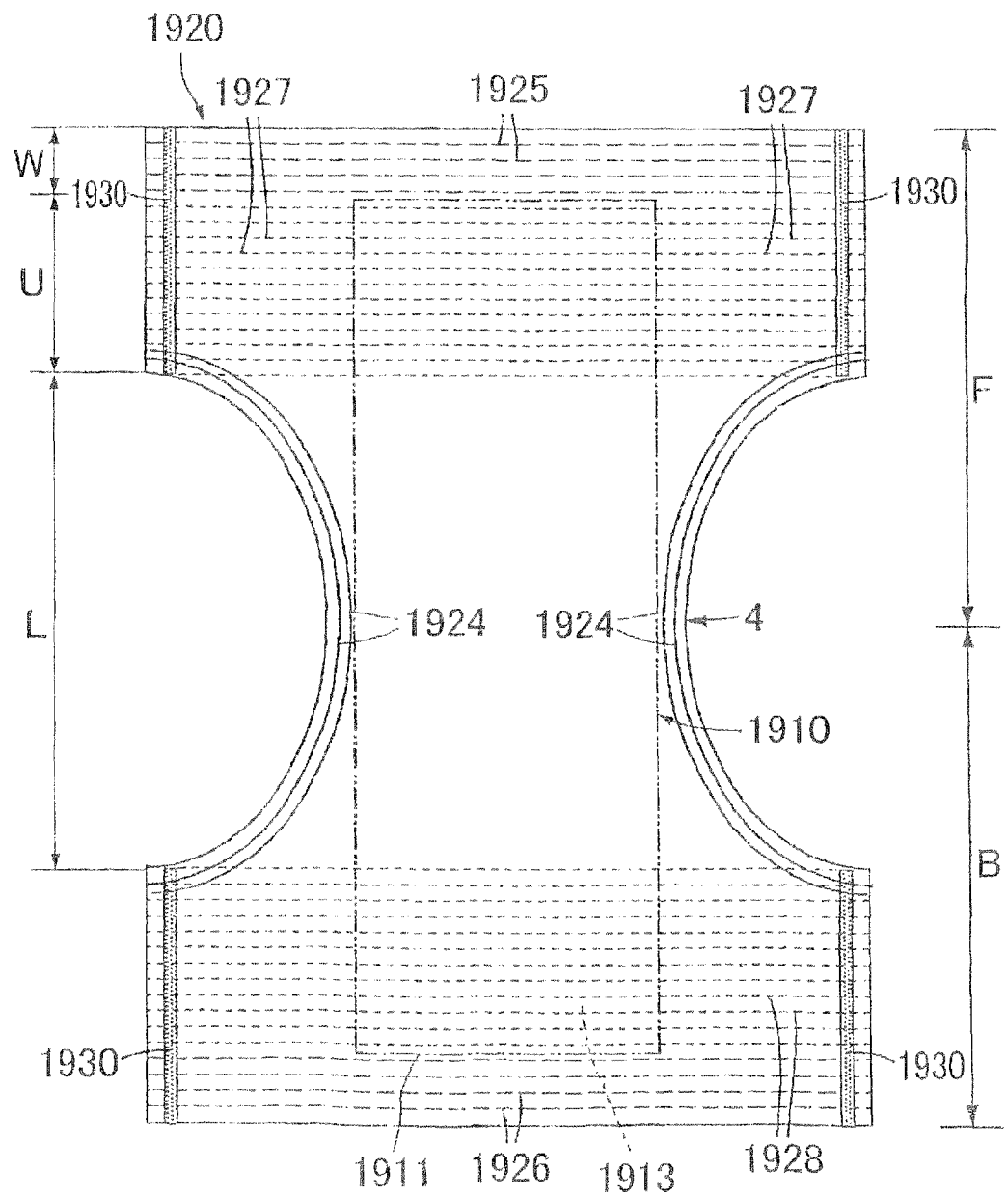
FIG. 69 is a plan view from a use surface side showing a development of another embodiment.

FIG. 69 is a view showing the crotch section elastic members 1924, 1924 which are fixed between the nonwoven fabrics in parallel to the leg opening edges of the crotch section L, between the edge of the front side section and the edge of the back side portion. This arrangement prevents the body fluid from oozing out by shrinkage of the leg opening LO by the crotch section elastic member 1924. In order to clarify the crotch section elastic members 1924, 1924, the paper diaper main body 1910 is shown by a phantom line.

Figure 70:
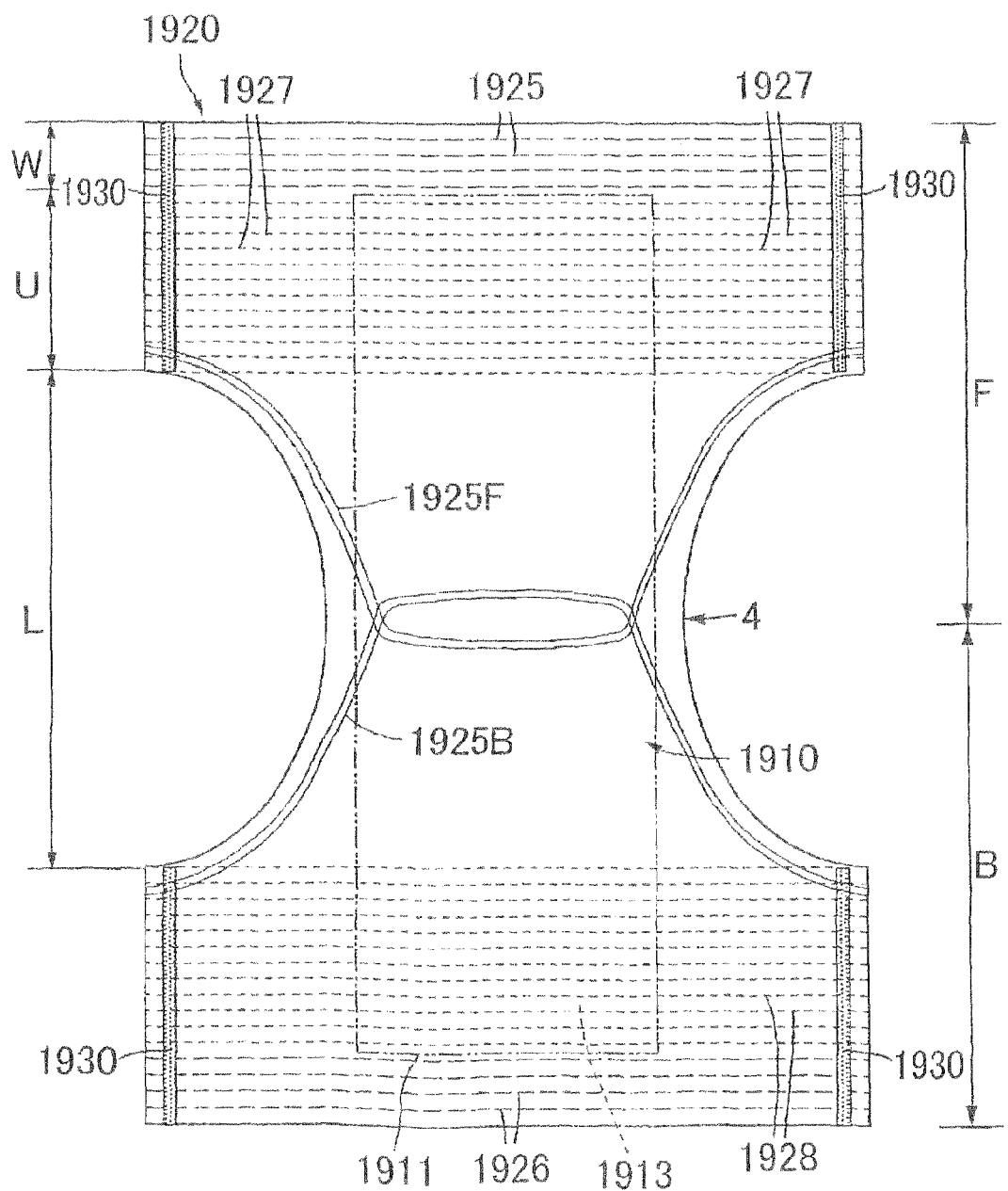
FIG. 70 is a plan view from a use surface side showing a development of another embodiment.

In FIG. 70, the crotch section and lower crotch section elastic members 1925F and 1925B are fixed between nonwoven fabrics of the external sheet 1920, to cross the crotch section, extending from the edge of the left side portions to the edge of the right side portions, in the front side F and the back side B. In this embodiment, the crotch and lower crotch section elastic member 1925F in the front side F and the crotch and lower crotch section elastic member 1925B in the back side B are partially crossed to each other.

Figure 71:
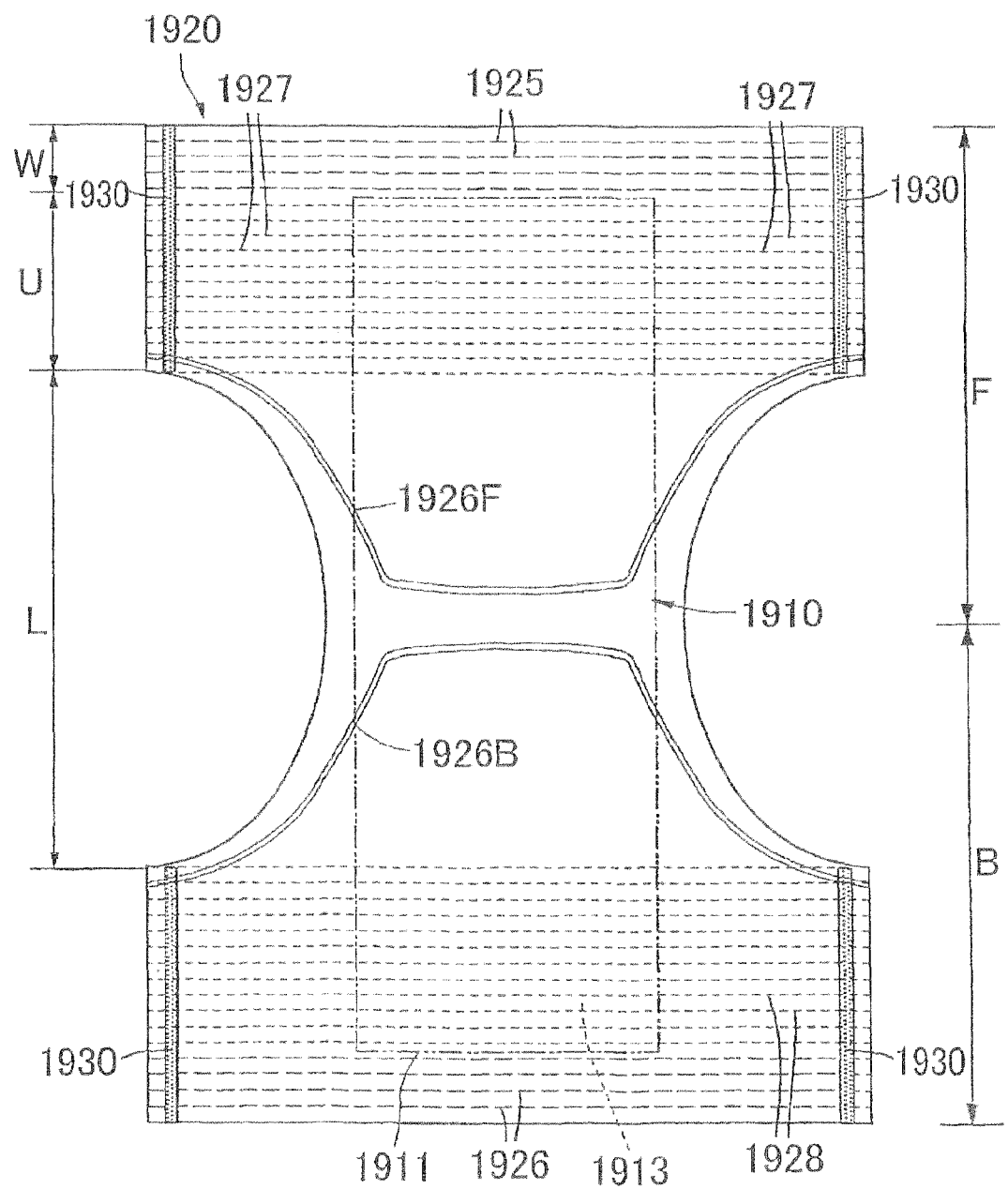
FIG. 71 is a plan view from a use surface side showing a development of a further embodiment.

In FIG. 71, the crotch section and lower crotch section elastic members 1926F and 1926B are fixed between nonwoven fabrics of the external sheet 1920, to cross the crotch section, extending from the edge of the left side portions to the edge of the right side portions, in the front side F and the back side B. In this embodiment, the crotch and lower crotch section elastic member 1926F in the front side F and the crotch and lower crotch section elastic member 1926B in the back side B are parallel to each other in the lower crotch portion.

Figure 72:
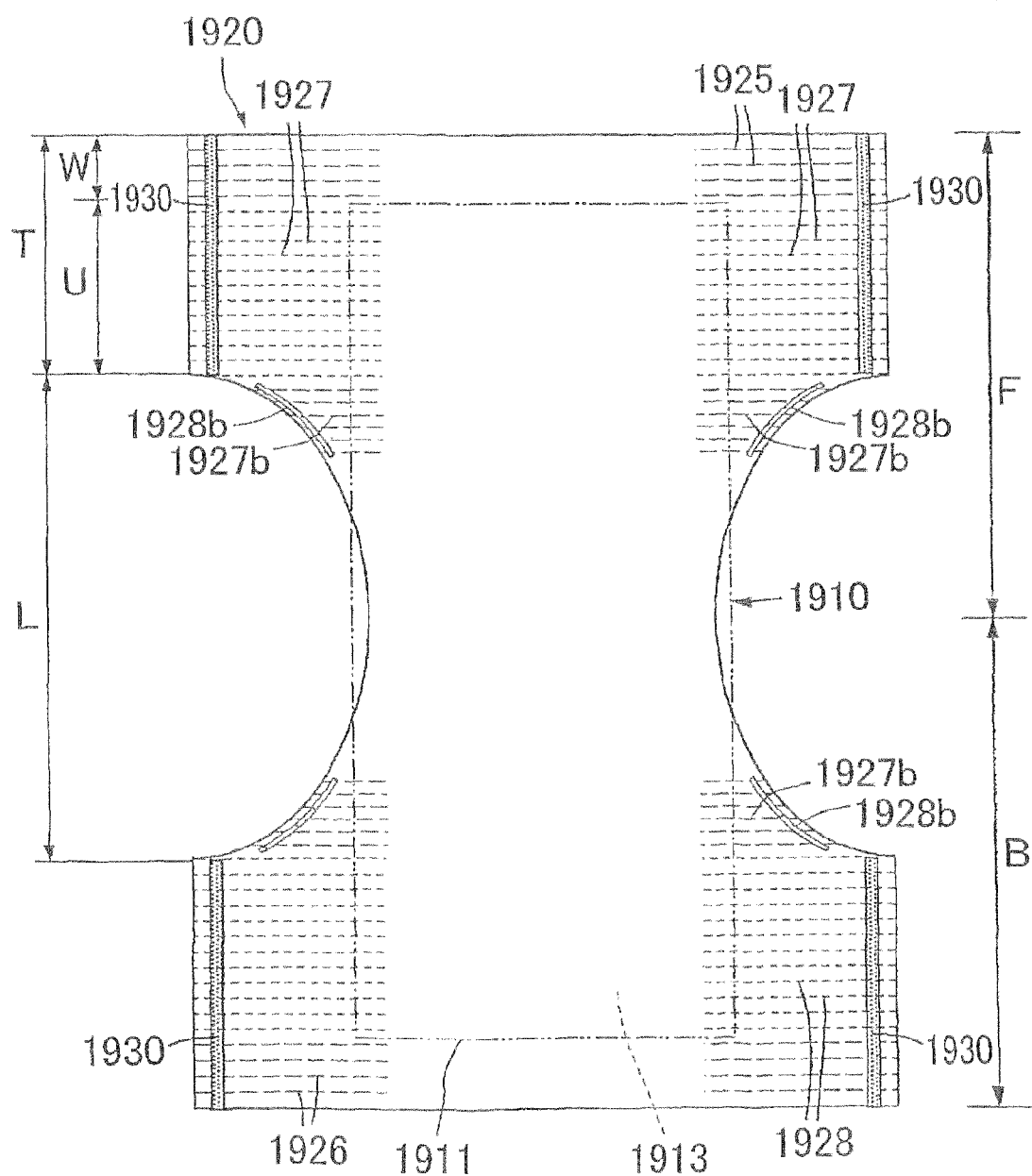
FIG. 72 is a plan view from a use surface side showing a development state in case of including shaping elastic members.

On the other hand, as shown in FIG. 72, in the lower crotch section, the width of the external sheet 1920 can be smaller than that of the paper diaper main body 1910, especially that of the absorbent core 1913. In the embodiments shown in FIG. 72 or described before, the external sheet 1920 protruded to the outside of the side edges of the absorbent core 1913 is flatterable, to generate a problem that a neat appearance of a product as a whole cannot be obtained. Then, the shaping elastic member 1927b may be formed between the nonwoven fabrics of the external sheet 1920 at both sides of the crotch section L, similarly to the crotch section elastic member 1927a of the nineteenth embodiment, so that the protruding external sheet 1920 is brought near the center side, to thereby solve the fluttering problem. In this case, the outer edges of the group of shaping elastic members 1927b is fixed by seal lines 1928b by a hot-melt adhesive, to thereby prevent pulling of the outer edge of the shaping elastic members 1927b group to the central side.

Figure 73:
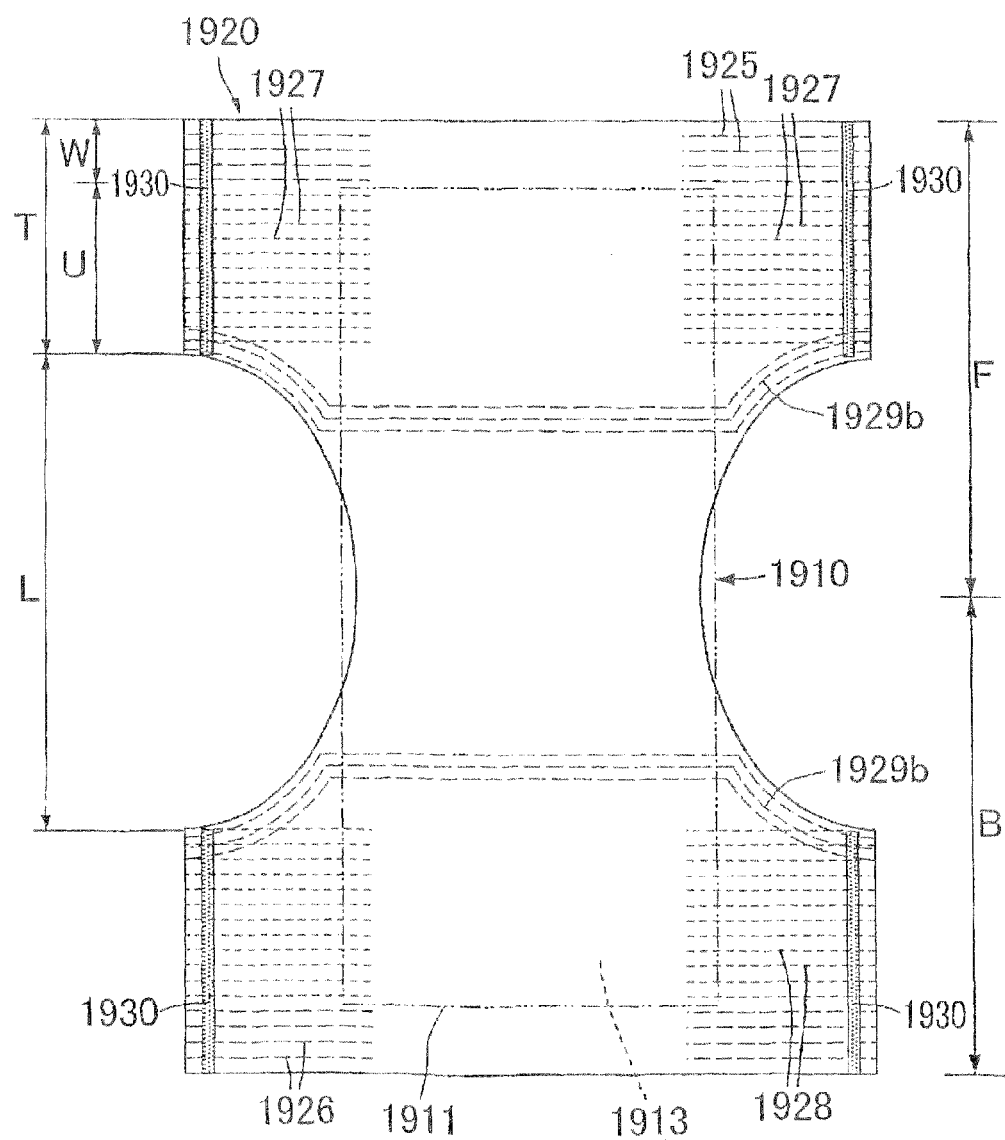
FIG. 73 is a plan view from a use surface side showing a development state in case of including shaping elastic members in another embodiment.

In FIG. 73, to solve the fluttering problem, the shaping elastic members 1929b, 1929b are fixed between the nonwoven fabrics of the external sheet 1920, to cross the crotch section, extending from the edge of the left side portions to the edge of the right side portions, in the front side F and the back side B. In this form, the portion in the peripheral direction, of the external sheet 1920 which protrudes outwardly from the side edges of the absorbent core 1913, is brought near the center side by the shaping elastic members 1929b, to thereby solve the fluttering problem. In addition, the edge of the shaping elastic member 1929 extends to the edge of the side portion, so as to raise the crotch section toward the body peripheral region T. Thereby, slack of an abdomen and a buttock is solvable and a neat appearance is obtained.

Twenty-Third Embodiment

Figure 74:
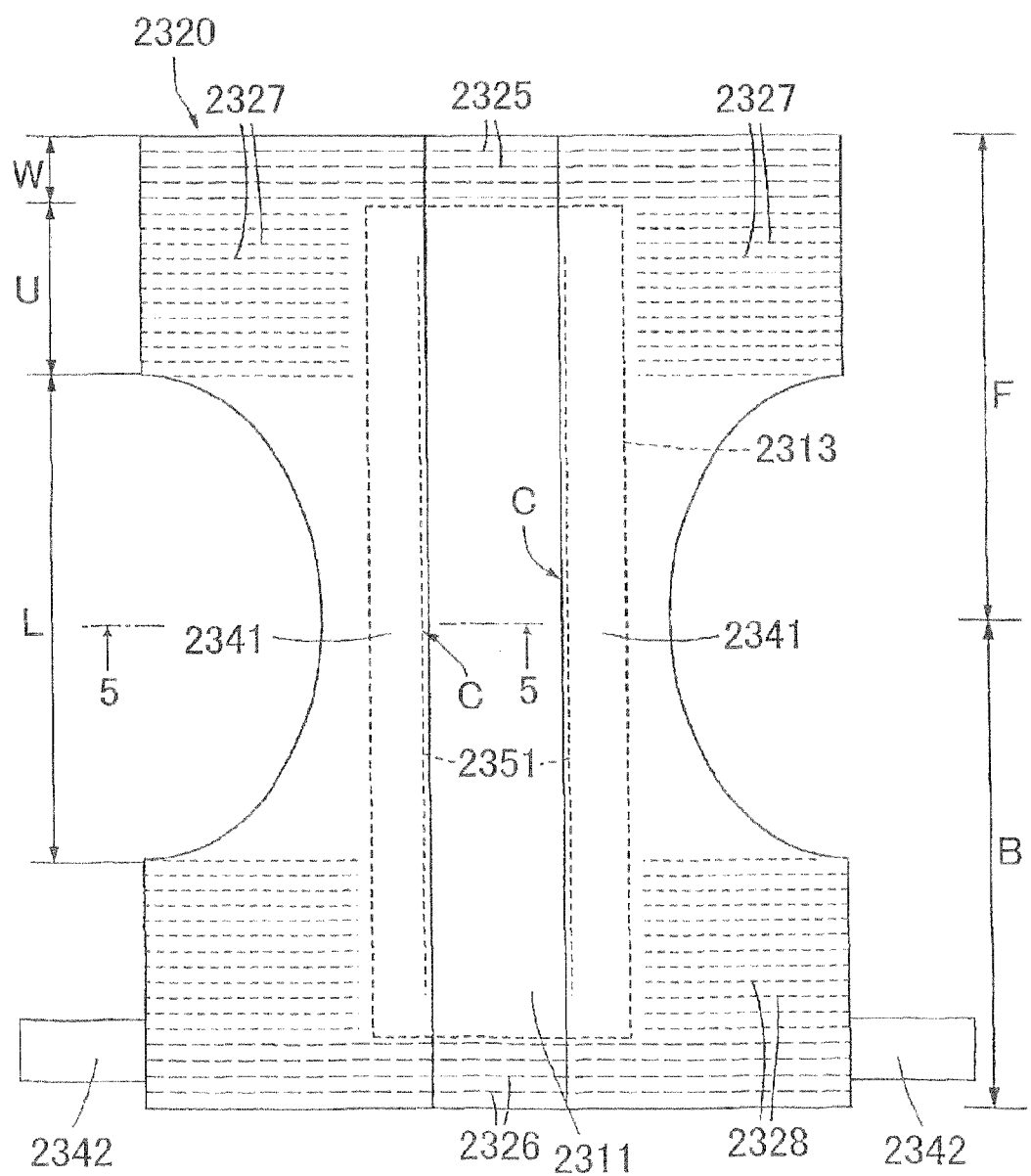
FIG. 74 is a plan view from a use surface side showing a development of a pant-type of disposable diaper according to the twenty-third embodiment of the invention.
Figure 75:
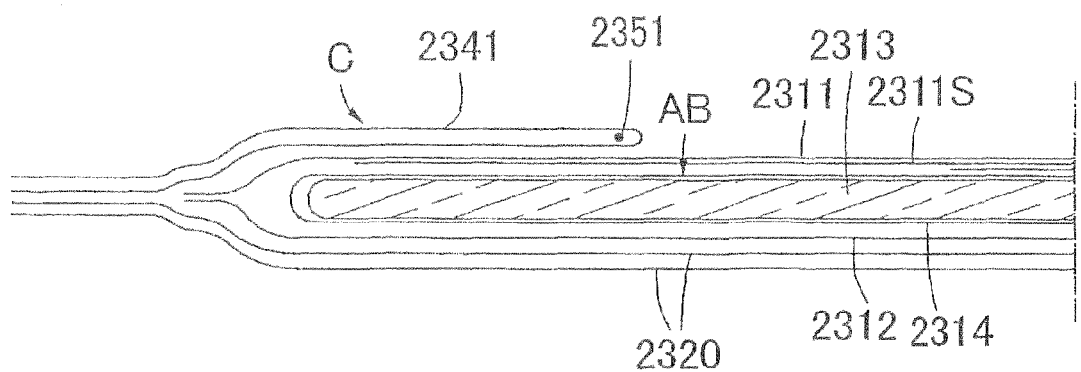
FIG. 75 is a sectional view taken along the line 5-5 thereof.

As describe above, the invention also targets a tape type disposable diaper in addition to a pant-type of disposable diaper. The twenty-third embodiment is shown in FIG. 74 and FIG. 75. This embodiment includes rising sheets 2341, 2341 on both sides, and elastic members 2351, 2351 on tip end portion of the free rising portion, to thereby form the rising cuffs C, C. The rising sheet 2341 is bonded to back side sheet 2320 that is similar to the external sheet. The reference numeral 2342 is a tape fastener for joint of right and left side edges by bringing both right and left side portions of the back side to the right and left side portions of the belly side to be matched. In this embodiment, in the edge of the longitudinal direction of the front side section F and the back side section B, and between nonwoven fabrics of the external sheet 2320 in the waist portion W, the waist section elastic members 2325, 2326 . . . composed of thin rubber thread with spaces are arranged and fastened in a state of being elongated, so as to be expanded and contracted, keeping in parallel to the edges of the waist opening portion WO, in order to improve fitting property of the waist section. Further, the under waist section elastic members 2327, 2328 are formed at lower belly section of the front side section F and at buttock section of the back side section B along the body peripheral direction.

Twenty-Fourth Embodiment

Figure 76:
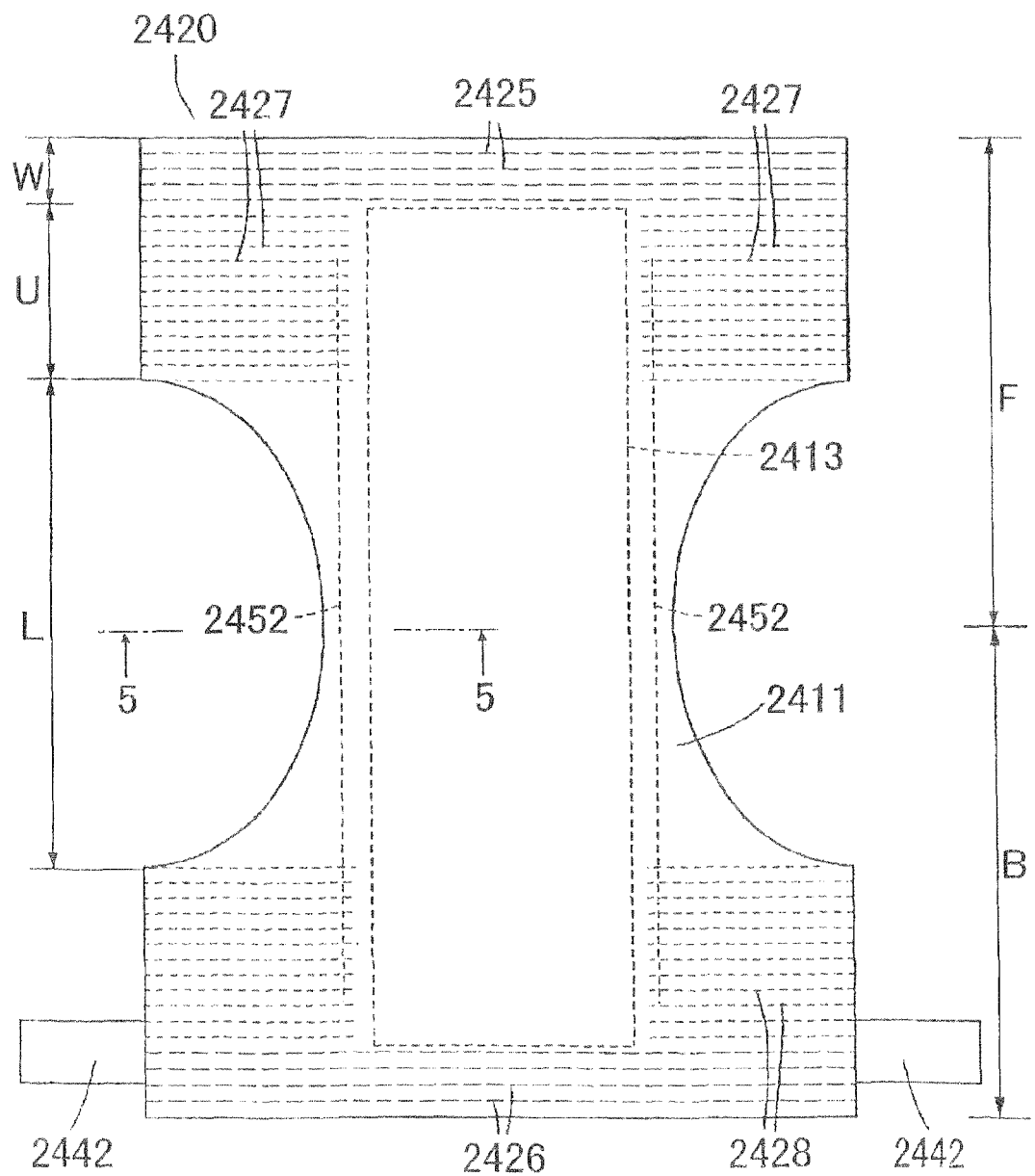
FIG. 76 is a plan view from a use surface side showing a development of a pant-type of disposable diaper according to the twenty-forth embodiment of the invention.
Figure 77:
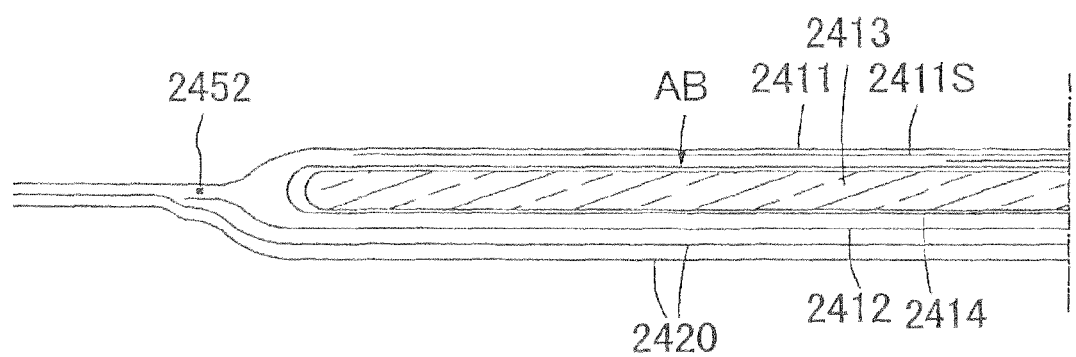
FIG. 77 is a sectional view taken along the line 5-5 thereof.

The twenty-fourth embodiment for showing another tape type of disposable diaper is shown in FIG. 76 and FIG. 77. No rising cuffs are used in the embodiment. In the outer flap portions of the absorbent core 2413, elastic members 2452, 2452 are fixed along the longitudinal direction between a liquid-permeable top sheet 2411 and a back sheet 2412. In the embodiment, waist section elastic members 2425, 2426 and under waist section elastic members 2427, 2428 are also provided.

(Elastic Members)

Figure 78:
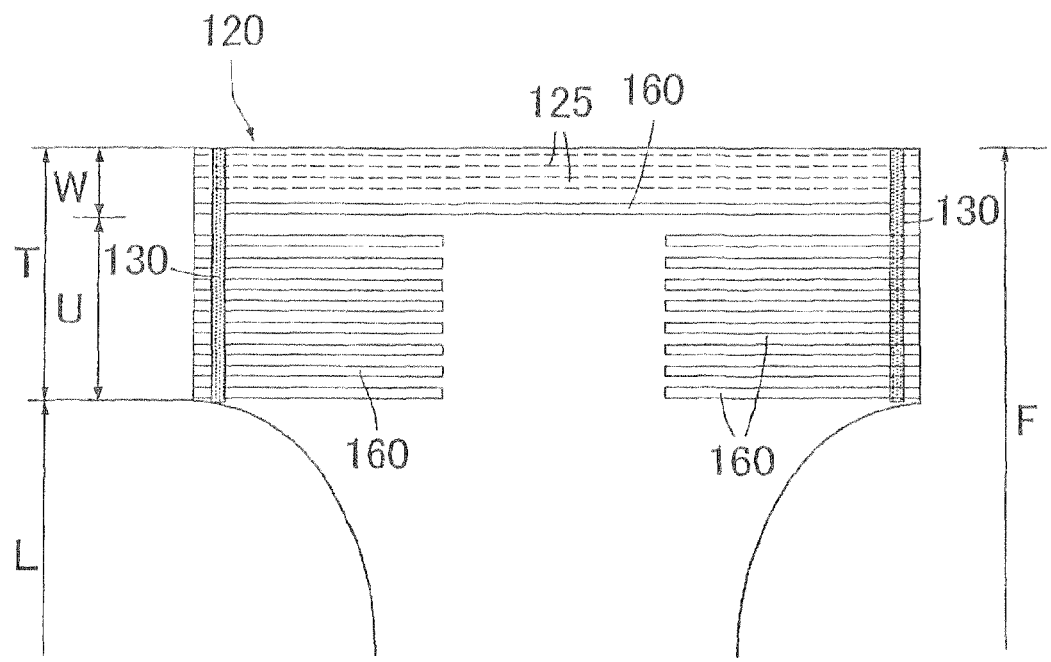
FIG. 78 is a plan view from a use surface side showing a development state in case of including other elastic members in another embodiment.
Figure 79:
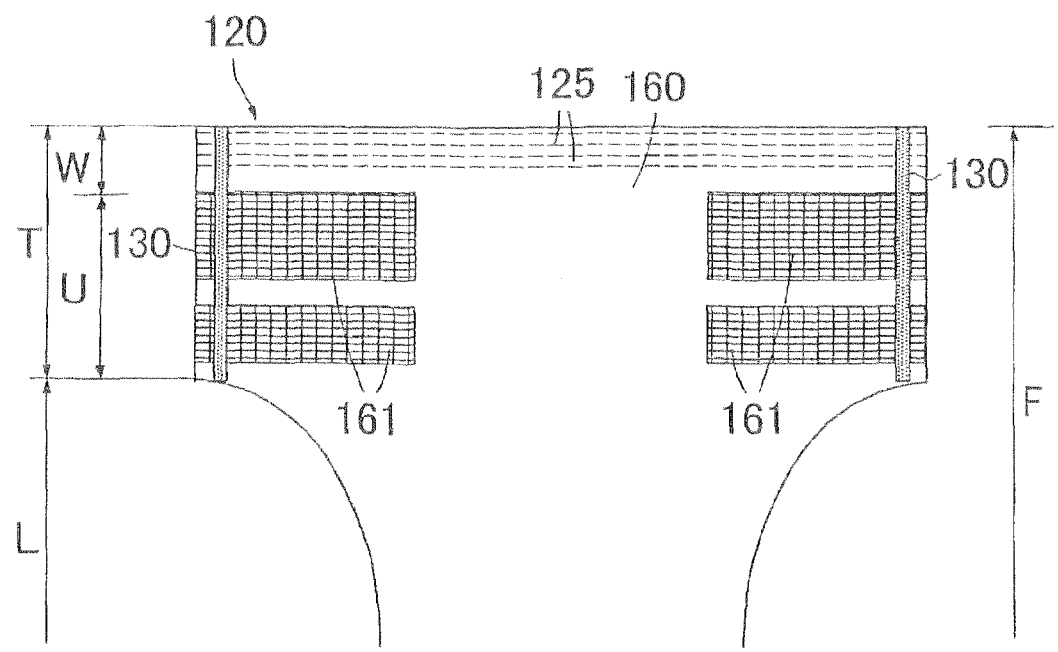
FIG. 79 is a plan view from a use surface side showing a development state in case of including other elastic members in a further embodiment.
Figure 80A:
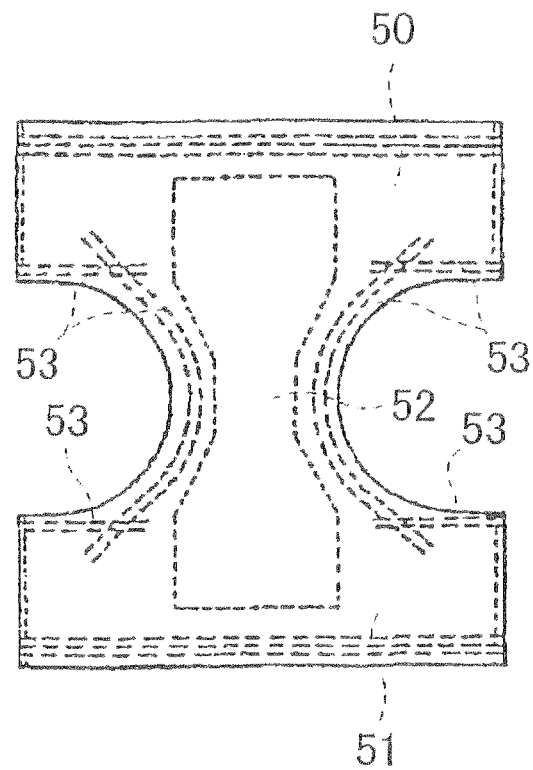
Figure 80B:
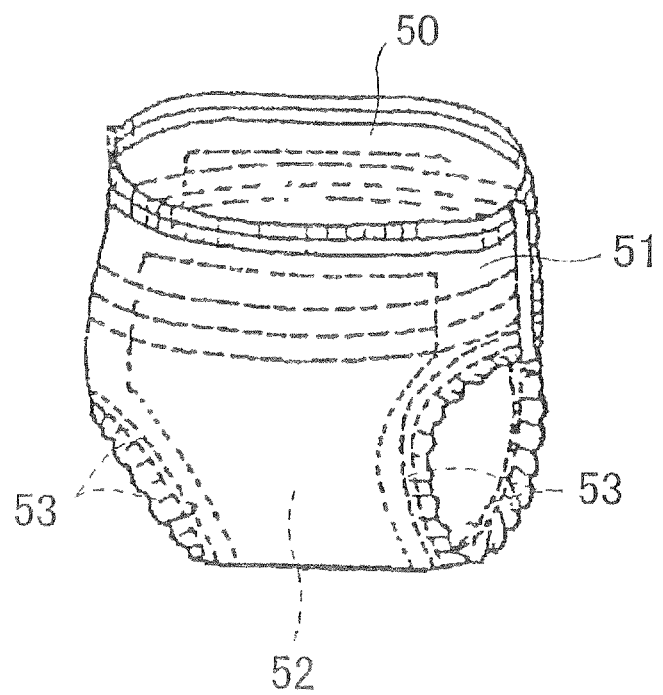
Figure 81A:
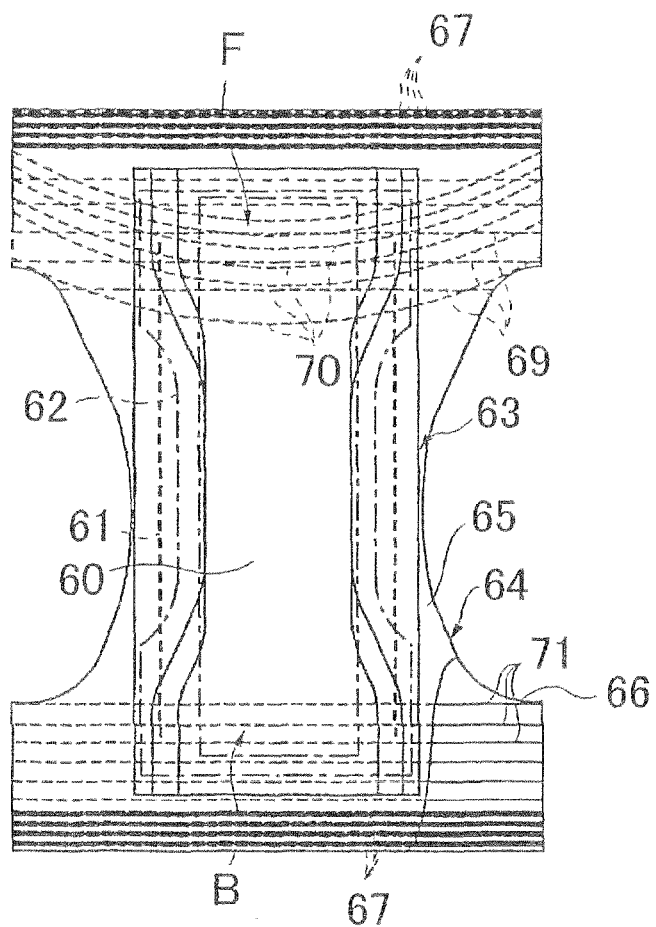
FIG. 81(A) is a development and FIG. 81(B) is a view showing a product state thereof.
Figure 81B:
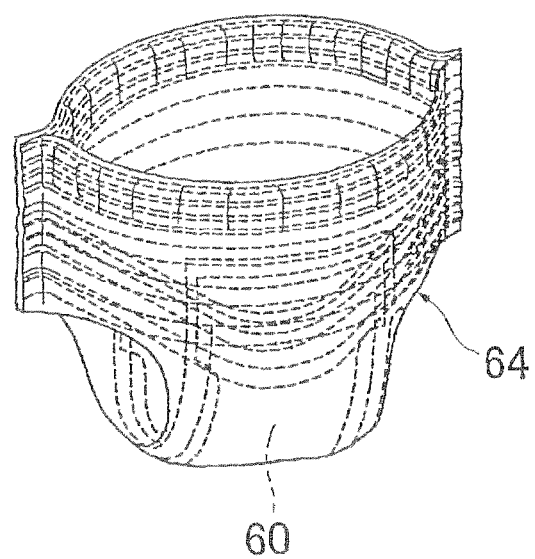

As each of the above-described elastic members, in addition to materials such as a natural rubber and a synthetic rubber, an elastic material such as urethane or the like is also used. An elastic member like a belt with small width or a sheet-like elastic member having large area is also used. As examples of such a material, a belt, a film or a sheet, made of urethane or the like, can be listed. As a film, a no-porous film or a porous film, and further as a sheet, a mesh sheet can be suitably selected. An arrangement embodiment of the no-porous film 160 is shown in FIG. 78. Also, an arrangement embodiment of mesh film 161 is shown in FIG. 79. In these embodiments, it is also important that the region of the elastic members fixed to the external sheet 120 of the product covers 60% or more of the length region of the under waist section.

Example

Various kinds of back side nonwoven fabric sheets having different opacities to each other were used to thereby observe the hiding property of the elastic members 1927 . . . , 1928 . . . , and wrinkles that were occurred on the outer surface of a product obtained when the diameter and arrangement spaces between the elastic members of the under waist section were changed in various way. The results were shown in Table 1.

TABLE 1

| | Back Side Nonwoven Fabric Sheet (%) | Elastic members | | | Hiding property of the elastic member | Occurrence state of wrinkles | |
|---|---|---|---|---|---|---|---|
| | | Form | Diameter (dtex) | Space (mm) | | Continuity | Wrinkle pitch |
| Example 1 | 40% | Thin rubber thread | 620 | 7 | good | (2) | 2.2 |
| Example 2 | 50% | Thin rubber thread | 620 | 7 | Superior | (2) | 2.2 |
| Example 3 | 50% | Thin rubber thread | 500 | 7 | Superior | (1) | 2.0 |
| Example 4 | 50% | Thin rubber thread | 500 | 5 | Superior | (1) | 1.6 |
| Example 5 | 50% | Thin rubber thread | 620 | 5 | Superior | (1) | 1.8 |
| Example 6 | 50% | Thin rubber thread | 620 | 8.5 | good | (3) | 3.5 |
| Example 7 | 50% | Thin rubber thread | 650 | 7 | good | (2) | 2.8 |
| Example 8 | 50% | Thin rubber thread | 800 | 7 | good | (4) | 3.1 |
| Example 9 | 50% | Thin rubber thread | 1000 | 10 | Good~failure | (4) | ✶ |
| Example 10 | 50% | Film-shaped | 50 □m in thickness | | Superior | (1) | 2.1 |
| Comparative Example 1 | 30% | Thin rubber thread | 620 | 7 | failure | (2) | 2.2 |

Notes:
"hiding property" = superior: hardly visible, good: approximately invisible, failure: visible . . . about elastic members
"continuity" = longitudinally continuous state of a product is evaluated by rank.
(1): 80% or more are continuous.
(2): 50 to 80% are continuous.
(3): 20 to 50% are continuous.
(4): non-continuous, or even when continuous only 20%
(Wrinkle pitch) = Space between the mountain ridges projected to the external surface side.
✶ = a pitch is at random in the range of 2 to 7 mm, and cannot be specified.

From the result above, in order to obtain a good hiding property of the elastic members, opacity is preferably 40% or more, especially 50% or more. In addition, both of the diameters of the elastic members and the space between the members in longitudinal direction are involved in the generation of the wrinkles. And in only the range mentioned above embodiments, finely structured wrinkles are generated, even when it cannot be obviated, thereby presenting a neat appearance.

As described above, according to the nineteenth embodiment to the twenty-fourth embodiment, the elastic members are invisible or hardly visible, so as to make a wearing person undaunted by anxiety about excessive tightening and formation of traces of rubber. In addition, problem that elastic members are visible is overcome, to thereby obtain an advantage that high-class feeling of a product and good finish thereof, which are appealing to consumers, is achieved.

POSSIBILITY OF INDUSTRIAL UTILIZATION

As described above, a disposable diaper of the invention is not only excellent functionally but also in appearance, and can be used for either adults or children. Especially, a neat appearance of leg section and crotch section is obtained, therefore it is extremely suitable as a paper diaper for adults.

What is claimed is:

1. A pant-type disposable diaper, comprising:
an external sheet;
a paper diaper main body which extends in a vertical direction on an inner surface of the external sheet by setting a crotch section as a center;
a waist opening in a use-condition; and
left and right leg openings which are formed by left and right leg cut-out portions in the use-condition,
wherein:
the paper diaper main body comprises at least a liquid-permeable top sheet, an absorbent core, a leakage preventing sheet and rising cuffs,
the pant-type disposable diaper includes a body peripheral region formed of a waist portion and a lower waist section and a crotch region,
a plurality of waist section elastic members which are rubber threads or narrow bands are provided at the waist portion so as to be parallel to each other in a circumferential direction and so as to have a constant space between adjacent waist section elastic members in a vertical direction,
a plurality of under waist section elastic members are provided at the lower waist section in a range of 60% or more of the lower waist section in the vertical direction so as to be parallel to each other in the circumferential direction and so as to have a space between adjacent under waist section elastic members that is smaller than the constant space between adjacent waist section elastic members,
a plurality of shaping elastic members are provided at at least one of a front side section and a back side section of the crotch region so as to be parallel to each other in the circumferential direction and so as to have a space between adjacent shaping elastic members that is smaller than the constant space between adjacent waist section elastic members,
a pair of left and right leg section elastic members are extended along the left and right leg cut-out portions, respectively,
the under waist section elastic members and the waist section elastic members are not provided at a central portion of the absorbent core,
the shaping elastic members are provided from left and right leg opening edges to positions corresponding to both side portions of the absorbent core, respectively,
the shaping elastic members expand and contract between the leg opening edges and the positions corresponding to said both sides portions of the absorbent core,
the liquid-permeable top sheet extends to a back side of the absorbent core so as to wrap both side edges of the absorbent core and is bonded at the back side of the absorbent core,
a raising sheet which forms the rising cuffs further wraps said both side edges of the absorbent core which is wrapped by the liquid-permeable top sheet from an upper side and is bonded at the back side of the absorbent core so that fastening initial ends of the raising sheet form rising ends of the rising cuffs,
the rising cuffs have free portions in sides nearer to tip ends than the rising ends, elastic members are included in the tip ends of the free portions, and elastic members are included in root sides of the free portions, and
both side portions of the paper diaper main body are raised by a contraction force of the elastic members included in the tip ends and the root sides of the free portions.

2. The pant-type disposable diaper as claimed in claim 1, wherein:
the under waist section elastic members are provided from left and right fastening portions of the body peripheral region to positions corresponding to said both side portions of the absorbent core, respectively, and
the under waist section elastic members expand and contract between the fastening portions and the positions corresponding to said both side portions of the absorbent core.

3. The pant type disposable diaper as claimed in claim 1, wherein:
an extension stress and a cross-sectional diameter of the under waist section elastic members are smaller than an extension stress and a cross-sectional diameter of the waist section elastic members, and
an extension stress and a cross-sectional diameter of the shaping elastic members are smaller than the extension stress and the cross-sectional diameter of the waist section elastic members.

4. The pant-type disposable diaper as claimed in claim 3, wherein the space between adjacent under waist section elastic members and the space between adjacent shaping elastic members are equal.

5. The pant-type disposable diaper as claimed in claim 1, wherein:
the under waist section elastic members and the shaping elastic members are provided at the inner surface of the external sheet, and
the external sheet is a nonwoven fabric sheet which has an opacity of not less than 40% under JIS P 8138.

6. The pant-type disposable diaper as claimed in claim 5, wherein:
the under waist section elastic members and the shaping elastic members have a transparency of not less than 50% and have an extension magnification in a range of 150% to 350%.

7. The pant-type disposable diaper as claimed in claim 5, wherein:
the under waist section elastic members and the shaping elastic members are interposed between the external sheet and a use side nonwoven fabric having a same color as the external sheet and which faces the external sheet.

8. The pant-type disposable diaper as claimed in claim 1, wherein the crotch section of the external sheet does not extend outside side edges of the absorbent core.

9. The pant-type disposable diaper as claimed in claim 1, wherein:
- the plurality of under waist section elastic members have a diameter of not more than 620 dtex and are provided so that the space between adjacent under waist section elastic members is not more than 7 mm, and
- the plurality of shaping elastic members have a diameter of not more than 620 dtex and are provided so that the space between adjacent shaping elastic members is not more than 7 mm.

* * * * *